(12) United States Patent
Elazar et al.

(10) Patent No.: US 9,775,504 B1
(45) Date of Patent: Oct. 3, 2017

(54) CONTROLLING AN INTRAORAL MIRROR WITH AN INTEGRATED CAMERA, AND APPLICATIONS THEREOF

(71) Applicant: Dental SmartMirror, Inc., Chicago, IL (US)

(72) Inventors: Gidon Oded Elazar, Cohav Yair (IL); Dan Zidkiahu Harkabi, Moshav Lachish (IL); Joshua Israel Wachspress, Modi'in (IL)

(73) Assignee: DENTAL SMARTMIRROR, INC., Chicago, IL (US)

( * ) Notice: Subject to any disclaimer, the term of this patent is extended or adjusted under 35 U.S.C. 154(b) by 0 days.

(21) Appl. No.: 15/603,884

(22) Filed: May 24, 2017

Related U.S. Application Data

(62) Division of application No. 15/360,470, filed on Nov. 23, 2016, now Pat. No. 9,681,799.

(60) Provisional application No. 62/354,694, filed on Jun. 25, 2016, provisional application No. 62/354,273, filed on Jun. 24, 2016, provisional application No. 62/343,034, filed on May 30, 2016, provisional application No. 62/341,629, filed on May 26, 2016.

(51) Int. Cl.
| | |
|---|---|
| *A61B 1/247* | (2006.01) |
| *A61B 1/05* | (2006.01) |
| *A61B 1/06* | (2006.01) |
| *A61C 13/34* | (2006.01) |
| *A61B 1/00* | (2006.01) |
| *A61B 5/06* | (2006.01) |
| *A61B 5/00* | (2006.01) |
| *A61C 9/00* | (2006.01) |
| *A61C 13/00* | (2006.01) |
| *H05B 37/02* | (2006.01) |

(52) U.S. Cl.
CPC .......... *A61B 1/247* (2013.01); *A61B 1/00009* (2013.01); *A61B 1/00016* (2013.01); *A61B 1/00032* (2013.01); *A61B 1/00041* (2013.01); *A61B 1/00105* (2013.01); *A61B 1/05* (2013.01); *A61B 1/063* (2013.01); *A61B 1/0607* (2013.01); *A61B 1/0676* (2013.01); *A61B 5/0086* (2013.01); *A61B 5/0088* (2013.01); *A61B 5/067* (2013.01); *A61C 9/0073* (2013.01); *A61C 13/0004* (2013.01); *A61C 13/34* (2013.01); *H05B 37/0227* (2013.01)

(58) Field of Classification Search
None
See application file for complete search history.

(56) References Cited

U.S. PATENT DOCUMENTS

| | | | | |
|---|---|---|---|---|
| 4,727,416 A | * | 2/1988 | Cooper | A61B 1/00091 348/164 |
| 4,993,945 A | * | 2/1991 | Kimmelman | A61B 1/247 219/219 |
| 6,276,934 B1 | * | 8/2001 | Rakocz | A61B 1/0669 433/29 |
| 7,713,058 B2 | | 5/2010 | Takahashi | |
| 9,585,549 B1 | * | 3/2017 | Elazar | A61B 1/247 |
| 9,681,799 B1 | * | 6/2017 | Elazar | A61B 1/247 |

(Continued)

*Primary Examiner* — W B Perkey
(74) *Attorney, Agent, or Firm* — Sterne, Kessler, Goldstein & Fox P.L.L.C.

(57) ABSTRACT

Disclosed embodiments integrate a camera into an intraoral mirror. Integrating a camera into an intraoral mirror provides an efficient way to record and display what is visible to the healthcare provider in the mirror.

18 Claims, 32 Drawing Sheets

(56) References Cited

U.S. PATENT DOCUMENTS

| | | | | |
|---|---|---|---|---|
| 2002/0151941 A1* | 10/2002 | Okawa | ........... | A61B 90/30 |
| | | | | 607/99 |
| 2004/0152037 A1* | 8/2004 | Schick | ........... | A61B 1/24 |
| | | | | 433/29 |
| 2005/0003323 A1* | 1/2005 | Katsuda | ........... | A61B 1/00089 |
| | | | | 433/29 |
| 2005/0026104 A1* | 2/2005 | Takahashi | ........... | A61B 1/05 |
| | | | | 433/31 |
| 2007/0225557 A1* | 9/2007 | Lee | ........... | A61B 1/05 |
| | | | | 600/109 |
| 2008/0096154 A1* | 4/2008 | Rakocz | ........... | A61B 1/247 |
| | | | | 433/29 |
| 2009/0073275 A1* | 3/2009 | Awazu | ........... | G03B 7/16 |
| | | | | 348/222.1 |
| 2009/0161337 A1* | 6/2009 | Matsui | ........... | G03B 15/05 |
| | | | | 362/5 |
| 2010/0097517 A1 | 4/2010 | Koh | | |
| 2013/0286174 A1* | 10/2013 | Urakabe | ........... | A61B 1/00009 |
| | | | | 348/66 |
| 2014/0023984 A1* | 1/2014 | Weatherly | ........... | A61B 1/00016 |
| | | | | 433/31 |
| 2014/0272765 A1* | 9/2014 | Andreiko | ........... | A61B 1/00006 |
| | | | | 433/27 |
| 2015/0004557 A1* | 1/2015 | Hillebrandt | ........... | G06Q 50/22 |
| | | | | 433/29 |
| 2015/0237256 A1 | 8/2015 | Sakurai | | |
| 2016/0373728 A1* | 12/2016 | Cho | ........... | H04N 13/0253 |

\* cited by examiner

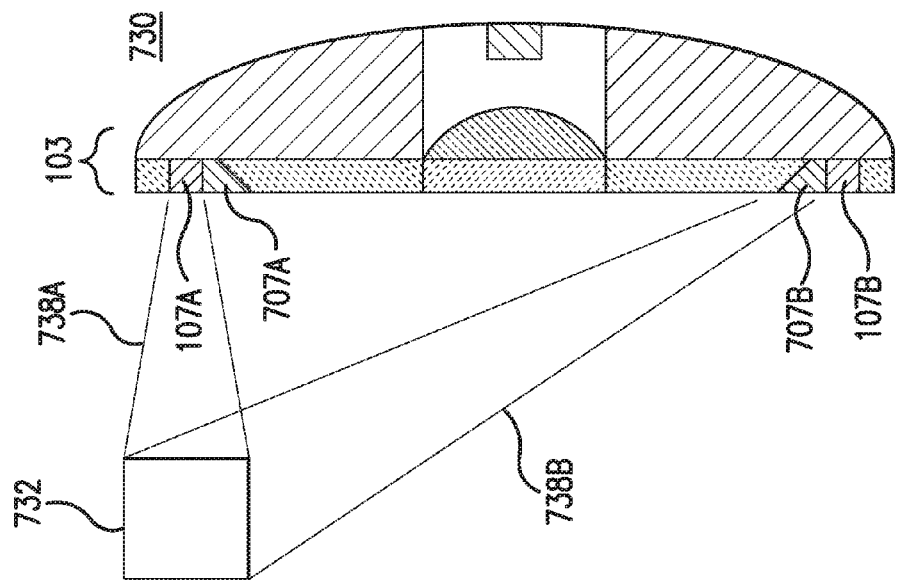
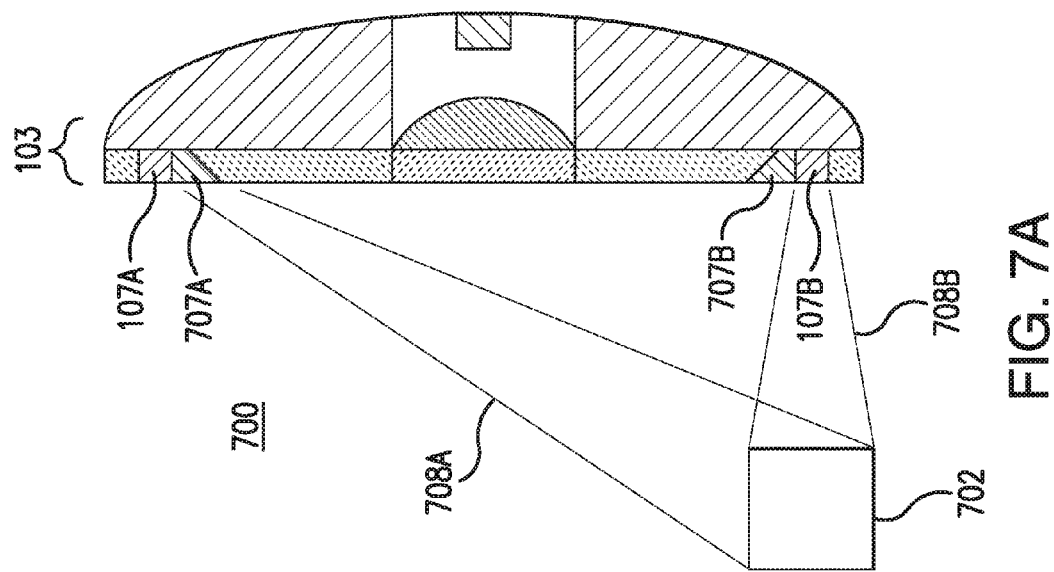
FIG. 7A
FIG. 7B

CONTROLLING AN INTRAORAL MIRROR WITH AN INTEGRATED CAMERA, AND APPLICATIONS THEREOF

BACKGROUND

Field

This field is generally related to dental instruments.

Related Art

Intraoral mirrors, also known as mouth mirrors, are among the most functional and frequently used of dental instruments. Viewing objects in a mouth directly is difficult due to a limited, or perhaps nonexistent, line of sight. Intraoral mirrors allow a health care provider (HCP), for example dentist, hygienist and others, to indirectly view teeth and other objects in a patient's mouth, such as the patient's gums and tongue, by observing their reflections in a mirror. Health care providers use the intraoral mirror for a variety of tasks, including, but not limited to, evaluation and diagnosis, treatment selection, and even to assist the treatment itself. A health care provider may use other tools, such as a dental hand piece, in conjunction with the mirror to conduct procedures, such as tooth preparation, when the procedures are conducted in areas that are not directly visible.

Not only are they used as a visual aid, intraoral mirrors are also used as rigid tools to manipulate or protect objects in a patient's mouth. For example, a health care provider may use an intraoral mirror to shift a patient's cheek to make space for treatment or to expand the mouth space for improved visibility. In addition, an intraoral mirror can protect soft and hard tissue structures of a patient's mouth while other parts of the mouth are treated.

Since an intraoral mirror is in contact with a patient's tissues inside their mouth, the mirror goes through sterilization after each treatment. In some cases, sterilization is done using a process known as "autoclaving." Autoclaving subjects the mirror to high temperature and pressure, perhaps using steam. Because the mirror must be sterilized after each treatment, a dental office possesses multiple such mirrors. The mirror, made mostly of glass and metal, can withstand the autoclaving process. But, due to frequent use and sterilization, the mirror eventually loses some of its clarity and its reflectiveness, thus needing replacement.

In addition to intraoral mirrors, intraoral cameras are becoming more widespread in dental clinics. Intraoral cameras have principally two uses. First, intraoral cameras are used to describe a diagnosis and explain a possible treatment to a patient. For example, to explain a diagnosis or treatment, the health care provider may display images of the patient's mouth parts (e.g. teeth) to the patient. Second, the intraoral cameras are used to record the state of portions of the patient's mouth. For example, a health care provider may capture a photographic image of the patient's mouth before or after treatment.

Intraoral cameras are commonly shaped as pens, with an image capture device at their tip, pointed sideways. The tip helps orient the HCP as to where to position the camera to capture images of the desired area of the mouth. The captured images are presented in a display, and the navigation is done using the display. However, because these displays are the only viewfinder for the cameras, their use adds time to a dental appointment. Additionally, in a common usage scenario, heath care providers would commence a mouth inspection using a mouth mirror, if a need to capture an image arises, the HCP would have to switch the intraoral mirror with an intraoral camera. This may seem a minor hassle, but in the busy environment of a dental clinic, it reduces the frequency of capturing images.

Some dental procedures use dental composite resin material to glue fillings or build up structures on teeth during restoration procedures. After applying the material it is hardened using an instrument called a light cure. The light cure is used to illuminate the resin with light within the spectrum of visible blue to ultraviolet. This light might be harmful to the eye, therefore an eye protector is used by the healthcare provider while using the light cure. To perform such procedure, a health care provider applies the resin to the teeth. In many cases, to observe the tooth of interest, a health care provider uses a mouth mirror while applying the resin. When done, the health care provider switches instrument to a light cure, and illuminates the area for the resin to cure. When building up material on a tooth, the process repeats so that resin is applied, followed by curing, and then applied again, requiring to repeatedly switch the mouth mirror and light cure instruments.

During a typical patient visit to a dental office, a health care provider will record the patient's current dental status, also known as a dental tooth charting. A dental status, or dental tooth chart, is a diagram depicting the human teeth, where each tooth in the diagram is marked to indicate an aspect of the tooth's condition. In examples, a marking may indicate that a tooth is missing, has had dental treatment in the past, has a carious lesion, or has periodontal disease. Such status is updated from time to time to reflect the patient's most up to date condition. By inspecting the diagram, a health care provider (HCP) may become quickly informed about a patient's dental health status.

Like other medical professions, dentists need to track their work by recording and archiving with particularity a patient's dental condition and treatments. To facilitate such recording and archiving, computerized medical record systems exist. Generally, before adding or modifying data in an archive, a health care provider logs into the system to identify herself as the person providing the treatment. After logging in, the health care provider can select a patient record to retrieve information on file or to add additional information to the patient's record, such as a description of the current procedure, progress, and diagnoses for future treatment. The information in the patient's record is mostly text. Images might also be recorded, but the accompanying text is essential for the record. Therefore, the input regarding the treatment usually occurs at its end, when the professional is able to freely use the computer keyboard, both for convenience and for proper hygiene. Some of these computerized medical record systems include a digital version of a current status diagram, graphically depicting each tooth with a variety of marks and colors to represent various conditions.

Entering data into a patient's medical record takes time. However, in operating a dental office, efficiency is important. Less time spent on administrative tasks leaves more time for treatment. One of the hallmarks of a well-managed clinic is how efficiently time is used. As a result, some dentists, despite having implemented a computerized system as a management tool for their dental office, avoid the step of entering a textual description of the session to the system, and keep handwritten notes instead.

In dentistry (including orthodontics), multiple procedures exist that require generating a three-dimensional (3D) model of a patient's mouth. At present, many of these models are created using physical material, such as the routine use of plaster models. Recently, technologies and products have emerged for the creation of a digital representation of the 3D modeling, the models commonly called "digital impressions." These various products vary in the accuracy of the digital 3D model they achieve and in the amount of time that a dentist (or other dental health care provider) has to spend during the dedicated scanning session.

The general structure of 3D scanning machines consists of a scanning head, which performs intraoral measurements, from which depth measures can be extracted (calculated), and connected to a computer unit which processes the measurements to produce a digital model. The creation of a 3D imprint of the mouth is necessarily performed in a dedicated session, during a time period allocated specifically for this task.

The computing resources, such as processor and memory capacity, needed to produce an imprint are substantial. The acquisition of depth measurements is done in sections, the size of each of the sections is determined according to the amount of concurrent depth information that can be acquired by the scanning head. Then, generally, a 3D model of that section is calculated. Later, a registration of the various sections is performed, to allow the "stitching" of adjacent digitized regions into one consistent model. Additionally, if colors are acquired, a process of coloring and of possibly adding texture is performed. Additional processes might also be employed. The computer processing power required to produce such digital imprint in a reasonable amount of time is, therefore, substantial.

The technology implemented in the scanner head affects both accuracy and speed. The simplest of these, at least when being measured in terms of availability of electronic components, is a scanner head with an image capturing camera.

Several algorithms for extracting depth information from sets of images exist, involving identification of matching points or shading extraction or other concepts, followed by solving a so-called "triangulation problem".

In practice, achieving accurate depth measurements through image analysis in a short period of time is challenging since much of the information that is extracted from images tends to exhibit geometric noise, due to either distortion in the image capturing process, or uneven reflection of the illumination of intraoral objects. One of the reasons for the presence of such uneven illumination is that some areas may exhibit Lambertian reflection, while other areas exhibit specular reflection. The presence of saliva in an intraoral environment, is an additional, and sometimes substantial hurdle to the accuracy of the process, since it may cause some areas to exhibit specular reflection even if otherwise they would not. Using a multitude of captured images of an intraoral object from various angles, will greatly assist the triangulation accuracy, but unfortunately will extend the computational effort and hence the amount of time and processing power required for accurate calculation.

Systems and methods are needed to provide a more efficient way to show a patient images from the patient's mouth, to record the patient's dental status, and to create digital dental impressions.

BRIEF SUMMARY

Embodiments integrate a camera into an intraoral mirror. Integrating a camera into an intraoral mirror provides an efficient way to record and display what is visible to the healthcare provider in the mirror. In some embodiments, the images taken from the intraoral mirror are used to capture dental status and generate a digital dental impression.

In an embodiment, a method captures pictures in a patient's mouth. In the method, an image captured from an image sensor affixed to a dental mirror is received. The dental mirror has a plurality of light sources. A portion of the image is determined to be darker than another portion of the image. Based on which portion was determined to be darker, a light source is selected from the plurality of light sources such that it illuminates the portion more brightly than the other portion. The brightness of the selected light source is increased.

In another embodiment, a method controls power consumption of a dental instrument. An intraoral mirror is monitored to determine when it is not in use. The intraoral mirror includes an integrated camera. When the dental mirror is determined not to be in use, the intraoral mirror is put into a standby mode that reduces an amount of power consumed by the intraoral mirror.

Other system, method, and computer program product embodiments are also disclosed.

Further embodiments, features, and advantages of the invention, as well as the structure and operation of the various embodiments, are described in detail below with reference to accompanying drawings.

BRIEF DESCRIPTION OF THE DRAWINGS

The accompanying drawings, which are incorporated herein and form part of the specification, illustrate the present disclosure and, together with the description, further serve to explain the principles of the disclosure and to enable a person skilled in the relevant art to make and use the disclosure.

FIGS. 7A-C illustrate how dazzle is minimized.

The drawing in which an element first appears is typically indicated by the leftmost digit or digits in the corresponding reference number. In the drawings, like reference numbers may indicate identical or functionally similar elements.

DETAILED DESCRIPTION

The detailed description that follows is divided into ten sections. First, an intraoral mirror with an integrated camera is described with respect to FIGS. 1 and 2. Second, how the intraoral mirror is used as a viewfinder for the camera is described with respect to FIGS. 3, 4, 5A-C, 6A-B and FIGS. 7A-C. Third, systems and methods that utilize the intraoral mirror are described with respect to FIGS. 8-16. Fourth, how the intraoral mirror is used to capture a patient's dental status is described with respect to FIGS. 17A-C and 18A-C. Fifth, how the intraoral mirror is used to capture a patient's dental impression is described with respect to FIGS. 19A-B. Sixth, how the status and impressions are generated incrementally is described with respect to FIG. 20 and FIGS. 21A-B. Seventh, a system for capturing a patient's status and generating a patient's dental impression is described with respect FIG. 22. Eighth various methods for adjusting illumination of the intraoral mirror are described with respect to FIGS. 23 and 24. Ninth, a method for monitoring usage to conserve the intraoral mirror's power is described with respect FIG. 25. Tenth and finally, alternative embodiments of the intraoral mirror are described with respect to FIGS. 26-29.

A. Intraoral Mirror with Integrated Camera

Figure 1:
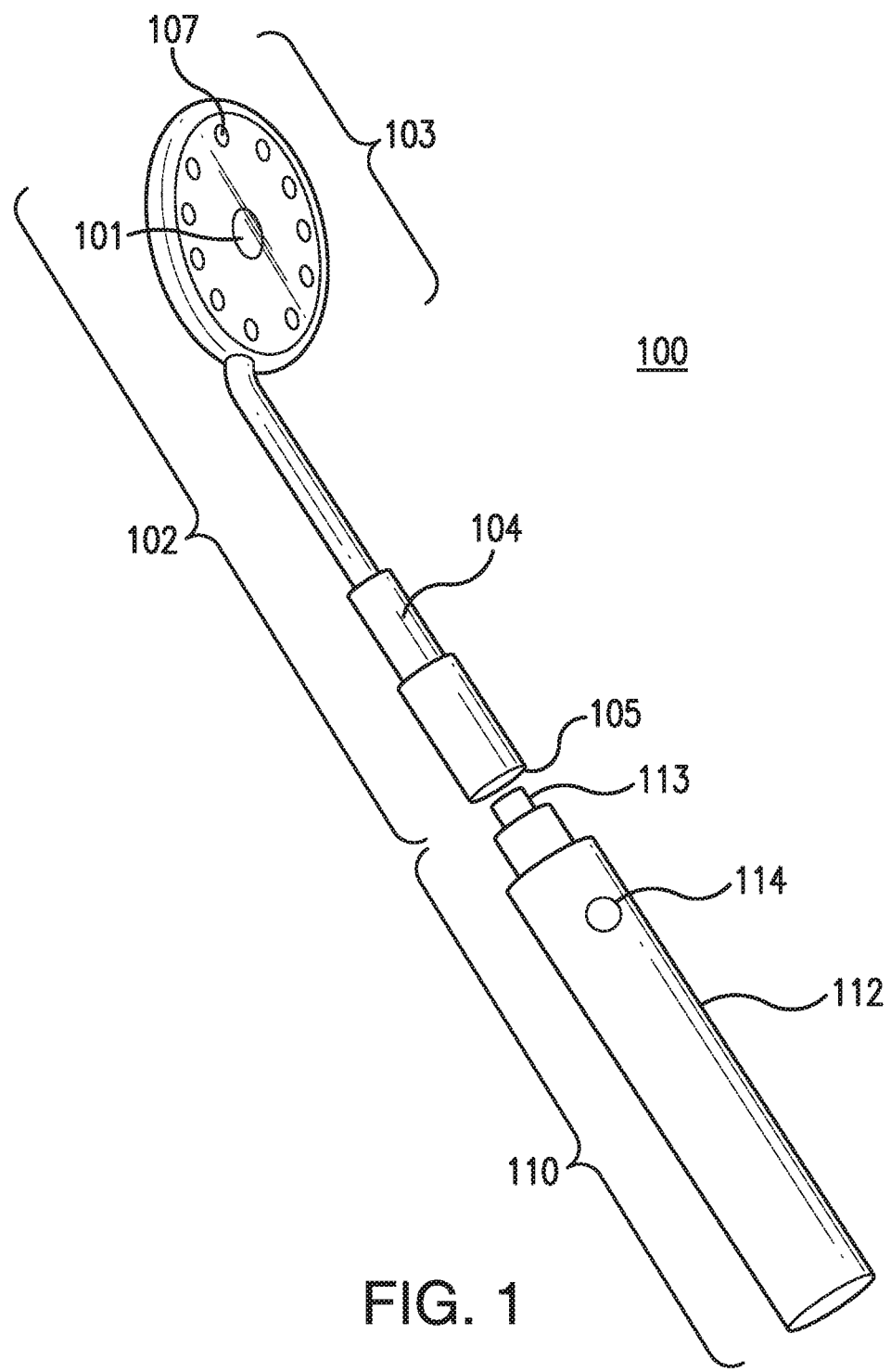
FIG. 1 is a diagram illustrating components of an intraoral mirror including an integrated camera, according to an embodiment.

FIG. 1 is a diagram illustrating components of an intraoral mirror including an integrated camera, referred to herein as a smart mirror device, according to an embodiment. In particular, FIG. 1 illustrates physical components of a smart mirror device 100.

Smart mirror device 100 includes two separate, detachable physical components: an oral piece 102 and a hand piece 110. The hand and oral pieces 102 and 110 may be further detachable into sub-pieces. Oral piece 102 may be the portion of smart mirror device 100 that can enter a patient's mouth. Oral piece 102 may include portions of the smart mirror device 100 that can be sterilized through being autoclaved. To be autoclaved, oral piece 102 can withstand being placed in an autoclave machine, which is a pressure chamber used to carry out industrial processes requiring elevated temperature and pressure different from ambient air pressure. Many autoclaves are used to sterilize equipment and supplies by subjecting them to high-pressure saturated steam at 121-132° C. (249-270° F.) for around 15-20 minutes depending on the size of the load and the contents. Additionally, oral piece 102 may be replaceable, for example if the reflective surface of viewfinder mirror 103 becomes damaged or due to an electronics component failure, which may occur as result of repeated use and sterilization.

In contrast to oral piece 102, hand piece 110 is not adapted to be in contact with a patient's mouth. Because hand piece 110 is not in contact with a patient's mouth, it may not need to be as sterile as oral piece 102. Hand piece 110 may include portions of the smart mirror device 100 that cannot withstand being autoclaved. For example, hand piece 110 may include sensitive electronics and a power supply that could be damaged by the heat, pressure, and moisture in an autoclave machine. Also, components may be placed on hand piece 110 as opposed to oral piece 102 to avoid the need to replace them as they become worn out through repeated use and sterilization.

Returning to oral piece 102, oral piece 102 includes a viewfinder mirror 103, an appendage 104, and a connector 105. Viewfinder mirror 103 is a mirror, hence has a reflective surface. Viewfinder mirror 103 may be round in shape. Viewfinder mirror 103's reflective surface includes a semi-reflective surface 101. Semi-reflective surface 101 appears reflective from the outside of the smart mirror device 100. But, from behind semi-reflective surface 101, surface 101 is transparent. In an embodiment, surface 101 is a transparent feature, small enough to enable a healthcare provider to have a clear view of the reflection when observing the reflective surface. Thus, behind semi-reflective surface 101, an image sensor (not shown) may be concealed. In one embodiment, viewfinder mirror 103 is round and semi-reflective surface 101 is located at the center of mirror. Viewfinder mirror image 103 provides visual guidance to a user about the objects that may be included in images captured by the sensor concealed behind surface 101. Hence, when smart mirror 100 is being used by a health care provider in an intraoral environment, the image sensor concealed behind surface 101 may capture images that include at least some of the objects whose reflection can be observed in the viewfinder mirror 103.

In addition to semi-reflective surface 101, viewfinder mirror 103 may also include a plurality of light sources 107. The light sources 107 are affixed around the perimeter of viewfinder mirror 103, and possibly concealed behind its reflective surface. Light source 107 may illuminate the intraoral environment. In some embodiments, light source 107 illuminates in the visible light spectrum, for example a light of similar color hues of daylight, which enables a visual perception (as well as capturing of images) of natural colors, or maybe a so-called "warm white" color which in some cases produces an illumination which is more comfortable to the human eye. In some embodiments, light source 107 illuminates in non-visible radiation, for example in a frequency within the infrared spectrum.

Appendage 104 is affixed to viewfinder mirror 103, protecting hand piece 110 from contacting the intraoral environment while allowing for comfortable intraoral use of viewfinder mirror 103. Appendage 104 has an elongated shape with viewfinder mirror 103 affixed to one end of the shape, extending viewfinder mirror 103 into the patient's mouth. In some embodiments, appendage 104 has a shape of a tube or cylinder, but other shapes, including those with non-rounded cross-sections, are possible. In some embodiments, at least part of appendage 104 is hollow, allowing space for electronic components. In some embodiments, electronic components are located elsewhere, the invention is not so limited.

While one end of appendage 104 is affixed to viewfinder mirror 103, the opposite end is affixed to a connector 105. Connector 105 is a physical and electrical connector to connect oral piece 102 with hand piece 110. In some embodiments, connector 105 is internal to appendage 104. For example, hand piece 110 can slide or partially slide into a hollow part of appendage 104 to attach hand piece 110 with connector 105. An impermeable lid (not shown) may be used to seal off connector 105 when oral piece 102 is autoclaved. Appendage 104 may interlock with hand piece 110 to avoid separation of oral piece 102 and hand piece 110 during use of smart mirror 100. To interlock with hand piece 110, the two pieces may, for example, screw into one another, or pressure from hand piece 110 sliding into appendage 104 may hold the two pieces together during use.

As mentioned above, hand piece 110 may include components that are not capable of being autoclaved. Thus, oral piece 102 may be detached from hand piece 110 so that it can be autoclaved. Hand piece 110 includes a connector 113, a handle 112 and a button 114. Connector 113 is adapted to couple with connector 105 of oral piece 102. The coupling may be electrical. For example, connector 113 may supply power to oral piece 102 through connector 105. In addition, hand piece 110 and oral piece 102 may transmit and receive data from one another via connectors 113 and 105.

Handle 112 enables a health care provider to grasp smart mirror device 100. Like appendage 104, handle 112 may have an elongated shape, such as a cylinder, and may be hollow on the inside to conceal electronic components. For example, handle 112 may conceal a power supply, a processor, and accelerometer or gyroscope. On handle 112 is button 114, which accepts input from the health care provider. In some embodiments, handle 112 is completely covered by appendage 104, so a health care provider does not literally grasp it when smart mirror device 100 is in use.

Figure 2:
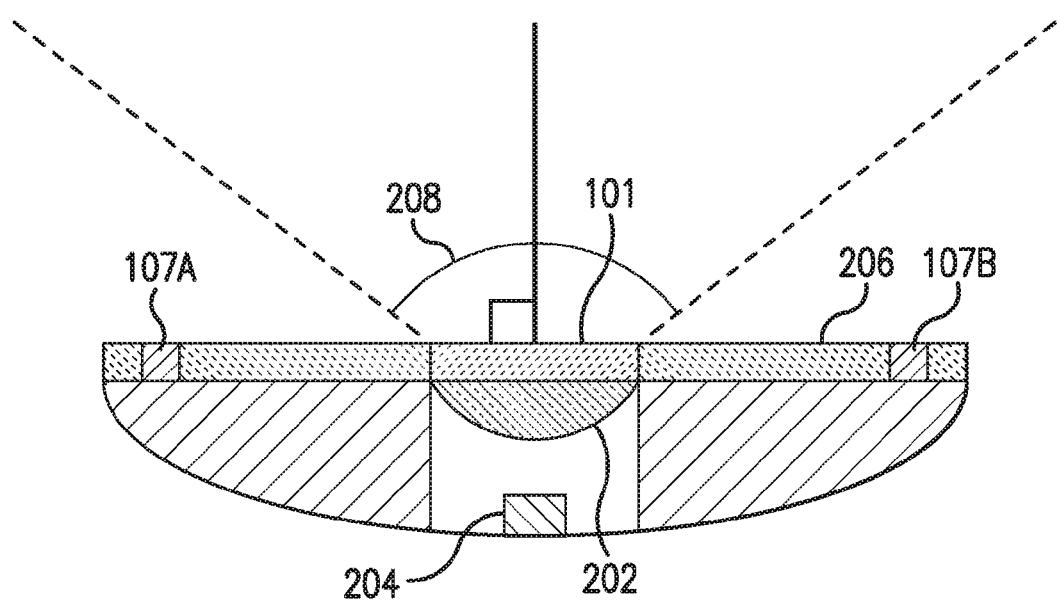
FIG. 2 is a diagram illustrating a cross-section of a mirror portion of the intraoral mirror.

FIG. 2 is a diagram illustrating a cross-section of viewfinder mirror 103 of the smart mirror device 100 shown in FIG. 1. Viewfinder mirror 103 includes a mirror surface 206 that reflects light into the healthcare provider's field of view. As mentioned above for FIG. 1, mirror surface 206 comprises partially reflective surface 101, which is configured such that one side appears reflective to a health care provider and that another side is transparent to an image sensor 204. Also as mentioned above for FIG. 1, around a perimeter of mirror surface 206 may be a plurality of light sources 107A-107B. Light sources 107 may be illumination devices, such as light emitting diodes. Like image sensor 204, light sources 107 may be situated behind a partially reflective surface (not shown).

Situated between image sensor 204 and partially reflective surface 101 is a lens 202. Lens 202 may refract light to image sensor 204 from a field of view 208. Lens 202's field of view 208 has a viewing angle that is wide enough to simultaneously capture both part of a face of a health care provider and a portion of a patient's mouth that is visible to the health care provider in most intraoral usage conditions.

In various embodiments, the viewfinder mirror 103 may have several lenses. The multiple lenses may move or adjust to allow focus at different distances. There may be a mechanism for autofocus or a mechanism to add or remove one or more lenses between the mirror surface and the sensor.

In additional embodiments, light from surface 101 may be split to multiple structures of lenses and sensors. In addition, the light from surface 101 may be folded before it reaches an image sensor 204 using a prism. As will be discussed below, the image sensor 204 may be located in an appendage or hand piece.

B. Using an Intraoral Mirror as a Viewfinder

Figure 3:
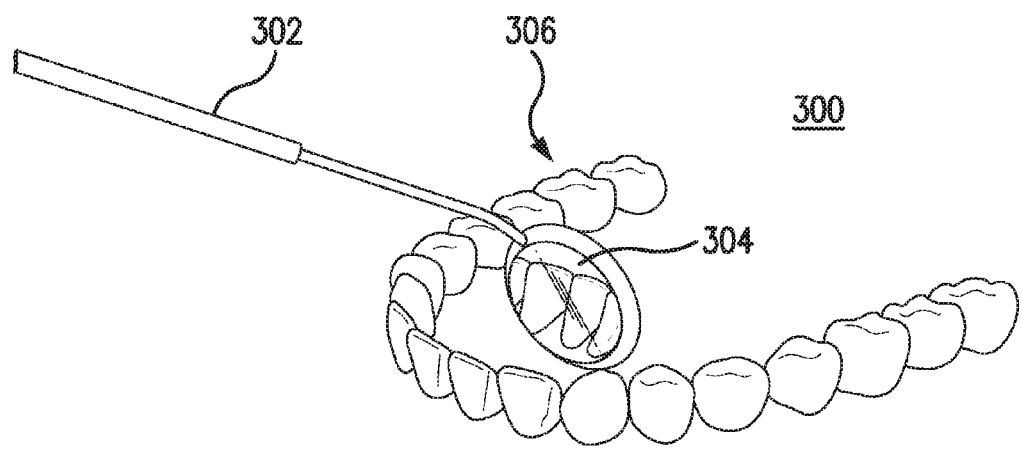
FIG. 3 is diagram illustrating an intraoral mirror being used to examine a patient's mouth from the perspective of a healthcare provider.

FIG. 3 shows diagram 300 illustrating an intraoral mirror being used to examine a patient's mouth from the perspective of a healthcare provider. In particular, diagram 300 includes smart mirror device 302 having a mirror surface 304. In diagram 300, smart mirror device 302 is being used to inspect teeth 306. In diagram 300, mirror surface 304 is positioned to show the lingual surface of teeth 306 (the back of the tooth) from the healthcare provider's perspective. Notably, what is visible from the healthcare provider's perspective may differ from what is visible from the image sensor's perspective. This is illustrated, for example, in FIG. 4.

Figure 4:
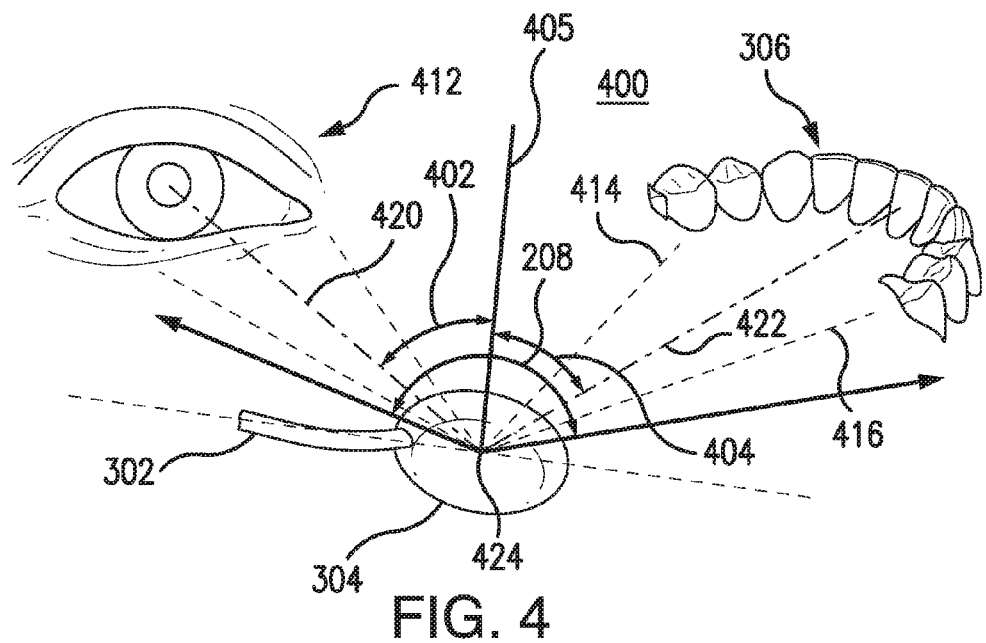
FIG. 4 is a diagram illustrating how light from the patient's mouth is reflected off the mirror's reflective surface and observed by a healthcare provider.

FIG. 4 shows a diagram 400 illustrating how light from a patient's mouth is reflected off a mirror's reflective surface and observed by a healthcare provider. Diagram 400 shows how smart mirror device 302's mirror surface 304 reflects light from the lingual surface of teeth 306 to an eye of a healthcare provider 412. In particular, a plurality of rays of light spanning from ray 414 to ray 416 travel from teeth 306 to mirror surface 304. Each of the rays, which we shall call incident rays, reach mirror surface 304 at an incidence angle, for example ray 422 at incidence angle 404. Then, according to the so-called "law of reflection", the rays are reflected from the mirror surface 304 so that each reflected ray, the respective incident ray and the normal to the surface at the incidence point (labeled incidence point 424) are all on the same plane. Moreover, the angle of reflection is equal to the angle of incidence. The combination of reflected rays that happen to reflect toward the healthcare provider 412 define what is being observed in the mirror. For example, incident ray 422 reaches the mirror surface 304 at an incidence point on mirror surface 304 and at an incidence angle 404 and its reflected ray 420 towards the healthcare provider 412 is at a reflection angle 402 which is equal to the incidence angle 404. Thus, the lingual surface of teeth 306 is visible to healthcare provider 412, and health care provider 412 observes the perspective illustrated in FIG. 3.

As described above for FIG. 2, smart mirror device 302 includes an image sensor, and the image sensor captures light refracted by a lens with field of view 208. As illustrated in diagram 400, field of view 208 is wide enough to capture the lingual surface of teeth 306, which is visible to healthcare provider 412 on mirror surface 304, even in cases were healthcare provider 412 is focusing on incidence points off the center of the mirror. Thus a health care provider may use a smart mirror device 302 to capture image snapshots without interrupting treatment by switching to a separate intraoral camera instrument. Nonetheless, the captured image must be processed so that the result fits what healthcare provider 412 observes in the mirror surface 304. This processing is required because the orientation of an intraoral mirror may change as a healthcare provider rotates it and also because possibly more is visible to the image sensor in smart mirror device 302 than is visible to healthcare provider 412, for example, field of view 208 is wide enough to capture part of the face of health care provider 412, while health care provider 412 may not witness his reflection in mirror surface 304. Therefore, in order to improve the use of the intraoral mirror as a viewfinder, the portion of an image captured by the image sensor that is being observed by the healthcare provider 412 must be determined.

To determine which portion of field of view 208 is being observed by healthcare provider 412, healthcare provider 412's face may be detected in the image captured by image sensor. Then, following the law of reflection, only backwards, a ray 420 extended from health care provider 412 toward an incidence point of the mirror is determined. Ray 420 may have an angle 402. While diagram 400 only identifies the angle of incidence and reflection for a ray 420 and a ray 420 on a plane for clarity and simplicity, a skilled artisan would recognize that the geometry is three-dimensional, and the drawing describes the angles for these rays on the plane of incidence, which is perpendicular to the reflective surface at point of incidence 424. Based on ray 420, a ray 422 extended from the mirror surface toward an object appearing to the health care provider on the mirror surface is determined. Ray 422 is determined by having an angle 404 equal to angle 402. An incidence point 424 that corresponds to healthcare provider's 412 center of gaze defines the center of the portion of interest out of field of view 208. The center of gaze may be determined by eye tracking methods. A reasonable approximation is to assume that healthcare provider 412 is observing an object at the center of the mirror.

Figure 6A:
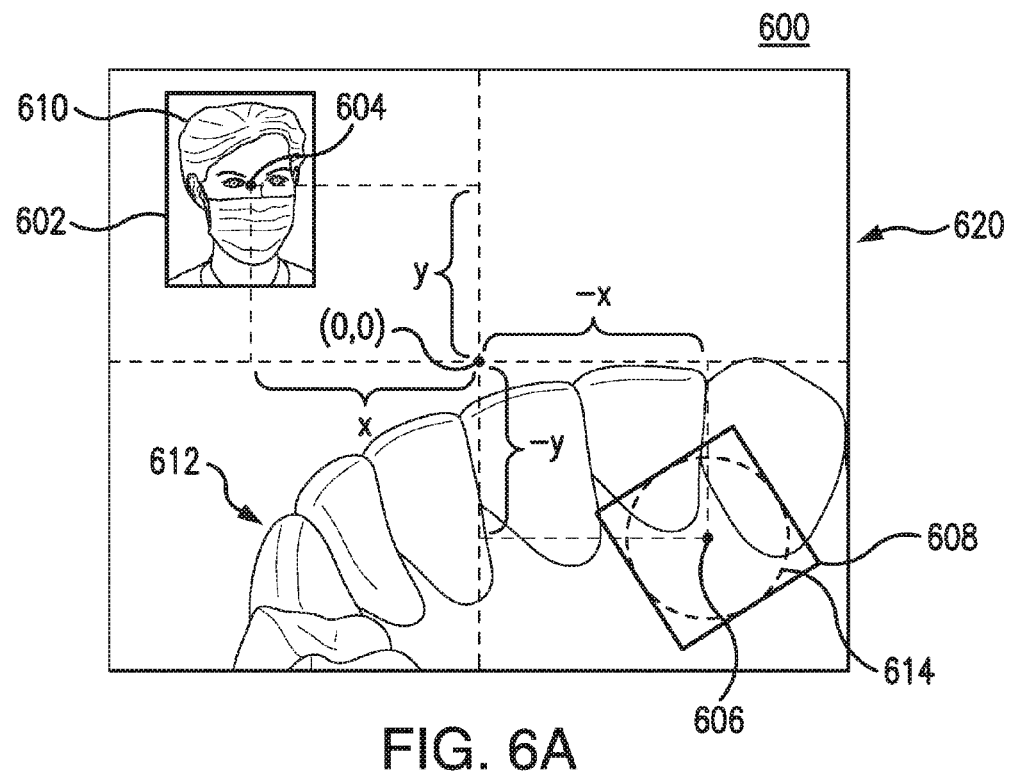
FIG. 6A illustrates how the portion of an image captured by a wide-angle camera that is visible to a healthcare provider on the reflective surface of the intraoral mirror is determined.

There are various ways to conduct the calculation above. One way to approximate the calculation is illustrated in FIG. 6A. FIG. 6A shows a diagram 600 illustrating image 620 captured from an image sensor in a smart mirror device. Image 620 includes teeth 612 and a healthcare provider's face 610. A skilled artisan would recognize that, given the orientation of the smart mirror device in FIG. 3, the image actually captured from the image sensor may be rotated from what is presented in image 620.

A face detection algorithm may be applied to identify which portion of the image includes the healthcare provider's face 610. The algorithm may further be specified to identify not only the healthcare provider's face, but more specific to identify only the healthcare provider's eyes. In diagram 600, the algorithm detects a face in a region 602, which has a center point 604.

An origin having coordinate point (0,0) is determined at the center of the image. This may be the point where light that is normal to the center of the mirror surface is captured. Center point 604 may be determined relative to the origin as an (X, Y) coordinate. An example, the X and Y values could be the pixel values relative to the origin. The X and Y distance may be expressed in other ways as well.

Next, a point 606 in image 620 is determined as a point having the inverse coordinate (−X, −Y). Point 606 may be the center of the portion that is determined to be visible by the healthcare provider. With point 606 at the center, a region 608 is determined. Region 608 should be determined such that it includes a portion 614 of image 620, which is visible on the mirror surface. The size of region 608 may be fixed in accordance with the mirror size or the target display. Alternatively, it may be adjusted according to a distance between an object being viewed and the mirror surface, or the amount of relevant information in the image.

The orientation of objects as they appear in region 608 depends on the orientation of objects as they appear in image 620, the orientation of objects as they appear in image 620 depends on the orientation of the image sensor, and the orientation of the image sensor depends on the orientation of the smart mirror device. A healthcare provider holds the smart mirror device at an angle relative to the object being observed. The angle is subject to variation as it changes among observations of different objects and possibly also of the same object. A healthcare provider looking at the reflection of an image may change the angle to accommodate better viewing. To such an observer, a slight change in mirror position or angle may not significantly alter the view of an object in the mouth.

Conversely, for an image capturing device at the center of said mirror, the image being captured may dramatically change following even small changes to the angle, causing changes to the size and location in the image of the object being observed in the mirror, such as a tooth, that might be in close proximity to the intraoral mirror. The visual information captured in the image will change when the angle changes.

A round mirror reflecting an object may rotate around its center, and to the observer there will be no apparent change in the reflection. The human interpretation of the reflection has a natural orientation, generally upwards. Conversely, for an image capture device at the center of said mirror, a change in rotation also changes the direction that the image sensor considers "upwards." Therefore, the image being captured might appear substantially different than the image observed in the mirror, possibly hampering the use of said mirror as a viewfinder for image capture.

To deal with these issues, the smarter device may include an orientation measuring device, such as a gyroscope, that collects data to determine an orientation of the dental instrument. Based on the information collected from the gyroscope, the image may be reoriented, as illustrated FIGS. 5A-C and FIG. 6B.

Figure 5A:
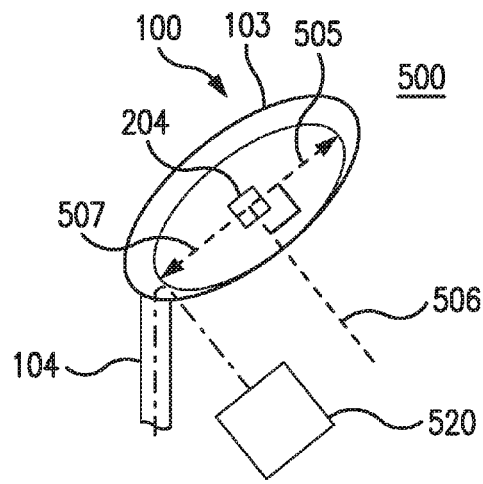
FIGS. 5A-C are diagrams illustrating how an orientation of an intraoral mirror may change as a healthcare provider rotates it.
Figure 5B:
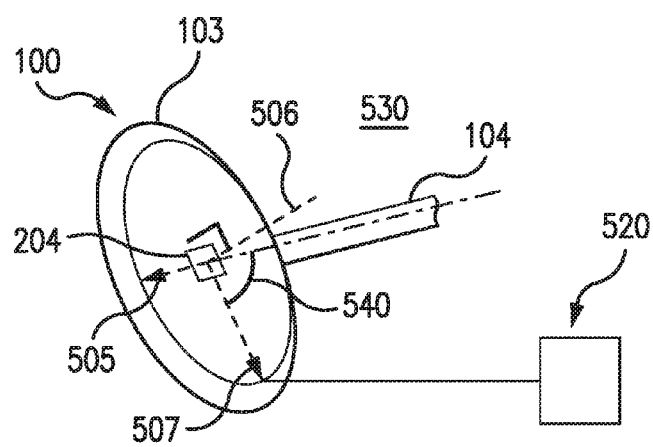
Figure 5C:
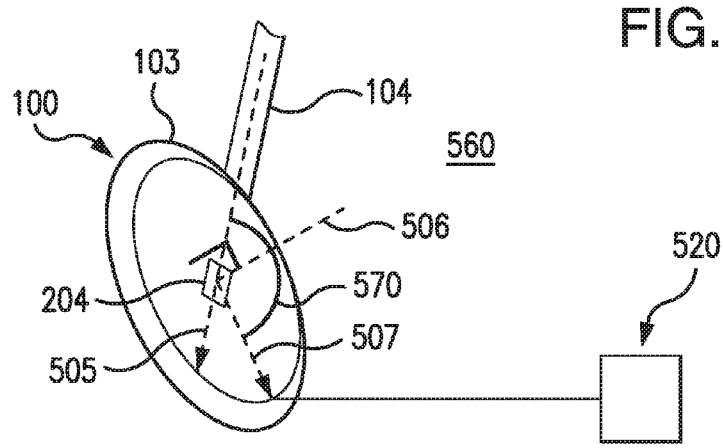

FIGS. 5A-C are diagrams illustrating how an orientation of an intraoral mirror may change as a healthcare provider rotates it. FIG. 5A shows a diagram 500 illustrating the geometry of the problem being addressed by this invention. Diagram 500 illustrates a portion of smart mirror device 100 described in FIG. 1 including viewfinder mirror 103 and appendage 104, which includes or is connected to a handle that the healthcare provider uses to grasp a mirror. Viewfinder mirror 103 is coupled to an image sensor 204.

In diagram 500, smart mirror device 100 may be placed vertically at an initial position. In an embodiment, the initial position may be in a cradle on a charging station, where the orientation of the device is known. Because smart mirror device 100 is vertical, an axis 505 which coincides with a diameter running from the top of smart mirror device 100 through the center of viewfinder mirror 103 and towards the handle is known to face straight up-and-down. From here, the orientation measuring device may be calibrated. Downward projection 507 may be indicated as down toward appendage 104. In this orientation, the image sensor 204 may be oriented such that when it captures an image of an object 520, object 520 appears at the bottom of the captured image.

In diagram 500, a normal 506 is perpendicular to viewfinder mirror 103 at its center, which, according to an embodiment, is where image sensor 204 is located. The normal 506 points to the direction that the image capture sensor 204 is pointing, so that when capturing an image, an object located in the direction of normal 506 will appear at the center of the image.

FIG. 5B and FIG. 5C show diagrams depicting how smart mirror device 100 in FIG. 5A can change orientation with respect to an object 520.

FIG. 5B shows how smart mirror device 100 is rotated around normal 506. As shown in FIG. 5B, object 520 appears at a different location with respect to image sensor 204. Without correction, object 520 may appear in an awkward location in the resulting image captured from image sensor 204.

To correct for the location of object 520, any images collected from image sensor 204 may be rotated by an angle 540 between line 507 and axis 505 to ensure that line 507 continues to project downward. Angle 540 may be the azimuth angle around normal 506 between axis 505 and downward projection 507.

As mentioned above, angle 540 may be sensed by an orientation measuring device in smart mirror device 100. As mentioned above, the orientation measuring device may be a gyroscope able measure changes in yaw, pitch, and roll of smart mirror device 100. By integrating those changes, orientation measuring device can determine the yaw, pitch, and roll angles of smart mirror device 100. Depending on the position of the gyroscope within smart mirror device 100, the roll angle may be set to, or at least used to determine, angle 540 between axis 505 and downward projection 507.

FIG. 5C is a diagram 560 showing smart mirror device 100 being further rotated. As smart mirror device 100 is further rotated, the orientation measuring device senses that smart mirror device 100 has been rolled further and determines that the angle between axis 505 and downward projection 507 is greater, illustrated in diagram 560 as azimuth angle 570. Based on this azimuth angle, the image captured from image sensor 204 is rotated. In particular, the image captured from image sensor 204 (or at least a portion thereof) is rotated by the roll calculated based on measurements by the orientation measuring device—angle 540 in FIG. 5B or angle 570 in FIG. 5C. This is illustrated, for example, in FIG. 6B.

Figure 6B:
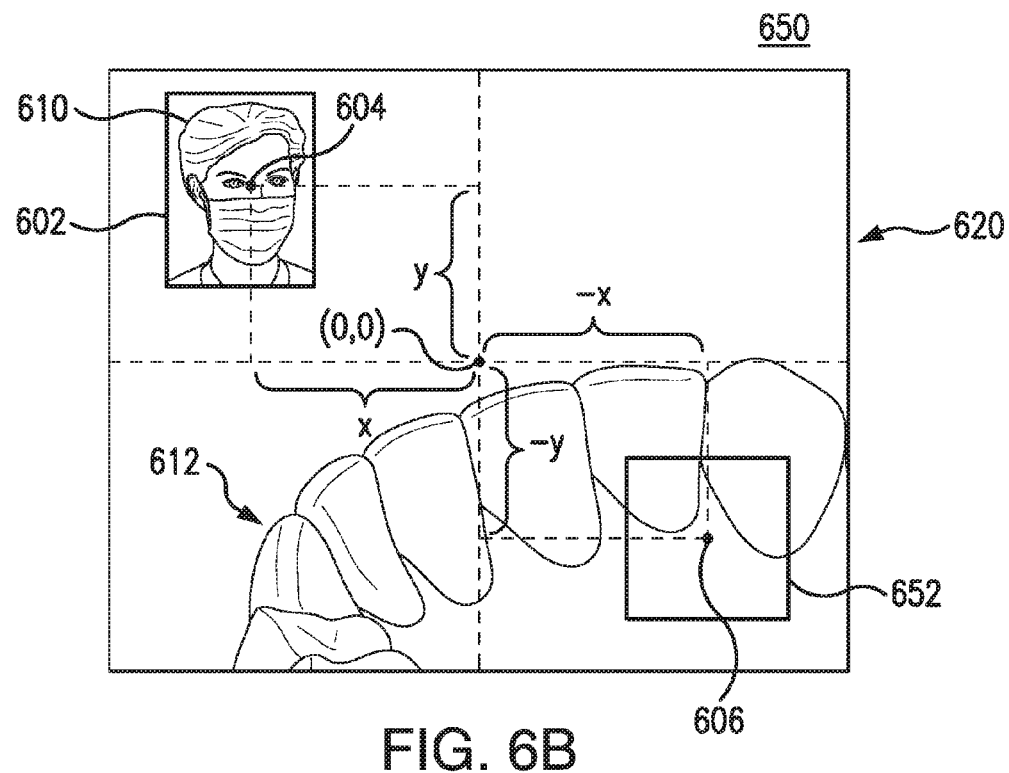
FIG. 6B illustrates how the portion determined to be visible to the healthcare provider is rotated to adjust for rotation of the intraoral mirror.

FIG. 6B shows a diagram 650 illustrating how the region identified as being visible to a healthcare provider in a mirror is rotated. Similar to diagram 600 in FIG. 6A, diagram 650 shows an image 620 taken from the perspective of a smart mirror image sensor. Image 620 again includes healthcare provider 610 and teeth 612. Once again, in diagram 600, a region 608 is determined corresponding to what is visible to healthcare provider 610 on the mirror surface. In this illustration also shown the region as is rotated according to the way health care provider 610 holds the smart mirror device. Once region 608 is determined, it is rotated around its center by the azimuth angle determined by the smart mirror's orientation measuring device to produce what is illustrated in diagram 650 as region 652. Region 652 may be cropped from the image and identified as the image visible to healthcare provider 610 on the smart mirror's surface.

In this way, by detecting a face in an image captured by a smart mirror device's image sensor and by detecting the smart mirror device's orientation, a portion of the image captured by the smart mirror device's image sensor that corresponds to what is visible to the healthcare provider on the mirror surface can be determined, thus determining the portion visible on the mirror surface from a larger field of view.

Back to FIG. 3, a smart mirror device 302 also illuminates the patient's mouth. Such illumination improves the view of the mouth to a healthcare provider and also enables enough light to arrive to the image sensor for capturing clearer images. However, when gazing at the mirror while inspecting a patient's mouth, some of the light sources 107 might be visible to the healthcare provider, possibly disturbing his vision by dazzling (i.e., glare). Therefore, to improve the use of the intraoral mirror as a viewfinder, which lights sources out of the light sources 107 of a smart mirror 302 should be lit and which should not be lit must be determined.

To determine which of light sources 107 should be lit and which should not be lit, healthcare provider's face may be detected in the image captured by the image sensor. Referring to FIG. 6A, in image 620 the distance between center point 604 and the center of the image at (0,0) represents the angle between a normal to the mirror at its center and the direction towards the healthcare provider's face. Accordingly, light sources 107 that may emit light in that direction may be turned off to avoid dazzling. The angle of the direction may be spherical.

Another method to determine which of light sources 107 should be lit and which should not be lit is to find out the parts, or segments, of image 620 that contain intra-oral objects. One way to do this is to compare two images taken at the same position but with different illuminations, for example, one with all of light sources 107 turned on and the second with all of light sources 107 turned off. Due to the so-called "inverse square law", stating that the intensity of illumination is inversely proportional to the square of the distance from the light source, the effect of turning on the illumination on the closer intra-oral objects will be substantial, while the effect on farther, extra-oral objects will be much smaller if noticeable at all. Therefore the image may be segmented into intra and extra-oral sections by analyzing this difference. Similarly, even when some of light sources 107 are turned on, the use or addition of a colored light could be used, for example alternating the illumination of a green or blue light and comparing the effect on different images may be used to generate such segmentation, or even a light of a frequency not visible to the human eye, such as infrared, may be used.

Another method to find out the segments of image 620 that contain intra-oral objects is by usage of image processing and analysis techniques. For example by filtering colors in order to locate teeth, or by finding the occlusal edge of the teeth, locating the separation line between intra- and extra-oral.

Lastly, a simpler segmentation may be performed using the orientation of the smart mirror. Particularly, by evaluating the angle between an horizontal plane, parallel to the room's floor, and the normal to the surface of the mirror at its center, and determining to turn on a upwards or downwards illumination based on a threshold. For example, above 20 degrees, select downward illumination, thus illuminating objects in the lower section of the mirror, and below 20 degrees select upward illumination, illuminating objects in the upper section. Additionally, the selection of which light sources to be lit also depend on the rotation of the mirror around its center, as this value determines which light sources are upward and which are downward.

Figure 7C:
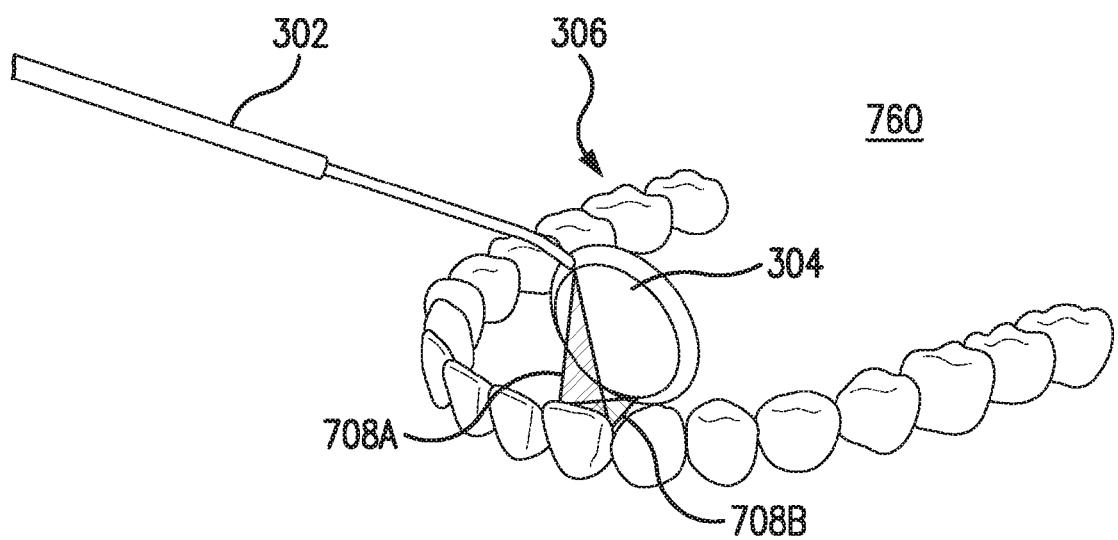

Once the segment that requires illumination is determined, light sources 107 that emit light in the direction of objects included in the segment may be turned on, and light sources 107 that emit light outside the segment may be turned off, as illustrated in FIGS. 7A-C.

FIG. 7A illustrates a diagram 700 with viewfinder mirror 103 including a plurality of light sources 107A-B. Light sources 107A-B may emit light at a first angle. In diagram 700, viewfinder mirror 103 also includes a plurality of light sources 707A-B, which emit light at a second angle, different from the first angle. In addition, the angles may be variable. Actuators (not shown) in viewfinder mirror 103 may enable respective light sources 107 and 707 to emit light in a variety of angles. Whether fixed or variable, having different light sources at different angles enables the device to select the direction of the light emitted. And by selecting the direction of the light emitted, the smart mirror device may direct the light to illuminate the object of interest and to avoid shining light toward the health care provider, dazzling her.

To illuminate an object of interest, various beams of light emitted from different light sources 107A-B or 707A-B may converge at the object. In diagram 700, light source 707A and light source 107B are selected to illuminate an object 702. A beam of light 708A is emitted from light source 707A and a beam of light 708B is emitted from light source 107B. Both beams converge at object 702.

Similarly, FIG. 7B shows a diagram 730 that illustrates light source 107A and light source 707B being selected to illuminate an object 732. A beam of light 738A is emitted from light source 107A and a beam of light 738B is emitted from light source 707B. Again, both beams converge at object 732.

As described above, the object 702 and 732 may be determined various techniques, including face detection and image processing techniques. In this way, by selecting the direction of light to illuminate the portion of the image determined to contain the object of interest, embodiment can illuminate the portion of the image sensor's field of view visible to the health care provider, as illustrated in diagram 760 in FIG. 7C.

C. Systems and Methods Utilizing the Intraoral Mirror

As discussed above, embodiments provide for a camera to be integrated onto an intraoral mirror and enable the mirror to act as a viewfinder for the camera. Now, various systems and methods that utilize the intraoral mirror are described.

Figure 8A:
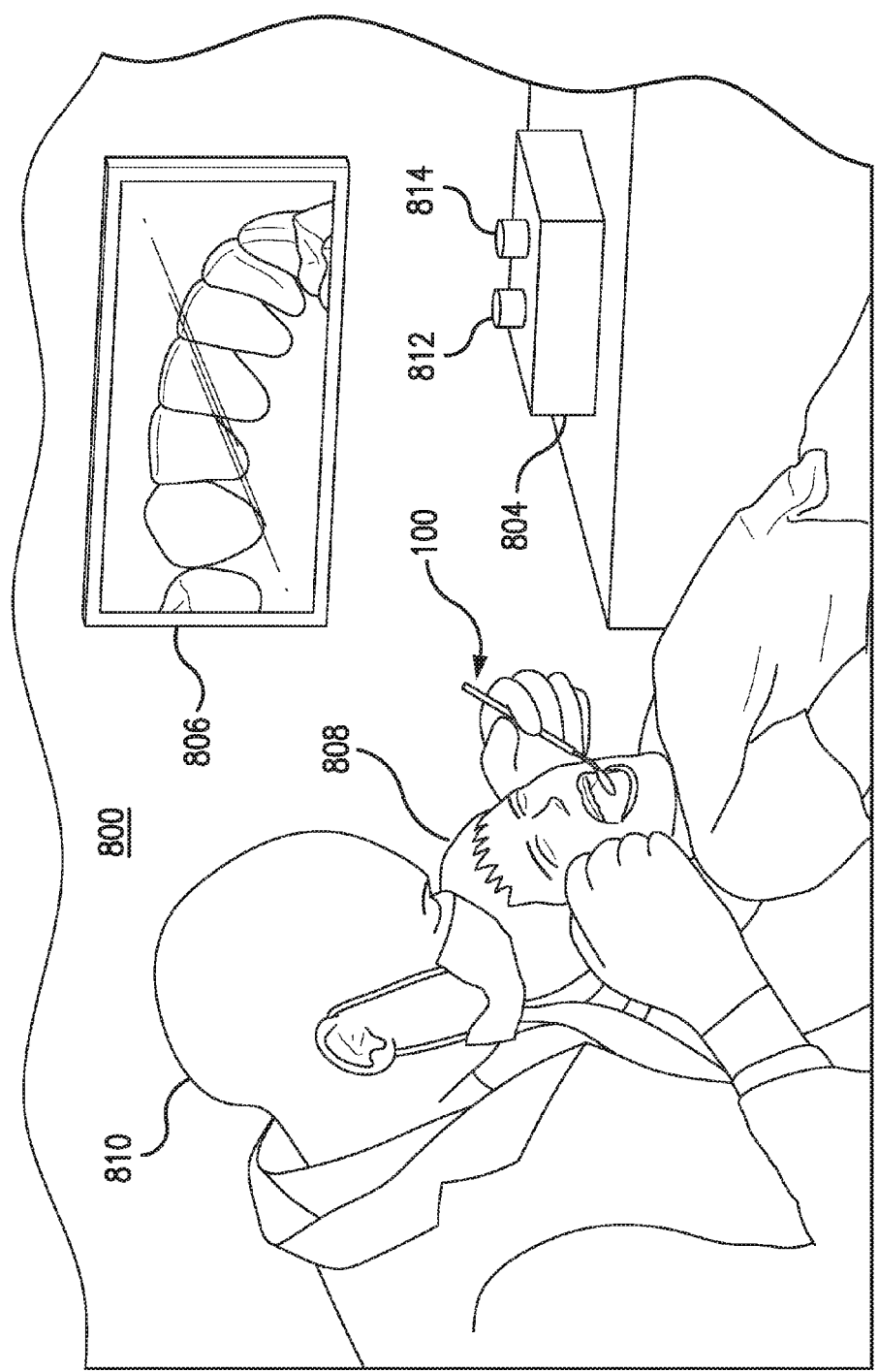
FIG. 8A illustrates a room of a dentist office including a system for displaying what is apparent to the healthcare provider in an intraoral mirror.

FIG. 8A illustrates a room 800 of a dental office including a system for displaying what is apparent to the healthcare provider in an intraoral mirror. Room 800 shows a healthcare provider 810 utilizing smart mirror device 100 to examine a patient 808. Tablet 806 shows what is visible to the doctor in smart mirror device 100. Also inside room 800 is a base station 804. Base station 804 includes cradles 812 and 814. Base station 804 allows multiple smart mirrors (not shown) to be used in the same room 800. For example, an assistant may use one mirror on a patient while a dentist uses another on the same patient. Base station 804 includes multiple cradles to allow multiple smart mirrors to dock.

Once healthcare provider 810 is no longer using smart mirror device 100, he may place it on one of cradles 812 and 814. When smart mirror device 100 is docked with cradles 812 or 814, base station 804 may charge smart mirror device 100. Also, as described above, when docked with cradles 812 or 814, smart mirror device 100 may calibrate its gyroscope and accelerometer.

Base station 804 also provides for communication with smart mirror device 100. In particular, smart mirror device 100 transmits images and other information to base station 804, which transmits the information for display on tablet 806. The communication paths are illustrated in FIG. 8B.

Figure 8B:
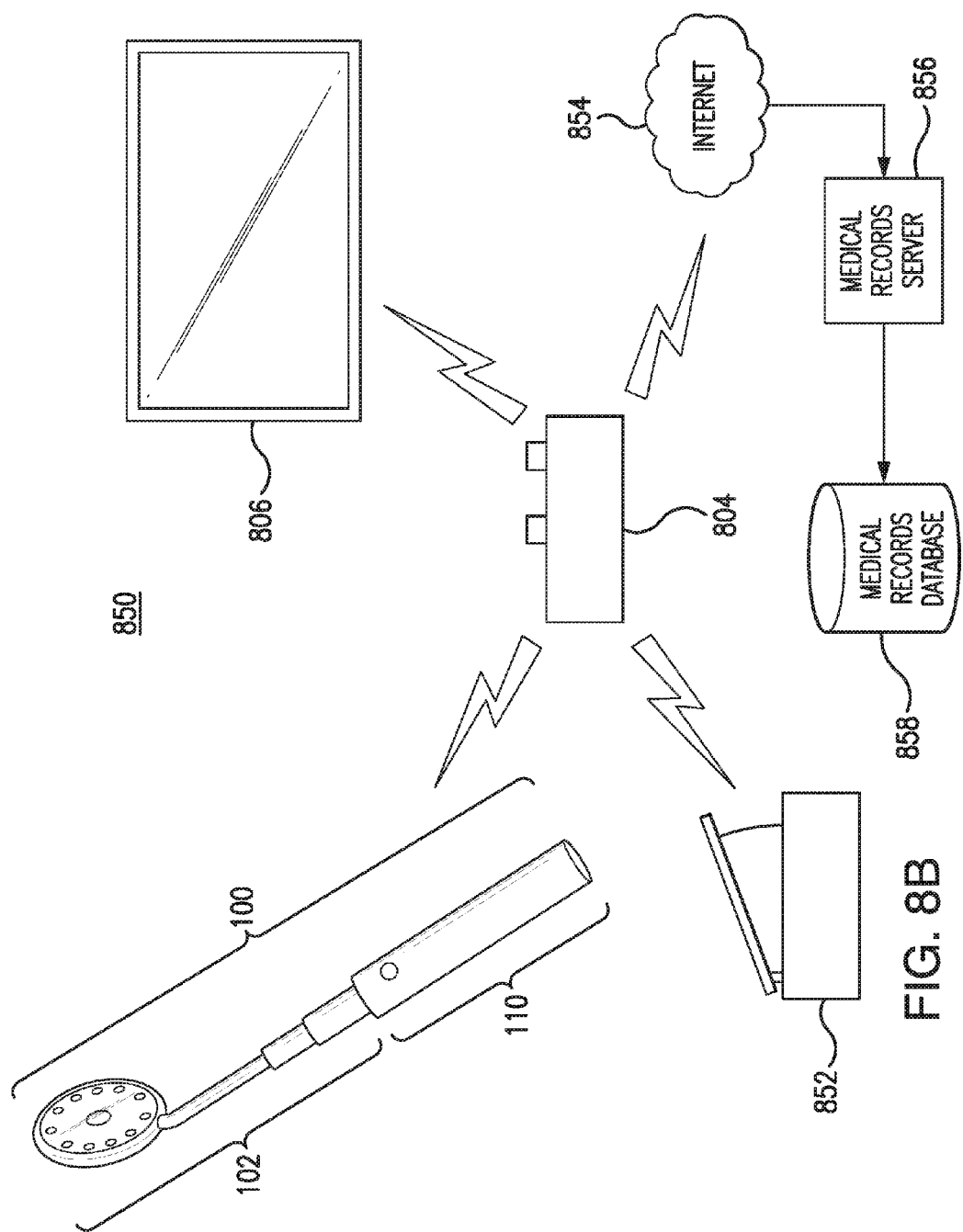
FIG. 8B is an architecture diagram of the system in FIG. 8A.

FIG. 8B is an architecture diagram 850 of the system in FIG. 8A. In addition to the components in FIG. 8A, diagram 850 shows a foot pedal 852, a medical records server 856, and a medical records database 858.

Smart mirror device 100, tablet 806, and foot pedal 852 may be connected using a wireless connection, such as Wi-Fi. In particular, base station 804 may act as a Wi-Fi router and provide network routing and address information to smart mirror device 100, tablet 806, and foot pedal 852.

Foot pedal 852 provides a way for the healthcare provider to input information in a hands-free manner. For example, to request the capturing of an image snapshot or a video clip. In one embodiment, smart mirror device 100 may include a microphone, and the healthcare provider may indicate when he would like to record information from the microphone by depressing foot pedal 852.

Base station 804 is connected to medical records server 856 via one or more networks 854, such as the Internet. Base station 804 may be connected to the Internet either through a wireless or wired LAN in the dental office. Server 856 is a computerized process adapted to run in one or more remote server computers. Server 856 may, for example, be a cloud server. Server 856 is further connected to an archival medical records database 858. Medical records database 858 stores medical record information, including dental status information collected from smart mirror device 100.

Figure 9:
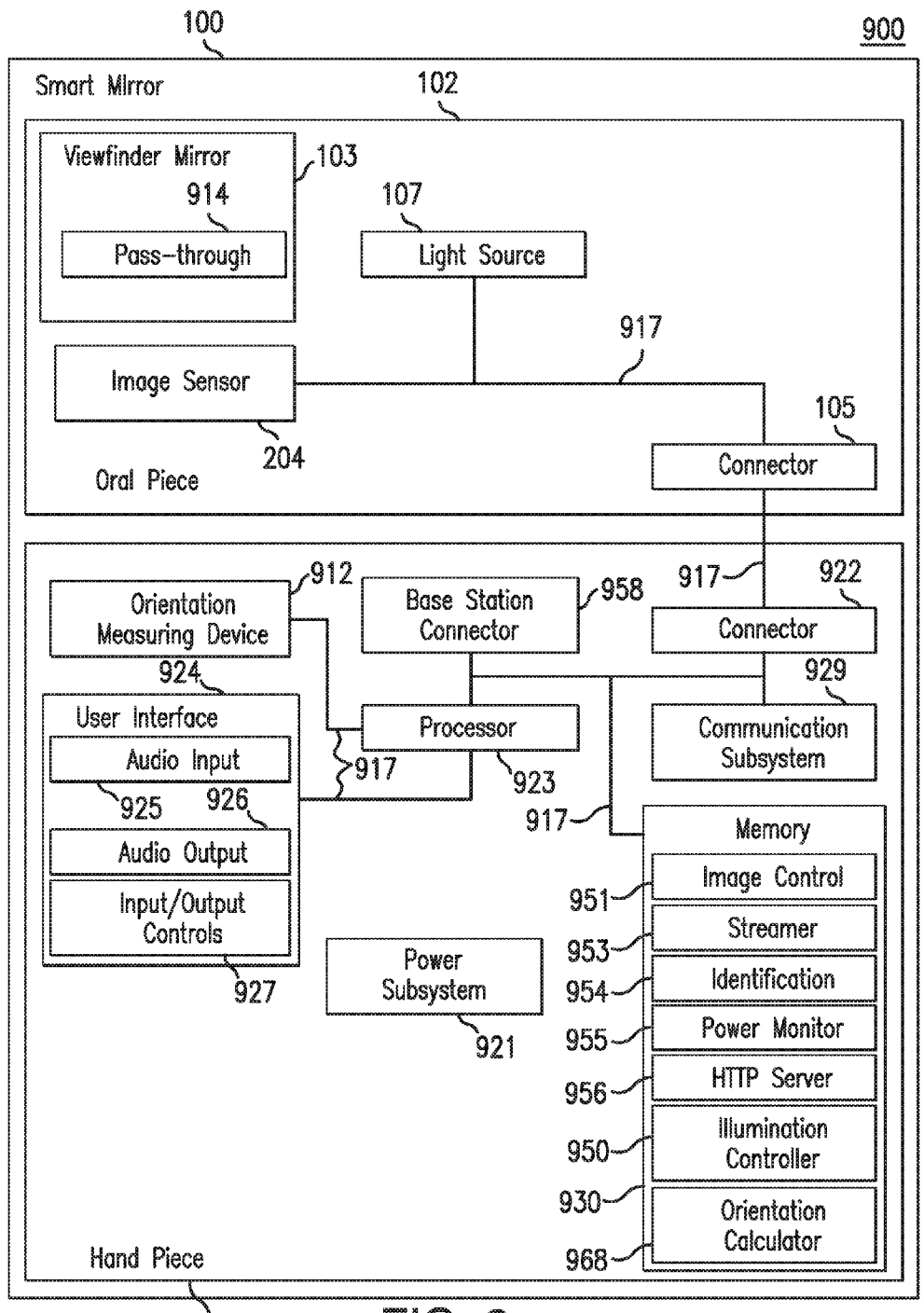
FIG. 9 is a block diagram of the intraoral mirror including an integrated camera.

FIG. 9 is a block diagram 900 illustrating a possible configuration of smart mirror device 100. As discussed above, smart mirror device 100 has two separable components, oral piece 102 and hand piece 110, and oral piece 102 includes viewfinder mirror 103, image sensor 204, light source(s) 107, and a connector 105.

It may be appreciated for those skilled in the art that a plurality of signal lines or buses 917 may exist, thus different components may be linked by different signal lines or buses 917, and that a signal lines or buses 917 depicted in the schematic diagram may represent a plurality of such.

As discussed above for FIG. 1, viewfinder mirror 103 is a mirror, thus having a reflective area. The reflection from viewfinder mirror 103 provides visual guidance to a user about the objects that may be included in images captured by image sensor 204. As mentioned above, viewfinder mirror 103 may be round. In some embodiments, viewfinder mirror 103 is planar. In some embodiments, viewfinder mirror 103 is curved, concave, or convex. In some embodiments, viewfinder mirror 103 has a spherical shape. In some embodiments, viewfinder mirror 103 has a rectangular shape. It can be appreciated by those skilled in the art that smart mirror device 100 can be embodied with different shapes of viewfinder mirror 103 and/or a plurality of viewfinder mirror 103 without departing from the spirit of this invention.

Viewfinder mirror 103 includes a pass-through 914. Pass-through 914 allows the pass-through of light or visual information to allow light or visual information to reach image sensor 204 (so that a respective image can be captured) or to allow illumination of objects by light from light source 107. In some embodiments, pass-through 914 is an opening in viewfinder mirror 103. In some embodiments, pass-through 914 is a transparent or semi- or partially-transparent area in viewfinder mirror 103. In some embodiments, pass-through 914 includes an optical lens. In some embodiments, pass-through 914 is a section of the area of viewfinder mirror 103 that becomes transparent or partially transparent when light, possibly of an intensity above some threshold, is present. In some embodiments, pass-through 914 is a section of the area of viewfinder mirror 103 that becomes transparent or partially transparent when electrical current or voltage is present. Pass-through 914 can be located at the center of or at the perimeter, or at other locations of a viewfinder mirror 103. In some embodiments, pass-through 914 provides physical separation from the environment to other of oral piece 102's components, for example image sensor 204, when oral piece 102 is operating in an intraoral environment, or during sterilization or the like.

A plurality of pass-throughs 914 may exist. For example, smart mirror device 100 could include a rounded viewfinder mirror 103 having one pass-through 914 at its center (allowing visual information to reach image sensor 204) and a plurality of pass-throughs 914 equidistant along its perimeter (allowing light from a plurality of light sources 107 to provide illumination).

Image sensor 204 captures still or video digital images. In some embodiments, image sensor 204 is an image sensor, or plurality thereof, that includes a pixel array, such as a charged coupled device (CCD), or a complementary metal-oxide-semiconductor (CMOS) sensor, or the like. An example of an image sensor is the MT9V023 available form ON Semiconductor of Phoenix, Ariz. In some embodiments, image sensor 204 is part of a system-on-chip (SOC) with image sensing capabilities. The SOC that may include a memory and/or an image signal processor (ISP) or other components. An example for such a SOC is the OV5640 available from OmniVision Technologies Inc. of Santa Clara, Calif.

As described above, image sensor 204 is located relative to viewfinder mirror 103 so that at least some of the objects reflected in viewfinder mirror 103 are directly visible to image sensor 204 (so that they appear in a captured image). In some embodiments, image sensor 204 is located relative to viewfinder mirror 103 so that at least some of the objects reflected in viewfinder mirror 103 are indirectly visible to image sensor 204. In some embodiments, image sensor 204 is located relative to viewfinder mirror 103 so that at least some of the reflective surface of viewfinder mirror 103 is visible to image sensor 204. In some embodiments, image sensor 204 is located on or adjacent to the reflective area of viewfinder mirror 103. In some embodiments, image sensor 204 is integrated into viewfinder mirror 103. In some embodiments, image sensor 204 is adjacent to pass-through 914. In some embodiments, a lens and/or a light pipe, such as an optical fiber, transmits visual information to image sensor 204. In some embodiments, image sensor 204 is physically separated from the environment (for example an intraoral environment or sterilization environment) by a pass-through 914.

Light source 107 illuminates objects in the proximity of smart mirror device 100. In some embodiments, light source 107 illuminates areas of a person's mouth to improve the image reflected in viewfinder mirror 103 or captured by image sensor 204. In some embodiments, a plurality of light sources 107 are included. In some embodiments, light source 107 emits light. In some embodiments, light source 107 transmits light emitted elsewhere in smart mirror device 100. In some embodiments, the intensity of the light emitted or transmitted by light source 107 can be controlled. In some embodiments, the intensity of illumination by a plurality of light sources 107 is concurrently controlled. In some embodiments, the intensity of each light source 107 of a plurality of light sources 107 is independently controlled. In some embodiments, a plurality of light sources 107 all emit or transmit the same or similar light wavelengths (or colors). In some embodiments, different wavelengths (or colors) may be emitted or transmitted by a plurality of light sources 107. In some embodiments, light source 107 is a led emitting diode (LED). In some embodiments, light source 107 is a light pipe, such as an optical fiber cable or the like. It can be appreciated that other devices can be used as light source 107 to illuminate areas of a mouth without departing from the spirit of the present invention. In some embodiments, light source 107 is a monochromatic light (a laser). In some embodiments, light source 107 transmits light emitted by a laser. In some embodiments, light source 107 is located at a perimeter of viewfinder mirror 103. In some embodiments, light source 107 may be located at a different location of viewfinder mirror 103 and/or elsewhere in oral piece 102. In some embodiments, the light emitted and/or transmitted by light source 107 passes through a pass-through 914. In some embodiments, light source 107 is physically separated from the environment (for example an intraoral environment or sterilization environment) by a pass-through 914. In some embodiments, light source 107 is located or directed towards the "back" of viewfinder mirror 103 (further from the non-reflective area) of viewfinder mirror 103, providing ambient illumination as well as illuminating more of the environment space.

Connector 105 of oral piece 102 connects (physically and/or electronically) to connector 922 of hand piece 110. Connector 922 may be connector 113 illustrated in FIG. 1. Image sensor 204 and light source 107 receive electrical power from hand piece 110 through connector 105. In addition, control and signaling is passed to and from image sensor 204 and light source 107 through connector 105. For example, image sensor 204 may transmit images captured via bus 917 to connector 105, which transmits images to hand piece 110. Similarly, connector 105 may receive and pass along control information indicating when and whether to activate image sensor 204. For light source 107, connector 105 may receive commands on which light sources 107 to activate and when and how to activate them. Connector 105 is adapted to connect to a connector 922 in hand piece 110. In some embodiments, connector 105 and connector 922 may include a light connector, allowing transmission of light between hand piece 110 and oral piece 102.

Turning to hand piece 110, hand piece 110 includes an orientation measuring device 912, a user interface 924, a processor 923, a base station connector 958, a connector 922, communication subsystem 929, power subsystem 921, and a memory 930.

Base station connector 958 enables hand piece 110 which may or may not be attached to an oral piece 102 to dock with a base station. The docking may occur through a physical connection which holds hand piece 110 at a predefined orientation. In addition, the docking may occur through a USB or near field communication connection or the like. When docking with the base station, hand piece 110 may receive electrical power through base station connector 958, which may be used to charge power subsystem 921. In addition, hand piece 110 may receive control and signaling information through base station connector 958. For example, base station connector 958 may receive information needed to configure a wireless communication connection between hand piece 110 and the base station. Base station connector 958 may provide the wireless configuration information (such as a service set identifier and password) to communication subsystem 929, as is discussed below. And, when docked to a base station, base station connector 958 may signal orientation measuring device 912 or software in memory 930 to calibrate.

Power subsystem 921 stores power for smart mirror device 100 and provides power to the other components of smart mirror device 100. Power subsystem 921 may include batteries, such as AAAA batteries, or a capacitor.

Orientation measuring device 912 measures an orientation (including x,y,z, position and yaw, pitch, roll direction) of viewfinder mirror 103 or generates data that enables to calculate an orientation of viewfinder mirror 103. In some embodiments, orientation measuring device 912 is an accelerometer. An example of an accelerometer is MMA8453Q available from NXP Semiconductors N.V. of Eindhoven, Netherlands. In some embodiments, orientation measuring device 912 is a gyroscope. An example of a gyroscope is FXAS21002C also available from NXP Semiconductors N.V.

User interface 924 includes an audio input 925, audio output 926, and input/output controls 927. Audio input 925 captures audial information. In some embodiments, audio input 925 includes a microphone. In some embodiments, audio input 925 captures human voice, for example, to enable a healthcare provider to dictate observations for a patient's medical record. Hand piece 110 includes an audio output 926, which emits sounds. In some embodiments, audio output 926 includes one or more speakers. In some embodiments, audio output 926 includes headphone jacks and/or headphones.

Input/output controls 927 can include buttons, lights, knobs, capacitive sensors, actuators for haptic feedback or the like for a user to control and/or receive feedback relating to processes in smart mirror device 100, for example, to initiate audio recording or image capturing, or set an intensity of illumination.

Communication subsystem 929 allows hand piece 110 to connect to one or more remote computational devices, including, for example, to a base station, or to a general purpose computational device such as personal computer, a smart phone, a tablet or similar, or a specialized computational device such as to another smart mirror device or remote speakers or the like. In some embodiments, communication subsystem 929 is adapted to connect to a wireless network, including, but not limited to, WiFi and/or Bluetooth. In some embodiments, communication subsystem 929 is adapted to attach to a wired network, including, but not limited to, Ethernet, USB or thunderbolt.

Memory 930 may include random access memory (RAM) and may also include nonvolatile memory, such as read only memory (ROM) and/or flash memory. Memory 430 may be embodied as an independent memory component, and may also be embedded in another component, such as processor 923 and/or image sensor 204, or may be embodied as a combination of independent as well as embedded, and/or a plurality of memory components is present, the invention is not so limited. Memory 930 is adapted to include software modules (a module is a set of instructions). In particular, memory 930 includes a streamer module 953, identification module 954, power monitor module 955, HTTP server module 956, illumination controller module 950, image control module 951, and orientation calculator module 968.

Processor 923 is adapted to run instructions stored in memory 930. Processor 923 may be a micro-controller unit (MCU), a digital signal processor (DSP) and/or an Image/Video Processing unit or the like components that run instructions. An example of an MCU is MSP432P401x available from Texas Instruments Inc. of Dallas, Tex. An example of a DSP is C5000 available from Texas Instruments Inc. of Dallas, Tex. An example of an image/video processor is OMAP3525 available from Texas Instruments Inc. of Dallas, Tex. One or more processor 923 may be present. Processor 923 may be an independent component, it may also be embedded in another component, such as in image sensor 204, or any combination thereof.

Illumination controller module 950 controls the operation of light source 107. In some embodiments, illumination module 950 sets the intensity of illumination of light source 107. In some embodiments, illumination module 950 receives a user request to increase or reduce illumination. In some embodiments, illumination module 950 receives user request to turn on or off some or all of light source 107. In some embodiments, illumination controller module 950 receives requests from other software modules to increase and/or decrease illumination of one or more of light source 107. In some embodiments, user input as well as said requests are used to determine an intensity of illumination.

Orientation calculator module 968 reads data from orientation measuring device 912. Orientation calculator module 968 may for example integrate data from a gyroscope and accelerometer to determine a location (in, for example, x,y,z coordinates) and a direction (for example, yaw, pitch, and roll). Because orientation calculator module 968 uses integration to determine the location and direction of smart mirror device 100, errors from the gyroscope and the accelerometer can accumulate over time. However, as described above, base station connector 958 may dock with the base station in such a way to position hand piece 110 at a known angle. When base station connector 958 is docked with the base station, base station connector 958 may signal orientation calculator module 968 to calibrate. To calibrate, orientation calculator module 968 may set the x, y, z, and yaw, pitch, and roll values to fixed values, such as the value zero. Thus, when hand piece 110 is moved around, the coordinate and direction values orientation calculator module 968 determines may be relative to the coordinate and direction values set at the base station.

Image control module 951 controls the capture of images and video, and affects the output image quality. In some embodiments, image control module 951 controls the intensity of illumination, for example, by requests to illumination module 950, for example to improve the illumination conditions for a better image capture quality. In some embodiments, image control module 951 processes a set of time-successive images to create a single output image which has an improved visual quality, for example, but not limited to by selecting one image out of the set, or by combining portions of images, each portion from an image in the set. In some embodiments, values indicating the acceleration of image sensor 204 when an image was captured are used to improve the quality of an output image, for example, but not limited to, selecting images with least acceleration or interpolating among portions of two or more images of different acceleration. In some embodiments, image control module 951 controls the aperture and/or focal point of a lens. In some embodiments, image control module 951 triggers the capture of a sequence of images each with a different illumination. In some embodiments, image control module 951 triggers the capture of a sequence of images each with a possibly different group of one or more of light sources 107 set to illuminate, while the other one or more of light source 107 set to not illuminate. In some embodiments, image control module 951 rotates an image, for example based on a rotation value generated by orientation calculator module 968.

Identification module 954 identifies smart mirror device 100 to a remote computational device. In some embodiments, identification module 954 implements an authentication handshake protocol in which the identification occurs over a network session. In some embodiments, identification module 954 couples an identification to data prior to the data being transferred to a remote computational device. The identification may include a globally unique ID for hand piece 110. It may also be timestamped and digitally signed.

Power monitor module 955 monitors the amount of energy available by the power subsystem, and the power usage of smart mirror device 100. In some embodiments, power monitor module 955 receives a motion indication generated by orientation measuring device 912, for example, but not limited to, an acceleration indication. In some embodiments, power monitor module 955 sets smart mirror device 100 into a standby mode when smart mirror device 100 is not being used for a time interval larger than some threshold. To set a standby mode, in which smart mirror device 100 consumes a reduced amount of power, power monitor module 955 may reduce or completely shut down the power supply to some of smart mirror device 100 components and/or alter or completely pause some of smart mirror device 100 software processes, or the like. In some embodiments, power monitor module 955 exits a standby mode, for example, by resuming power to some of smart mirror device 100's components or resuming execution of some of smart mirror device 100's processes, when an indication of usage of smart mirror device 100 is present. In some embodiments, power monitor 955 enters or exits a standby mode based on other parameters or indications, the invention is not so limited. In some embodiments, power monitor 955 performs a shutdown, shutting power to more (when compared to standby mode) or even all of smart mirror device 100 components, when an indication of not being used is present for a time interval larger than some threshold, or based on other parameters or indications.

Streamer module 953 prepares and/or streams data to a remote computational device. The data can include video collected from image sensor 204, smart mirror device 100's orientation and location collected from orientation calculator module 968, audio input collected from audio input 925, any data collected from input/output controls 927, power related data collected from power monitor 955 and the specification of how light source 107 is illuminated from illumination controller module 950. Streamer module 953 may associate data collected from these various sources with each other. To associate data collected from different sources, streamer module 953 may attach a timestamp. For example, each frame in video image sensor 204 may include a timestamp which is collected. Similarly, the orientation, audio, power, and input control information may have a timestamp indicating when that information was collected, and the illumination information may have a timestamp indicating when light source 107 was illuminated in the manner specified.

In some embodiments, streamer module 953 formats images, video, audio and other data in a format for streaming to an application executing on a remote computational device via communication subsystem 929. In some embodiments, streamer module 953 formats images, video, audio and other data in a format suitable for streaming to an Internet browser, for example, but not limited to, HTTP streaming, HTML, HTML5, RTSP, WebRTC. In some embodiments, streamer module 953 formats images, video, audio and other data with compression formats and/or format containers such as, but not limited to, JPG, JPG 2000, MPEG-4, H.264, H.265, AAC, PCM, G.711, G.726, and the like. In some embodiments a proprietary format is used, the invention is not so limited.

In addition to streamer module 953, hand piece 110 may transmit data using a HTTP server 956. In some embodiments, HTTP server 956 responds to HTTP requests originating in a remote computational device.

Back to FIG. 7, in an embodiment, a viewfinder mirror of smart mirror device 100 includes light sources within the spectrum that enables the curing of resin. A health care provider may illuminate the resin using the lights of a smart mirror device, while observing the progress of the curing process in tablet 806. In addition to avoiding the exposure of the health care provider to a light that may be harmful to his eye, it enables to immediately continue the process of structure buildup, without requiring to switch instruments.

Figure 10:
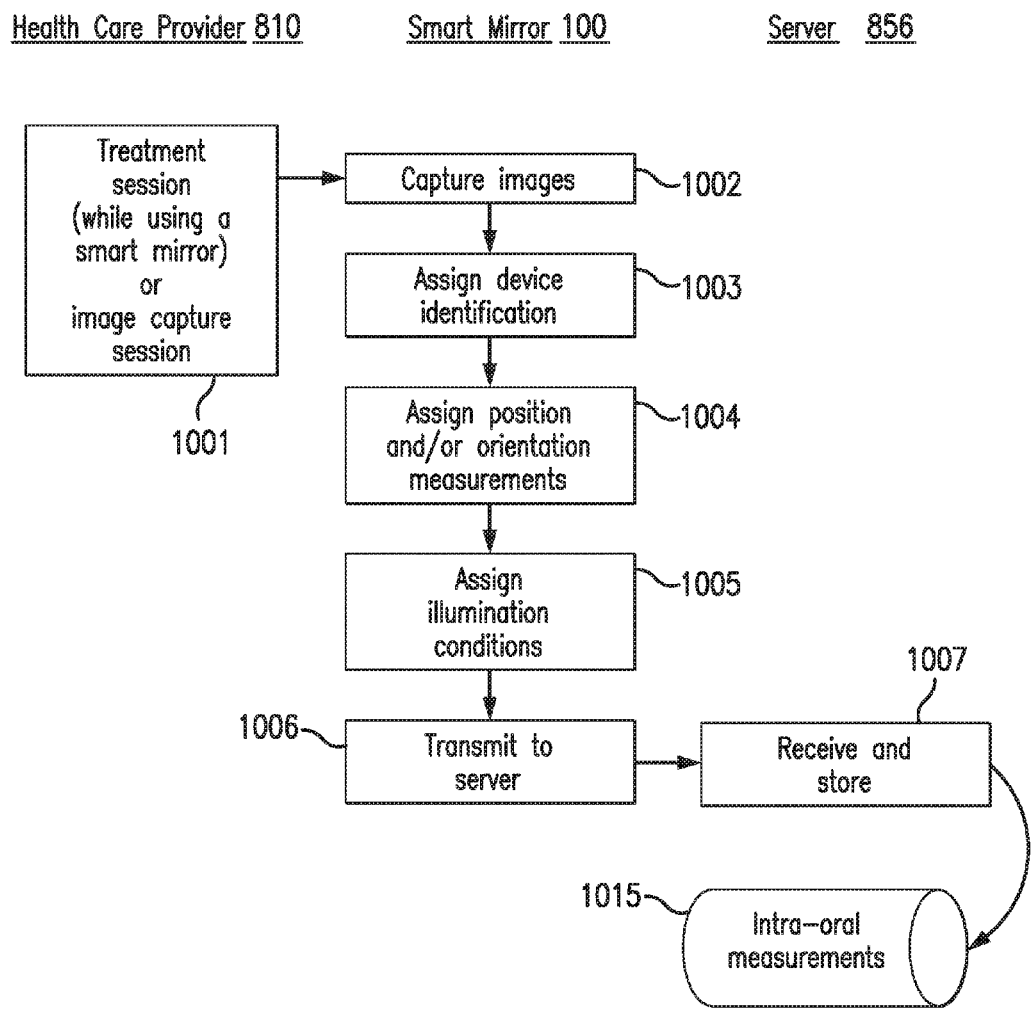
FIG. 10 is a flowchart illustrating an example operation of the system of FIG. 8A.

FIG. 10 is a flowchart illustrating an example method 1000 of the system of FIG. 8A for distributed acquisition of images and possibly also supplementary data, and their storage for a subsequent processing, such as the creating of a panoramic or immersive photograph, or the generation of digital dental impressions.

Method 1000 starts at step 1001 when a health care provider (HCP), such as a dentist, a hygienist, or other, is performing an intraoral procedure while, at least some of the time, the HCP observes the reflection of an intraoral environment area of interest in the viewfinder mirror of a smart mirror. This may occur in a variety of such procedures since an intraoral mirror is a frequently used instrument, including, but are not limited to, common procedures such as teeth inspection, or a professional teeth cleaning. It can also be, but does not need to be, a dedicated image acquisition session, for example to generate a digital impression.

At step 1002, the smart mirror captures images (still or video). In some embodiments time-tag supplementary data is optionally assigned to the images. The time-tag indicates a time of image capture. In some embodiments, some or all of the smart mirror light sources are active, illuminating the intraoral environment when images are captured. In some embodiments, a light source illuminates with a light visible to the human eye, for example (but not limited to) "daylight", which has a color temperature of 5,500K-6000K, common in an electronic camera flash. In some embodiments, while capturing a plurality of images, the active light sources vary, resulting in images of an object (or objects) in the intraoral environment, each captured with distinct illumination conditions. Such plurality of images that differ in illumination conditions may provide information useful for a 3D reconstruction of the scene being captured, for example, due to the different shadows present. In some embodiments, the variation of illumination conditions is such that the HCP may observe a plurality of illumination conditions. In some embodiments, the variation of illumination conditions is occurring at a rapid pace, faster than may be perceived by the human eye, so that possibly to the HCP the illumination seems steady. In some embodiments, a light source illuminates with a light which is not within the human visible light spectrum, for example an infrared light (of wavelengths around 700-1600 nm), so that an HCP cannot perceive such illumination or a variation in such illumination, and yet allowing the capture of images by a sensor that is sensitive to such light.

At step 1003, a device identification supplementary data is assigned to the images. The device identification identifies a particular smart mirror device. The device identification might be one or more serial numbers, and/or an encoded message (for example an encrypted message), and/or an authentication key (for example a public key) or other.

At step 1004, orientation data, including position and/or direction supplementary data, is assigned to the images. A position supplementary data specifies, or can be used to calculate, a spatial location of a point of interest on smart mirror, for example the position of the center of the viewfinder mirror or the position of the center of an image capture device, relative to a reference location. A direction supplementary data specifies one or more angles pertaining to the angular position, representing the geometric rotations around a point of interest, for example the rotation around the center of the viewfinder mirror or the rotation around the center of an image capture device, relative to a reference direction. In some embodiments, the position and/or direction at the time of an image capture is assigned to an image. In some embodiments, the position and/or direction is tagged with a time-tag specifying the time at which said position and/or direction were reached. In some embodiments, a plurality of positions and/or direction along with their respective time-tags are assigned to one or more images. It may be appreciated by those skilled in the art that additional embodiments may allow supplementing an image with information regarding the position and/or direction reached at the time the image was captured, without departing from the spirit of this invention.

In some embodiments, assignment of supplementary data to an image is achieved by amending a digital representation of an image with supplementary data, for example (but not limited to), by adding fields to an EXIF file (Exchangeable Image File Format) of an image. In some embodiments, assignment of supplementary data to an image is achieved by coupling an image and coupling a supplementary data with correlating information. For example, but not limited to, the digital representation of an image and the supplementary data are coupled with a patient's identification, and with correlating time-tags (e.g. relating to the same time reference). It may be appreciated by those skilled in the art that additional embodiments may allow assigning supplementary data to an image, without departing the spirit of this invention.

At step 1005, illumination conditions supplementary data is optionally assigned to the images. Illumination conditions supplementary data specifies information regarding the light sources of smart mirror, including which of the light sources is active (and/or which is not active), and possibly for each light source at what intensity, color or the like attributes. In some embodiments, the illumination conditions that are present at the time of an image capture are assigned to the image. In some embodiments, a set of time-tags with corresponding illumination conditions describe intervals at which the said conditions remain unchanged, effectively describing temporal changes to illumination. In some embodiments, a plurality of illumination conditions along with their respective time-tags are assigned to one or more images. It may be appreciated by those skilled in the art that additional embodiments may allow supplementing an image with information regarding the illumination conditions at which the image was captured, without departing from the spirit of this invention.

At step 1006, the images and supplementary data are transmitted to a server. The transmission to the server may occur through the base station.

At step 1007, images and other data received at the server are stored in an intraoral measurements database 1015 (a database organizes data so that it is readily accessible).

Figure 11:
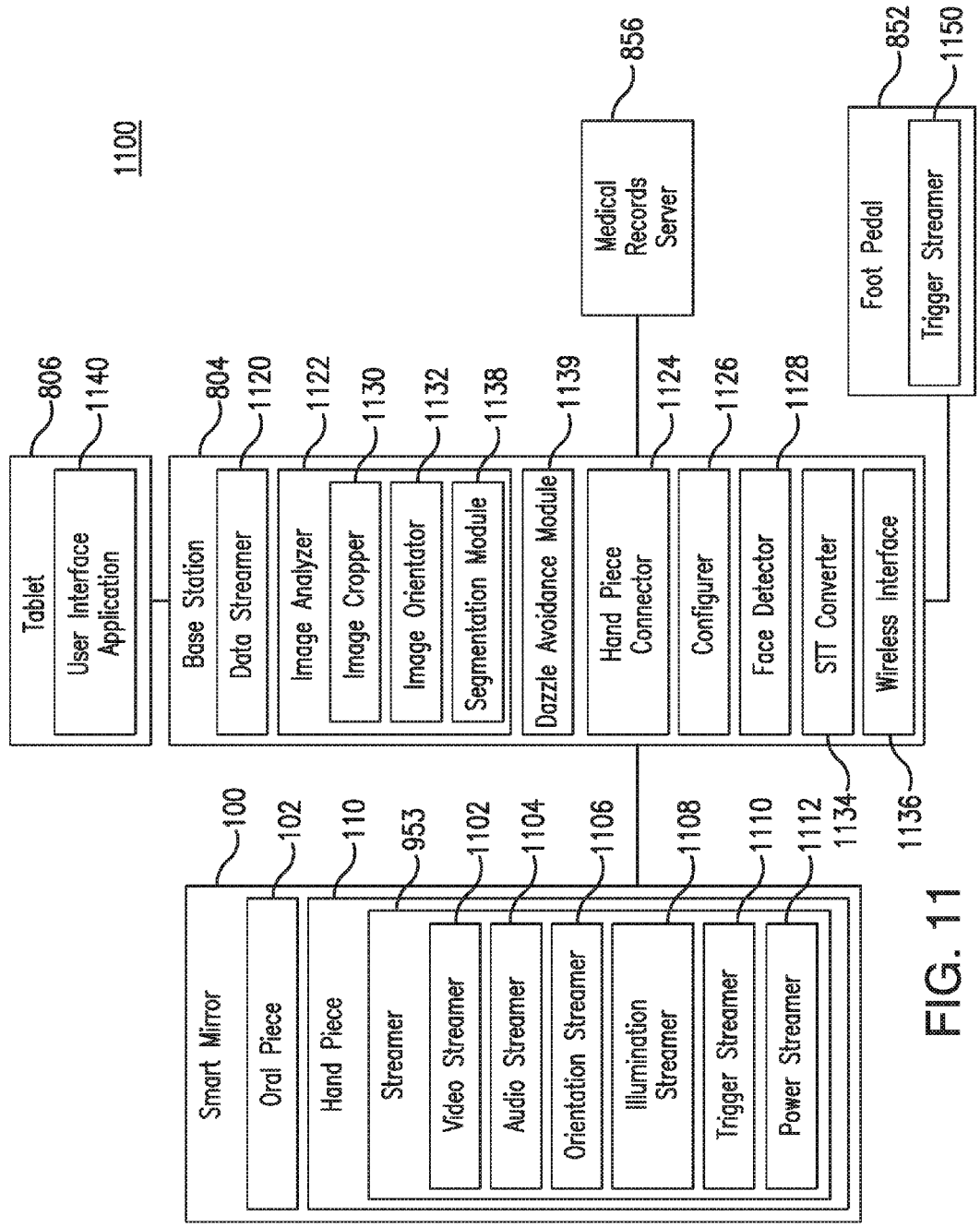
FIG. 11 is a block diagram further detailing components of the system of FIG. 8A.

FIG. 11 illustrates a block diagram 1100 further detailing components of the system of FIG. 8B. Like in FIG. 8B, diagram 1100 includes smart mirror device 100, tablet 806, medical records server 856, and foot pedal 852, all in communication with base station 804. Foot pedal 852, smart mirror device 100, and tablet 806 may communicate with base station 804 via a wireless interface 1136.

As detailed FIG. 9, smart mirror device 100 includes oral piece 102 and hand piece 110, which includes a streamer module 953 that streams data from smart mirror device 100 to base station 804. As shown in diagram 1100, streamer module 953 includes a number of submodules, each streaming a different type of data to base station 804. In particular, streamer module 953 includes: a video streamer 1102 that streams video data, audio streamer 1104 that streams audio data, an orientation streamer 1106 that streams orientation and location data, an illumination streamer 1108 that streams illumination data, a power steamer 1112 that streams power monitoring data, and a trigger streamer 1110 that streams user input from smart mirror device 100, such as button presses. As discussed above, each of these data streams may be correlated, for example with time-tags. Streamer module 953 streams these various data streams to base station 804.

Base station 804 includes an image analyzer module 1122, a face detector module 1128, a data streamer module 1120, a hand piece connector 1124, configurer module 1126, STT converter 1134, wireless interface 1136, and a dazzle avoidance module 1139. Image analyzer module 1122 analyzes the incoming video stream to capture what is visible to a healthcare provider on smart mirror device 100's mirrored surface. To analyze the incoming video stream, image analyzer module 1122 includes an image cropper module 1130, an image orientation module 1132, and a segmentation module 1138.

Face detector module 1128 receives an image from the image sensor and determines a location of the health care provider's face within the received image. In addition, face detector module 1128 may determine a size of the face within the received image. By determining a face's location and size, face detector module 1128 may determine a region of the image that includes the healthcare provider's face. Face detector module 1128 may be trained to locate a specific feature of the healthcare provider's face, such as her eyes. Face detector module 1128 may use any face detection algorithm. For example, face detector module 1128 may use a genetic algorithm, a neural network trained to identify faces, or an eigen-face algorithm. In an embodiment, image analyzer module 1122 uses data generated by face detector module 1128 together with respective orientation data to determine a direction towards the healthcare provider's face. The result is recorded as the latest known direction and may be used thereafter to estimate the position of healthcare's provider face in cases that they do not appear clearly in the image.

Face detector module 1128 may detect a plurality of faces within the received image. In that case, face detector module 1128 may need to determine which face corresponds to the healthcare provider. Face detector module 1128 may determine the healthcare provider's face to be the largest within the received image. Alternatively, face detector module 1128 may use the latest recorded direction towards the healthcare provider's face as an input for its selection. Also, face detector module 1128 may recognize the healthcare provider's face using a facial recognition algorithm. A facial recognition algorithm may operate by detecting features of the face in the image and comparing with known features of the healthcare provider. In addition, the facial recognition algorithm could be used to identify and authenticate the healthcare provider using smart mirror device 100.

Based on the location of the healthcare provider's face determined by face detector module 1128, image analyzer module 1122 determines a portion of the image visible to the health care provider on the mirror surface. Image analyzer module 1122 may apply the analysis, such as cropping, to additional images subsequent to the one detected by face detector module 1128. Image analyzer module 1122 may operate as described above for FIGS. 4, 6A and B.

In addition, image analyzer module 1122 corrects for distortions caused by the viewing angle of smart mirror device 100's lens. As mentioned above, smart mirror device 100's lens may be a wide angle lens. Wide angle lenses can cause barrel distortion, where straight lines are curved inwards in the shape of a barrel. Image analyzer module 1122 may, for example, correct for these barrel distortions.

Once image analyzer module 1122 corrects for any distortions and determines which portion of an image from a received video stream is of interest, image analyzer module 1122's image cropper module 1130 may crop the determined portion from the image. In this way, image analyzer module 1122 crops frames of the received video to more closely represent what is apparent to the health care provider on smart mirror device 100's reflective surface.

Image analyzer module 1122's image orientation module 1132 may correct for the orientation of smart mirror device 100. Image orientation module 1132 may correct for smart mirror device 100's orientation based on the orientation information received from smart mirror device 100 that correlates to the image from the video. Using the orientation information, image orientation module 1132 may correct for smart mirror device 100's orientation as described above for FIGS. 5A-C and 6B.

Image analyzer module 1122 may conduct the above operations to crop and orient every frame of video streamed from smart device 100. After the images are cropped and oriented, base station 804's data streamer module 1120 may buffer in a memory and stream the information to tablet 806 for display to the user. Additionally, base station 804's data streamer module 1120 may buffer in a memory and stream images and other information to medical records server 856 for analysis or archiving. Base station 804 also buffers full sized images together with location, illumination, and other data received from smart mirror device 100.

Image analyzer module 1122 may recognize an object in an image sensed by the image sensor. For example, image analyzer module 1122 includes a segmentation module 1138 configured to determine an area of the image that shows the object inside a patient's mouth. Segmentation module 1138 configured to segment the image into intra and extra-oral sections. To segment the image into intra and extra-oral sections, segmentation module 1138 may first receive a plurality of photographs taken by the image sensor from substantially the same position with varying intensity of light emitted from the plurality of light sources. Then, segmentation module 1138 may compare brightness in a plurality of different portions between the plurality of images. Finally, segmentation module 1138 may determine the intra-oral section as a portion in the plurality of different portions based on a variance in brightness between the plurality of images. For example, segmentation module 1138 that the a greater variance in brightness may be a surface close to the smart mirror device.

Dazzle avoidance module 1139 directs light emitted by the smart mirror device to avoid dazzling the health care provider. Dazzle avoidance module 1139 may direct light toward the intra-oral portion detected by segmentation module 1138 or away from the health care provider's face detected by face detector 1128. To direct light, dazzle avoidance module 1139 may send commands to smart mirror device 100 to adjust the direction or intensity of light emitted by its light sources, as described above with respect to FIGS. 7A-C.

Tablet 806 executes a user interface application 1140, which is in wireless communication with base station 804. User interface application 1104 is capable of displaying to a patient images collected from the image sensor.

In addition to streaming video, a healthcare provider may be interested in capturing an image at a particular point in time. To capture an image in this way, a healthcare provider may select a button residing on handpiece 110 of smart mirror device 100. When the healthcare provider selects the button, trigger streamer 1110 transmits to base station 804 a trigger message with a time tag correlating to when the button was selected.

When base station 804 receives the trigger message, image analyzer module 1122 selects, from plurality of frames in the video, a plurality of frames prior to the time when the button was pressed. When the button is pressed, the smart mirror device 100 is likely moved. By selecting frames immediately before the time when the button was pressed, the selected frames may more accurately represent the subject matter that the healthcare provider sought to capture. Once image analyzer module 1122 selects a plurality of frames, image analyzer module 1122 blends the plurality of frames into a composite image. This process of generating the composite image is described in greater detail with respect to FIG. 16 below. The composite image may be presented to the user and user interface application 1140 and may be archived in medical records server 856.

In addition to the trigger button on smart mirror device 100, foot pedal 852 may also be used for input, for example to trigger the capture of an image. In one embodiment, the button on smart mirror device 100 may be used to capture an image, while foot pedal 852 may be used to capture audio. Foot pedal 852 is configured to wirelessly communicate with the base station to provide user input to the base station. Foot pedal 852 includes a trigger streamer module 1150.

When depressed, trigger streamer 1150 may transmit a message to base station 804 indicating that foot pedal 852 is depressed and when foot pedal 852 was depressed. Using this information, base station 804 can correlate with audio received from audio streamer module 1104 on smart mirror device 100.

Once the appropriate audio that was input while the foot pedal is depressed is determined, speech to text converter 1134 can convert the determined audio into text. Speech to text converter 1134 may transmit the audio to a cloud service that provides transcription. The transcription may then be stored in a database entry in medical records server 856. Speech to text converter 1134 may recognize the text in a structured format. For example, the healthcare provider may recite the name of a tooth and, following the name of the tooth, recite its condition. For example, the healthcare provider may state "right maxillary 2nd bicuspid" and state "cavity." Recognizing this statement, speech to text converter 1134 may note a cavity in a database entry in medical records server 856 corresponding to the right maxillary 2nd bicuspid.

In addition to providing audio input for conversion to text, audio input of smart mirror device 100 enables to trigger actions by voice commands. Audio captured at the audio input is streamed to the base station, where speech to text converter 1134 analyzes it to locate certain keywords, for example the word "snapshot", or "convert speech". If such keyword is recognized, the corresponding action takes place. For example, the snapshot is taken or speech is converted into text for entry into the patient's medical record.

Configurer module 1126 is configured to, when the dental mirror is in proximity to the base station, transmit, to smart mirror device 100, configuration information necessary to configure the wireless communication between the dental mirror and the base station. In one embodiment, configurer module 1126 is configured to transmit the configuration information when the dental mirror is docked with a hand piece connector 1124. In another embodiment, configurer module 1126 is configured to transmit the configuration information when the dental mirror is in range for near field communication (NFC).

Configurer module 1126 operates to provide the necessary configuration information to tablet 806 and foot pedal 852 as well. When tablet 806 or foot pedal 852 is in proximity to the base station, Configurer module 1126 transmits to tablet 806 or foot pedal 852 configuration information necessary to configure the wireless communication between tablet 806 or foot pedal 852. Configurer module 1126 may transmit the configuration information when it is in NFC range or when it is connected electrically by a wire, such as a USB cable.

Figure 12:
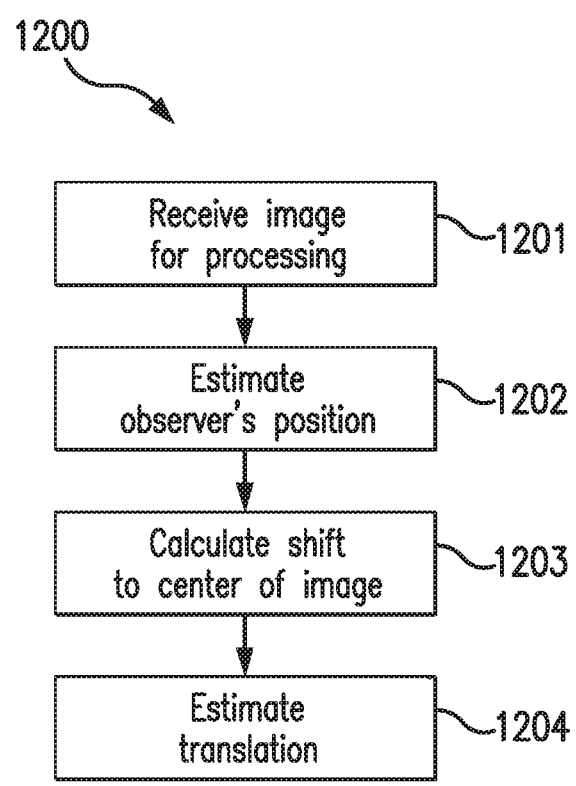
FIG. 12 is a flowchart illustrating a method to estimate the portion of the image captured by an image sensor in the intraoral mirror that is visible to a healthcare provider.

FIG. 12 is a flowchart illustrating a process 1200 to estimate the portion of the image captured by an image sensor in the intraoral mirror that is visible to a healthcare provider. In particular, process 1200 calculates a translation adjustment to the center of interest in an image captured using a viewfinder mirror, according to some embodiments of the invention. Process 1200 may, for example, be used in operation of image analyzer module 1122 in FIG. 11.

Process 1200 begins at step 1201 when an image is received. Then, at step 1202 an estimation of the location (coordinates) of an observer's position within the frame of the image is calculated. In some embodiments, the coordinates of an observer's position are estimated by finding the brightest area of the image and calculating a center in that area (assuming that in an image captured in an intraoral environment, using a viewfinder mirror, the brightest area indicates presence of light arriving from the outside of a person's mouth). In some embodiments, a pattern of incisor (front tooth) is recognized and a center of the gap between the positions of centers of upper and lower incisors is used as an estimation of an observer's position. In some embodiments, a pattern of a part in the human face, such as an eye's iris or pupil is recognized, and the position of its center in the image is used as an estimation of an observer's position. At step 1203, the shift or difference in image frame coordinates, between the center of the image and the estimated observer's position is calculated. At step 1204 the calculated shift is used to calculate a translation adjustment. The shift and translation adjustment may be calculated as described above for FIG. 6A.

Figure 13:
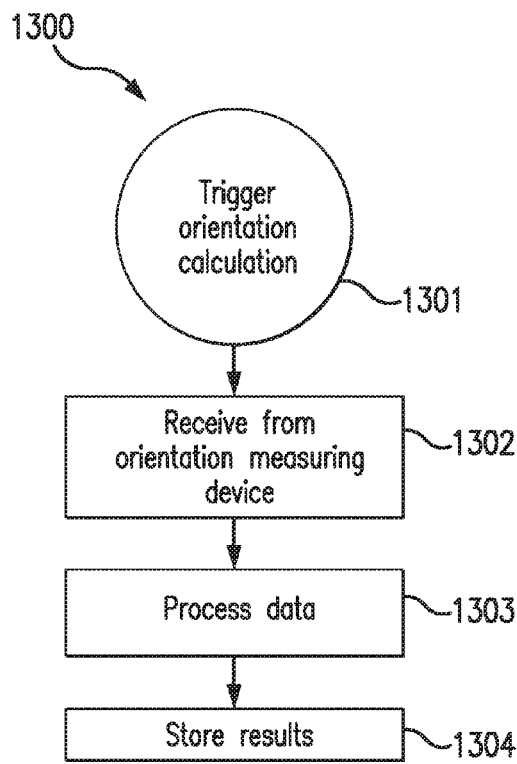
FIGS. 13 and 14 illustrate methods for rotating the image to adjust for the orientation of the intraoral mirror.
Figure 14:
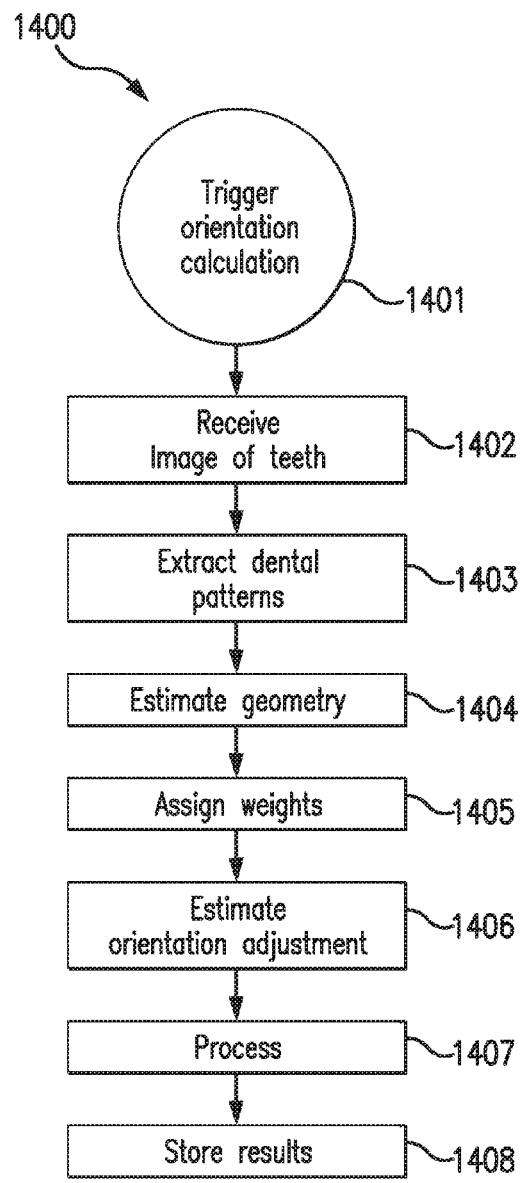

FIGS. 13 and 14 illustrate methods for rotating the image to adjust for the orientation of the intraoral mirror. FIGS. 13 and 14 may be employed in operation of image orientation module 1132 in FIG. 11. FIG. 13 is a flow diagram illustrating a process 1300 for calculating an orientation of a viewfinder mirror, according to some embodiments of the invention.

Process 1300 begins at step 1301 when a calculation is triggered. In some embodiments, the calculation is triggered by an orientation measuring device, for example when such device senses a change in orientation. In some embodiments, the calculation is triggered by a timer, for example, when at the end of a given time interval. In some embodiments, the calculation is triggered when the measure of orientation is requested by another process.

Once triggered, at step 1302, data from one or more orientation measuring devices is received. At step 1303, the data is processed. In some embodiments, said data process includes combining said data with results obtained in one or more preceding executing cycles of process 1300. In some embodiments, said data process includes the integration of said data over time. In some embodiments, said data process includes the calculation of a moving window average over data. In some embodiments, said data process includes applying a signal processing filter, for example a low pass filter. In some embodiments, no filtering is required, and said data is used as received. In some embodiments, the said data and/or the result of said data processing are adapted for use by one or more further run cycles of process 1300 and/or by another process. In some embodiments, other filtering techniques are used with the purpose to smooth the output of process 1300. In some embodiments a plurality and/or combination of the above are used. In 1304 the result (or results) is stored for usage by another process or by a future run cycle of process 1300.

FIG. 14 is a flow diagram illustrating a process 1400 for calculating an adjustment to the orientation of a viewfinder mirror, according to some embodiments.

Process 1400 begins at step 1401, when an orientation calculation is triggered. Step 1401 is similar to step 1301 of FIG. 13. At step 1402, an image of teeth (intraoral or other) is received. At step 1403, image processing is applied to the image (for example, but not limited to edge-detection and feature detection techniques) to find at least one of the following patterns:

(1) the line formed by the bottom edge of the top teeth (the contour of the incisal edges of the maxillary anterior teeth, sometimes called the "smile arc," or the occlusal plane of the upper posterior teeth);

(2) the line formed by the top edge of the bottom teeth (the occlusal plane of lower incisors or posterior teeth); or (3) the embrasures and/or visible lines between teeth (interproximal contact areas, "connectors"), or gaps between teeth.

Each pattern is then represented as a vector.

At step 1404, the spatial geometry (defining which patterns are closer and which are further from the respective image capture device) of the patterns found is estimated, by using at least one of:

(1) relative dimensions of patterns found;

(2) relative dimensions of objects;

(3) prior knowledge of patient's teeth and mouth structure;

(4) prior knowledge of standard dimensions.

At step 1405, a value is assigned to each pattern. The value serves as a weight of the respective pattern in the calculation of orientation adjustment. In some embodiments, the patterns found to be at a closer proximity receive a higher weight. In some embodiments, the patterns at the center of the image receive a higher weight. In some embodiments, the patterns at the area in the image that is estimated to represent the center of viewfinder mirror receive a higher weight. In some embodiments some patterns receive a weight of 1 and zero, one or more receive a weight of 0.

At step 1406, the spatial geometry generated in step 1404 and the weights generated in step 1405 are combined to calculate an estimate angle to use to adjusting the orientation of the image. The angle calculated to position a tooth toward a top or bottom of the image such that the tooth has a portrait orientation.

At step 1407, the angle is processed as described above for step 1303 and at step the resulting angle is stored at step 1408 as described above for step 1304.

Figure 15A:
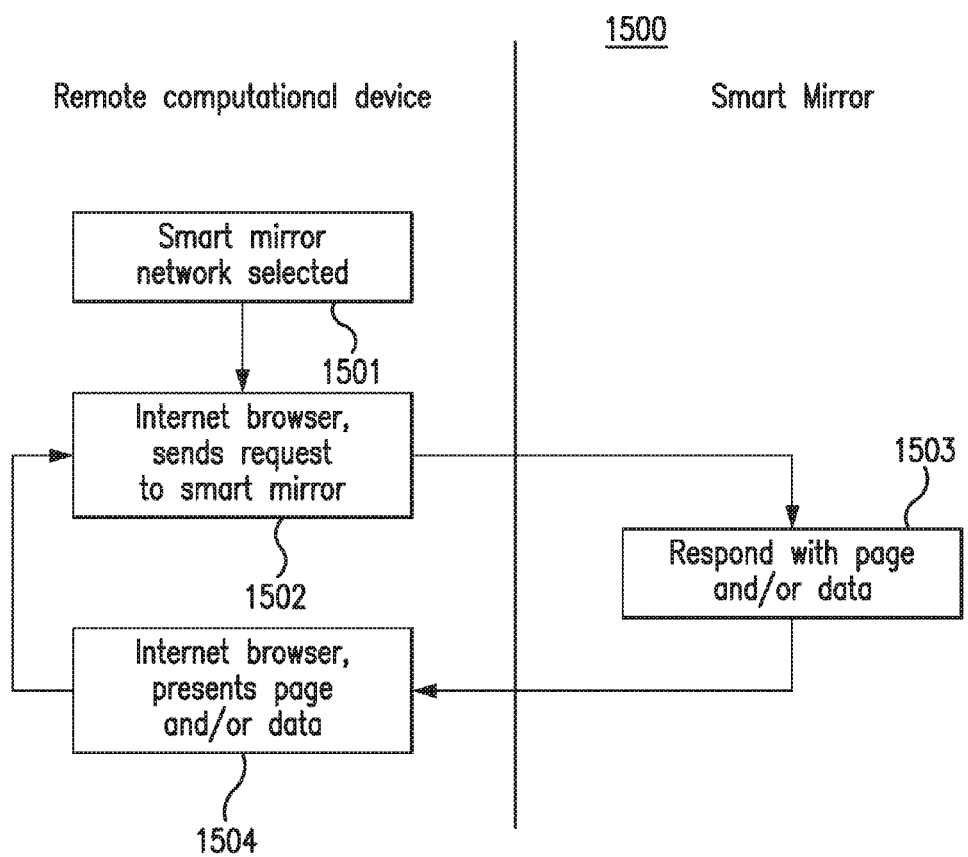
FIG. 15A-B illustrate alternative methods to retrieve data from an intraoral mirror device.
Figure 15B:
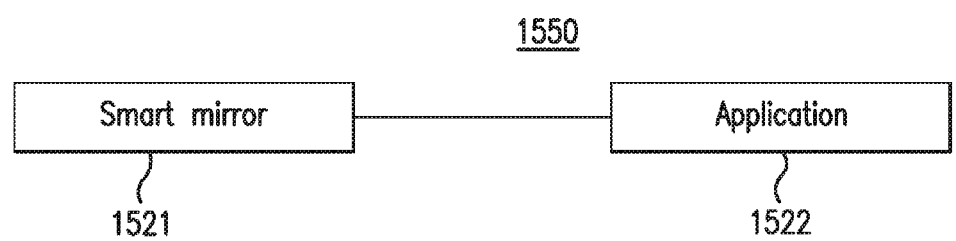

FIG. 15A-B illustrate alternative methods to retrieve data from an intraoral mirror device. FIG. 15 is a flow diagram illustrating a process 1500 of user interaction with smart mirror, using an Internet browser executing in a computational device.

Process 1500 begins at step 1501 when a network published by smart mirror is selected. In some embodiments, the network is a WiFi network, and smart mirror broadcasts a Service Set Identifier (SSID) emulating a WiFi router or gateway or the like, so that a user may select it. In some embodiments, a user selects a network previously known to the computational device. In some embodiments, a computational device automatically selects smart mirror as a router. In some embodiments, a user otherwise chooses the network, the invention is not so limited. In some embodiments, at step 1501 a smart mirror and a computational device are attached to a local area network (LAN) published by a router.

At step 1502, an Internet browser sends an HTTP request to smart mirror. In some embodiments, a user enters a Uniform Resource Locator (URL) and/or a Uniform Resource Identifier (URI) to the browser prior to the browser sending a request to smart mirror. In some embodiments, the browser sends a URL or URI or the like during its execution. In some embodiments, the browser sends a URL or URI or the like during the initiation of its execution. In some embodiments, the browser sends an asynchronous message, for example an Asynchronous Javascript and XML (AJAX).

At step 1503, smart mirror receives an HTTP request, and responds with a web page or other data. In some embodiments, data received by smart mirror may be processed and trigger certain actions, for example smart mirror may:

(1) receive a user and a password and enter a mode allowing additional user requests;

(2) receive a user and a password and store it in its internal memory;

(3) receive a selection of a local area network (LAN) and login data to said network;

(4) receive and store in its internal memory various configuration parameters;

(5) receive a request to stream images and/or audio and/or other, and thereafter perform one or more steps to respond to such requests, for example, but not limited to, the steps described in process 1000 (FIG. 10);

(6) receive and store in its internal memory a name to use as part of its own identification. It might be appreciated that there are various actions that an HTTP server implemented in a smart mirror can perform.

At step 1504, an Internet browser parses the data received from smart mirror and creates an appropriate presentation.

FIG. 15B depicts an embodiment of a system comprising a smart mirror device 1521 and an application 1522. Application 1522 is a set of modules (sets of instructions), stored or temporarily stored in a memory of a remote computational device in implementing one or more of the following computerized processes:

(1) search for one or more smart mirror devices;

(2) create a connection to a smart mirror device;

(3) receive a stream of video and/or audio and/or other data from smart mirror; or (4) send a configuration parameter to a smart mirror device, and the like processes. Such system provides an alternative to using an Internet browser (as described in process 1500, FIG. 15A), possibly providing an improved user experience.

Figure 16:
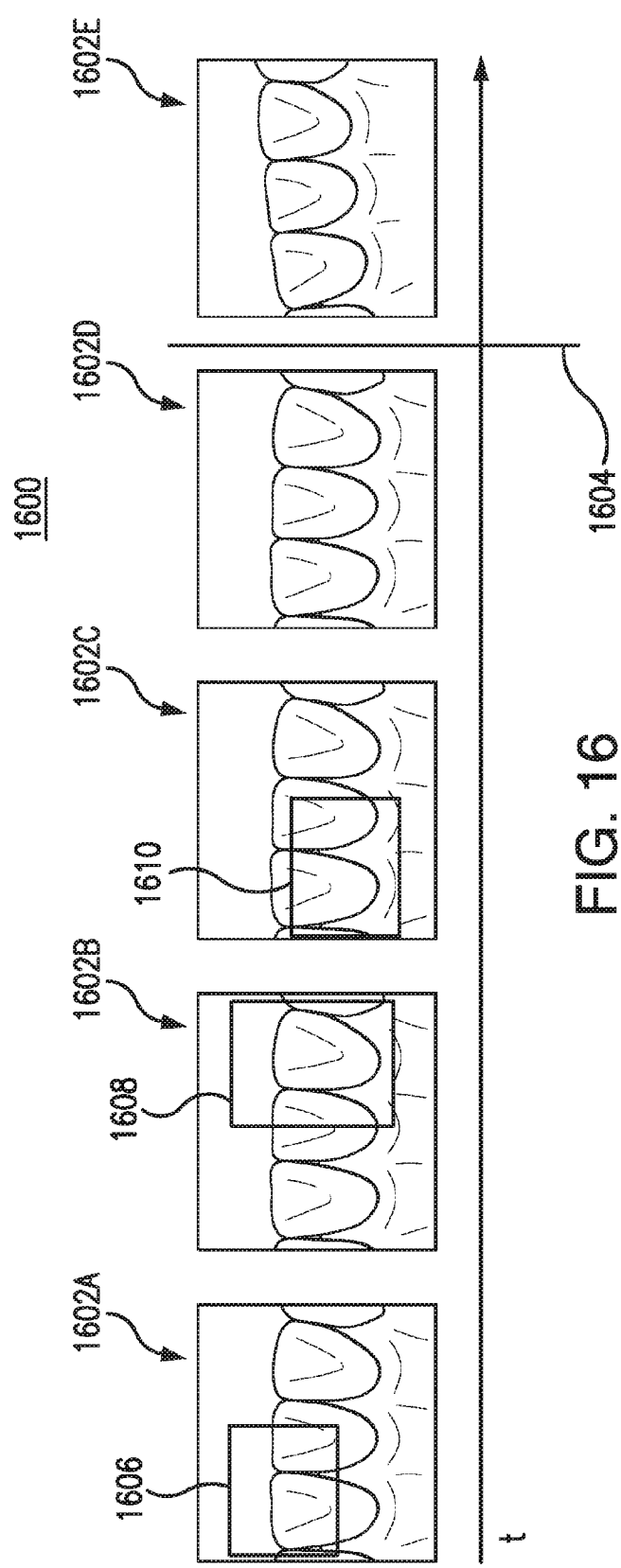
FIG. 16 is a diagram illustrating how images from a stream of images in a video from the intraoral mirror are selected for capture.

FIG. 16 is a diagram 1600 illustrating how images from a stream of images in a video from the intraoral mirror are selected for capture. Diagram 1600 includes a chronological sequence of images 1602A-E. Images 1602A-E may be frames from a video collected from a smart mirror device. In particular, images 1602A-E may be frames that have been processed, cropped and rotated as discussed above to reflect what is apparent to the observer of the smart mirror device.

At a time 1604, a user of the smart mirror device makes an input to request that an image be captured. Time 1604 occurs after image 1602D is captured but before frame 1602E is captured. The input may, for example, be a button press on the smart mirror device. Pressing a button may cause the smart mirror device to be moved away from the object that the user intends to capture. This is illustrated, for example, in frame 1602E. For this reason, frame 1602E is not selected for capture. Instead, at least one of the earlier images 1602A-D may be captured.

Moreover, several of the earlier images may be used to generate the captured image. The lighting, clarity, and focus may vary at each image. Thus, portions of the various images may be selected and blended together. In diagram 1600, portion 1606 of image 1602A, portion 1608 of image 1602B, and portion 1610 of image 1602C are selected. The selected portions are blended together to form a final composite image that is captured.

In this way, various systems and methods are presented that utilize in an intraoral mirror with an integrated camera.

D. Utilizing an Intraoral Mirror to Generate Patient Status

An intraoral mirror with an integrated camera can be utilized to capture a patient's dental status in a panoramic 2D photo (also called mosaic) and/or an immersive photo (also called 360 degrees photo, or sometimes virtual reality photo) of a patient's mouth using images captured during a routine dental treatment. The panoramic or immersive photographs may be subsequently used by a dentist or other dental health care provider (HCP) to quickly become informed about a patient's status. Furthermore, a timed sequence of such photos that were created throughout years of dental treatment, may be used as a history log of a patient's dental status.

Such photo (or part thereof) created while a dental procedure is in session may be also used to identify the patient, in those cases were a panoramic and/or immersive photos (or parts thereof) of the patient from previous treatments exist. The photo (or part thereof) generated during a treatment may be compared to those previously recorded, and subsequently used for patient identification. If recognition of the patient being treated is achieved, the system may thereafter assign any photos and/or other information collected during the treatment to the patient, effectively selecting the patient's record.

An additional aspect of the invention is that the acquisition of images and other data used for the creation of panoramic or immersive photos may possibly be distributed among a plurality of HCPs and/or a plurality of sessions. As such, the invention described here allows for the generation of a panoramic and/or immersive photos to be performed in incremental steps.

The usage scenarios and embodiments are described to assist the understanding of the system and the methods that are later specified, and should not be viewed as limiting from other embodiments that do not depart from the spirit of this invention.

Figure 17A:
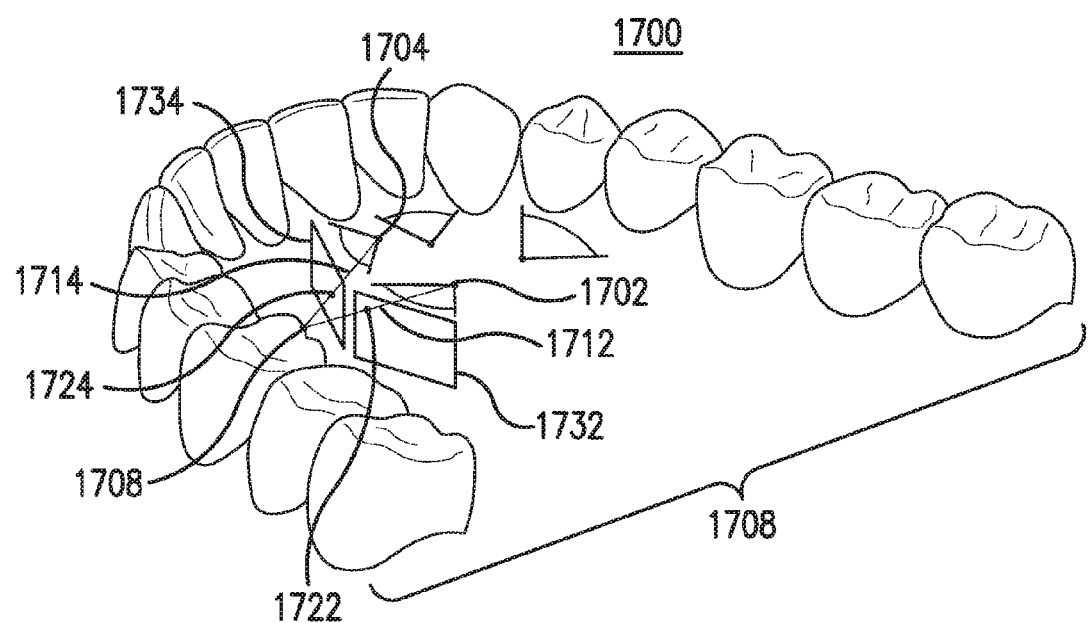
FIG. 17A is a diagram illustrating how a feature from the interior of a patient's mouth appears in different images taken from the intraoral mirror from different perspectives.

FIG. 17A is a diagram 1700 illustrating how a feature from the interior of the patient's mouth appears in different images taken from the intraoral mirror from different perspectives. In particular, diagram 1700 shows a patient's mouth 1708 and depicts how a camera takes images from different perspectives, shown for example by perspective 1702 and 1704. The image captured from perspective 1702 and 1704 are shown as photographic images 1732 and 1734 of the interior of a patient's mouth. Images 1732 and 1734 are associated with position information represented by perspective 1702 and 1704 respectively. Images 1732 and 1734 are collected from an image sensor affixed to a dental mirror and were taken such that at least a portion of images 1732 and 1734 overlap with one another.

A feature detection algorithm may be applied to identify features appearing in the overlapping portions of both images 1732 and 1734. Any type of feature detection algorithm may be used, including scale-invariant feature transform (SIFT) or speeded up robust features (SURF). In this way, a common feature was identified between images 1732 and 1734. The common feature appears at a point 1722 in image 1732 and at a point 1724 in image 1734.

Using points 1722 and 1724, a surface point may be determined. In particular, from the focal points of perspective 1702 and 1704, rays 1712 and 1714 may be extended to traverse points 1722 and 1724. Rays 1712 and 1714 may be extended according to a viewing angle at which the associated images 1732 and 1734 taken. The intersection of rays 1712 and 1714 is determined to be a surface point 1708.

Figure 17B:
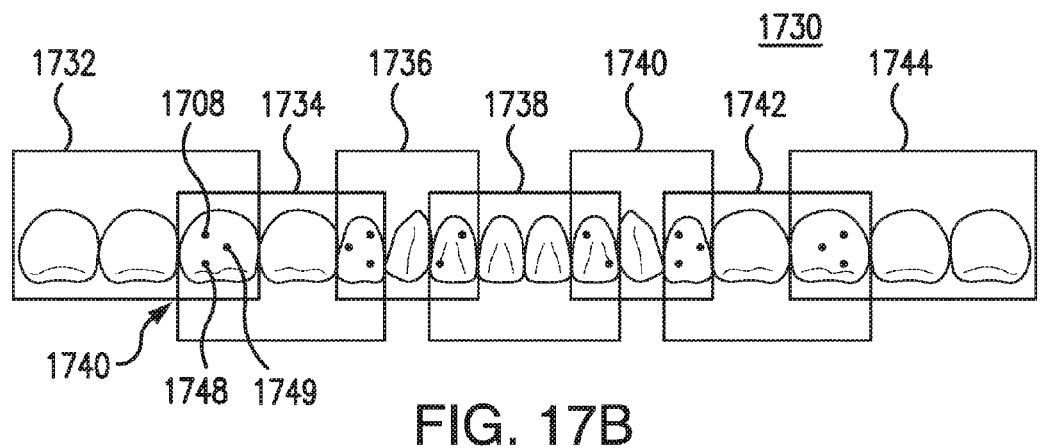
FIG. 17B is a diagram illustrating how the matched features are used to align the different images to be stitched into a panorama indicating a patient's dental status.

FIG. 17B is a diagram 1730 illustrating how the points generated from the matching features are used to align different images to be stitched into a panorama indicating a patient's dental status, according to an example embodiment. Diagram 1730 shows a plurality of images. In particular, diagram 1730 shows images 1732 and 1734 represented in FIG. 17A. In addition, diagram 1730 shows images 1736, 1738, 1740, 1742, and 1744.

Based on associated position information for the respective photographs and the matching features, images 1732, 1734, 1736, 1738, 1740, 1742, and 1744 are aligned to represent a series of adjacent teeth. In particular, images 1732-1744 may be adjusted such that the overlapping portions appear similar. The adjustment may be to account for variations in scale between images 1732-1744 such that the resulting panoramic image proportionally represents the patient's mouth. Images 1732-1744 are also arranged on a two dimensional plane so that overlapping portions of images 1732-1744 appear at similar positions. For example, images 1732 and 1734 have an overlapping portion 1740 that shows a number of features, including a feature 1748, a feature 1749, and the features used to deduce surface point 1708 in the point cloud determined as described above for FIG. 17A. Images 1732 and 1734 are scaled, positioned, and oriented such that feature 1748, feature 1749, and surface point 1708 appear at the same location on a two-dimensional grid. In this way, images 1732 and 1734 are registered to locations where they are aligned.

Figure 17C:
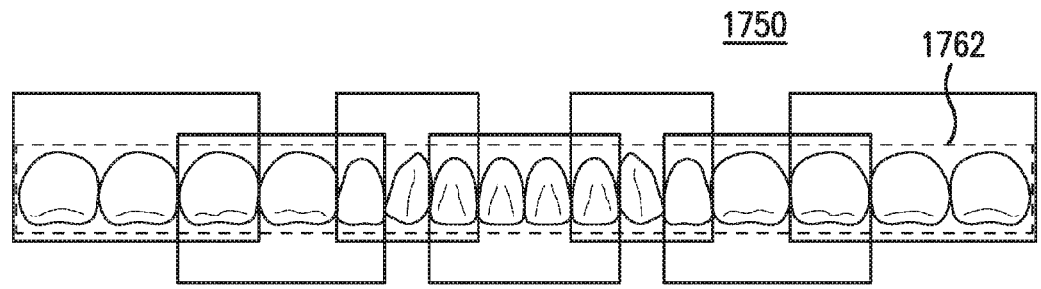
FIG. 17C is a diagram illustrating stitching the images captured from the image sensor into a panorama indicating the patient's dental status.

Once images 1732-1744 are aligned, they can be stitched together into a panorama as illustrated in FIG. 17C.

FIG. 17C is a diagram 1750 illustrating stitching the images captured from the image sensor into a panorama 1762 indicating the patient's dental status. Stitching the images together in this way may involve blending images. To blend the images, they may be adjusted to account for variations in brightness between the plurality of photographs such that the panoramic image 1762 has a substantially uniform brightness. In other words, the brightness is smoothed out across the image to avoid a blocky appearance and such that panoramic image 1762 appears to be a single photograph. In addition to adjusting brightness, the stitching may involve adjusting hue of the image again to avoid a blocky appearance and to make panoramic image 1762 appear as a single photograph.

Such panorama images can be created for various surfaces of a patient's teeth. Front, top and back for the upper and lower teeth (facial/buccal, palatal/lingual, inscisal/occlusal).

Once the panorama image 1762 is created, different points on panoramic image 1762 may be associated with different medical observations. For example, the history of each tooth may be recorded separately, associated with the position of the tooth and panoramic image 1762. This may involve associating a point on panoramic image 1762 to another image representing the same location in the patient's mouth. The other image may for example be an x-ray image.

Figure 18A:
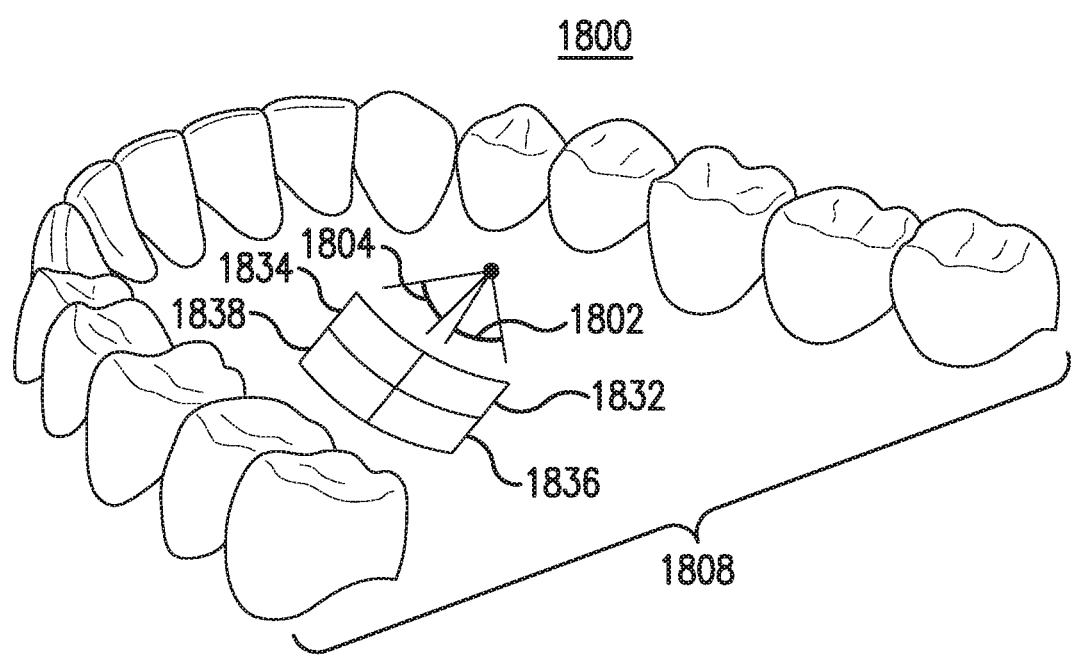
FIGS. 18A-C are diagrams illustrating how to capture an immersive panorama and render it with a sense of depth.

FIG. 18A illustrates a diagram 1800 showing images captured at various angles out of the same location inside the patient's mouth. In particular, diagram 1800 shows a patient's mouth 1808 and depicts how a camera takes images from the same location but at different angles, shown for example by perspective 1802 and 1804. The image captured from perspective 1802 and 1804 are shown as photographic images 1832 and 1834 of the interior of a patient's mouth. Images 1832 and 1834 are associated with the angle represented by perspective 1802 and 1804 respectively. Images 1832 and 1834 are collected from an image sensor affixed to a dental mirror and were taken such that at least a portion of images 1832 and 1834 overlap with one another.

Figure 18B:
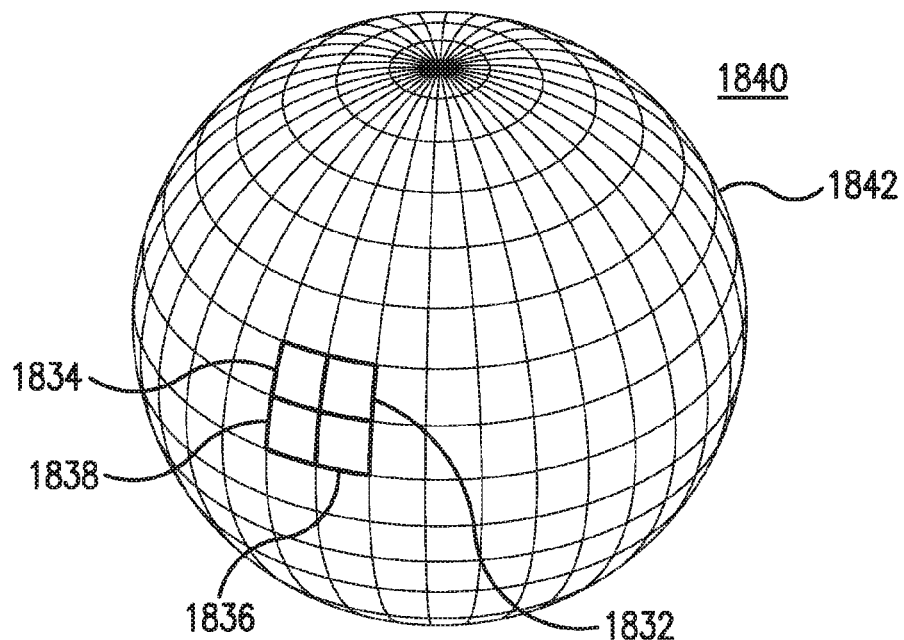

Based on associated position information for the respective photographs and the matching features, images 1832, 1834, 1836, and 1838 are mapped into a sphere, each according to the angle which it was captured, relative to the center of the sphere which represents the image sensor location, as shown in FIG. 18B.

FIG. 18B shows a diagram 1840 with a sphere 1842 with pixels from images 1832, 1834, 1836, and 1838 mapped to it. Using the sphere 1842, an image can be rendered to the user that provides a sense of depth, as illustrated in FIG. 18C.

Figure 18C:
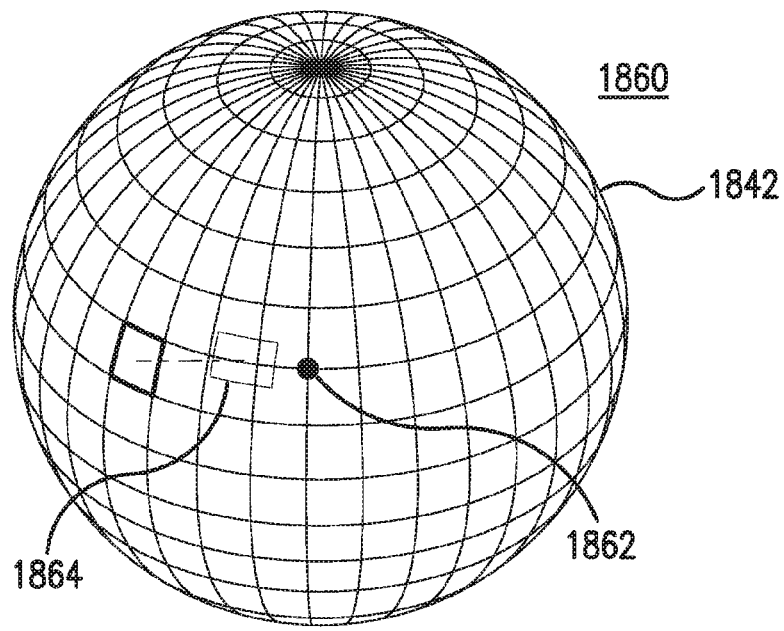

FIG. 18C shows a diagram 1860 illustrating the geometry for rendering of such an immersive photograph, where a virtual camera 1862 for the purpose of rendering is placed at the center of the sphere. A healthcare provider chooses an angle for the virtual camera and accordingly a viewport 1864 is determined. The pixels of the sphere are mapped into viewport 1864 to produce an image for display. A healthcare provider may them choose to "rotate" the camera around the center point, rotating the viewport as well for displaying various angles of the mouth around the same center point.

Multiple such spheres are created, with center points in various locations inside the patient's mouth, allowing a healthcare provider to choose the position of the center point, and hence the position within the mouth he is interested in, for locating the virtual camera.

When the virtual camera changes perspective, a different sphere 1804 is selected or a different portion of the sphere 1804 is mapped to viewport 1802, resulting in rendering a different subject matter from the immersive image.

E. Utilizing an Intraoral Mirror to Generate a Dental Impression

In additional to generating a dental status, embodiments generate highly accurate digital dental 3D impressions, even in the case where the source for depth measurements are images. It generates the digital dental 3D impressions without requiring a dentist (or other health care provider) to dedicate an extended period of time for the intraoral data acquisition. Instead of requiring a dedicated acquisition session, the data needed to generate the impression is collected during a routine dental treatment. In addition, the data may be collected over the course of a plurality of patient visits to one or more health care providers.

As shown in FIG. 17A, using points 1722 and 1724, a location of a surface point 1708 in an object captured by two or more images may be determined. In particular, measuring the distance between focal points of perspective 1702 and 1704, and extracting the angles of rays 1712 and 1714 enables to calculate the measures of the triangle with edges 1722, 1724 and 1708, hence the location of surface point 1708. A plurality of surface points located on objects inside the patient's mouth is thereafter used to create a three dimensional mesh model of the mouth. Other methods of determining the location of surface points of an object, for example measuring the time-of-flight of radiation, such as LIDAR, or shape from shadow may also be used.

The amount of shadow casted by an object is generally related to the topography of the object. When determining the shape of objects in the mouth, the shadow that objects cast, as recorded in a two-dimensional image, may provide information about their three-dimensional shape. To collect data in order to generate 3-D impressions employing a technique referred to as shape-from-shadow, embodiments include varying illumination image capturing as illustrated in FIGS. 19A and 19B.

Figure 19A:
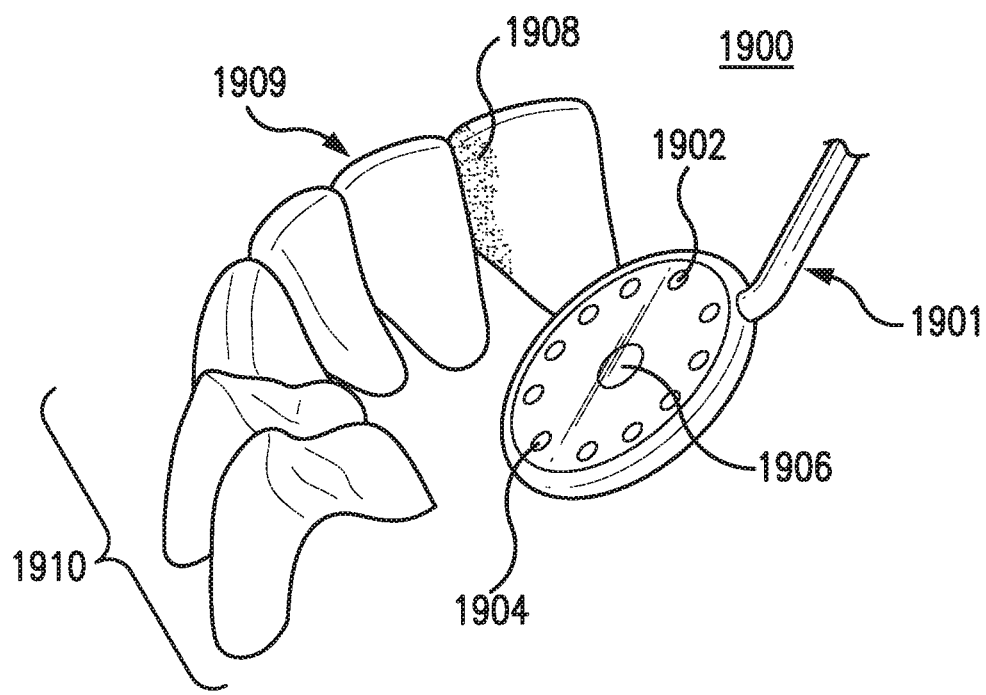
FIGS. 19A and 19B are diagrams illustrating how varying illumination from the intraoral mirror can provide information on the three-dimensional shape of a patient's teeth.

FIGS. 19A and B are diagrams illustrating how varying illumination from the intraoral mirror can provide information on the three-dimensional shape of a patient's teeth. FIG. 19A shows a diagram 1900 with a smart mirror device 1901. Smart mirror device 1901 has an image sensor 1906 at its center and a plurality of light sources at its perimeter. The plurality of light sources include a light source 1902 and, opposite to light source 1902, a light source 1904. Smart mirror device 1901 is positioned to capture an image of a patient's teeth 1910, in particular a tooth 1909.

In diagram 1900, light source 1904 is illuminated, while light source 1902 is not. Because of the varying illumination, tooth 1909 casts a shadow 1908. Image sensor 1906 captures an image, including both tooth 1909 and shadow 1908. From the image, information about tooth 1909's three-dimensional shape can be determined. In particular, brightness of the image can be analyzed to determine where shadow 1908 is located. The location of an image that occupies shadow 1908 is obscured by the 3D shape of teeth 1910 from the perspective of light source 1904, while the remainder of the image is not.

Figure 19B:
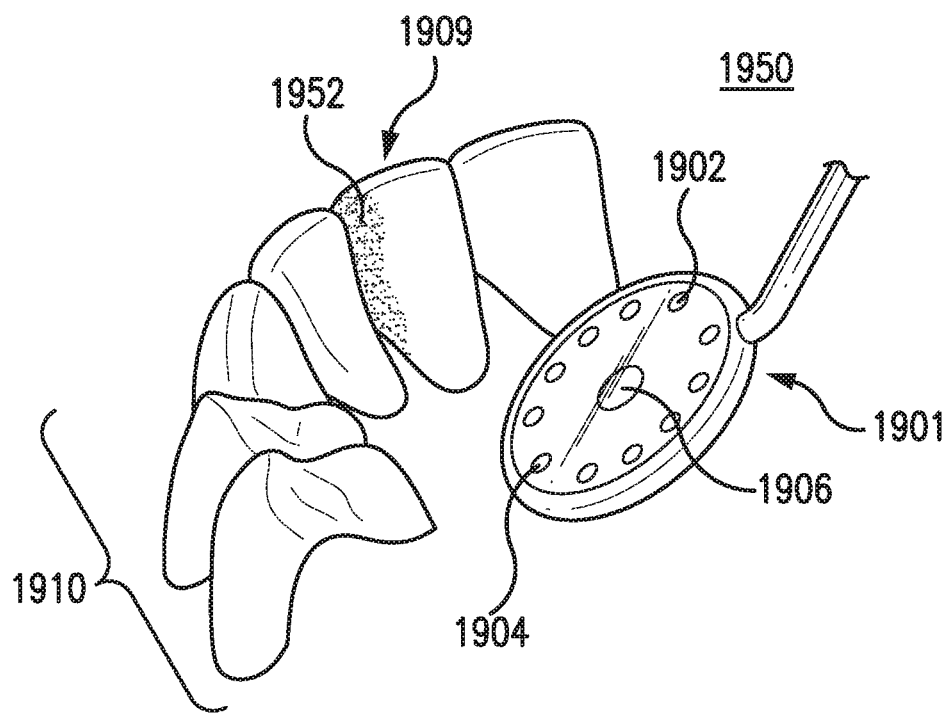

FIG. 19B shows a diagram 1950 illustrating smart mirror device 1901 illuminated differently from diagram 1900 in FIG. 19A. In diagrams 1900 and 1950, smart mirror device 1901 has substantially the same position and orientation with respect to teeth 1910. In diagram 1900, light source 1904 is illuminated while light source 1902 is not. But in diagram 1950, the opposite is true: light source 1902 is illuminated while light source 1904 is not. The different illumination casts a different shadow 1952 on tooth 1909. Again, from shadow 1952, shape information is determined. The location of an image that occupies shadow 1952 is obscured by the 3D shape of teeth 1910 from the perspective of light source 1902, while the remainder of the image is not.

Illumination between the various light sources may vary quickly, too quickly for the human eye to detect. As the illumination varies, shape information may be aggregated to generate a mesh of the surface points representing the surface of a patient's mouth, and in particular of teeth 1910. Additionally or alternatively, the light sources may emit light outside the visible spectrum, such as infrared light. And the shadows detected may be shadows in this invisible light spectrum.

F. Incremental Generation of Status and Impression

Position information acquired in a smart mirror device and associated to captured images assists in the positioning of images, for example in order to align them during a stitching process. The associated position information is a value relative to a reference point, that is calibrated from time to time as described in FIG. 5A. Moreover, captured images of the same patient that were acquired by different healthcare providers in different dental office rooms, would exhibit position information values each relative to a different reference point. In order to use images captured in various sessions, an alignment to the position of images must be determined.

Figure 20:
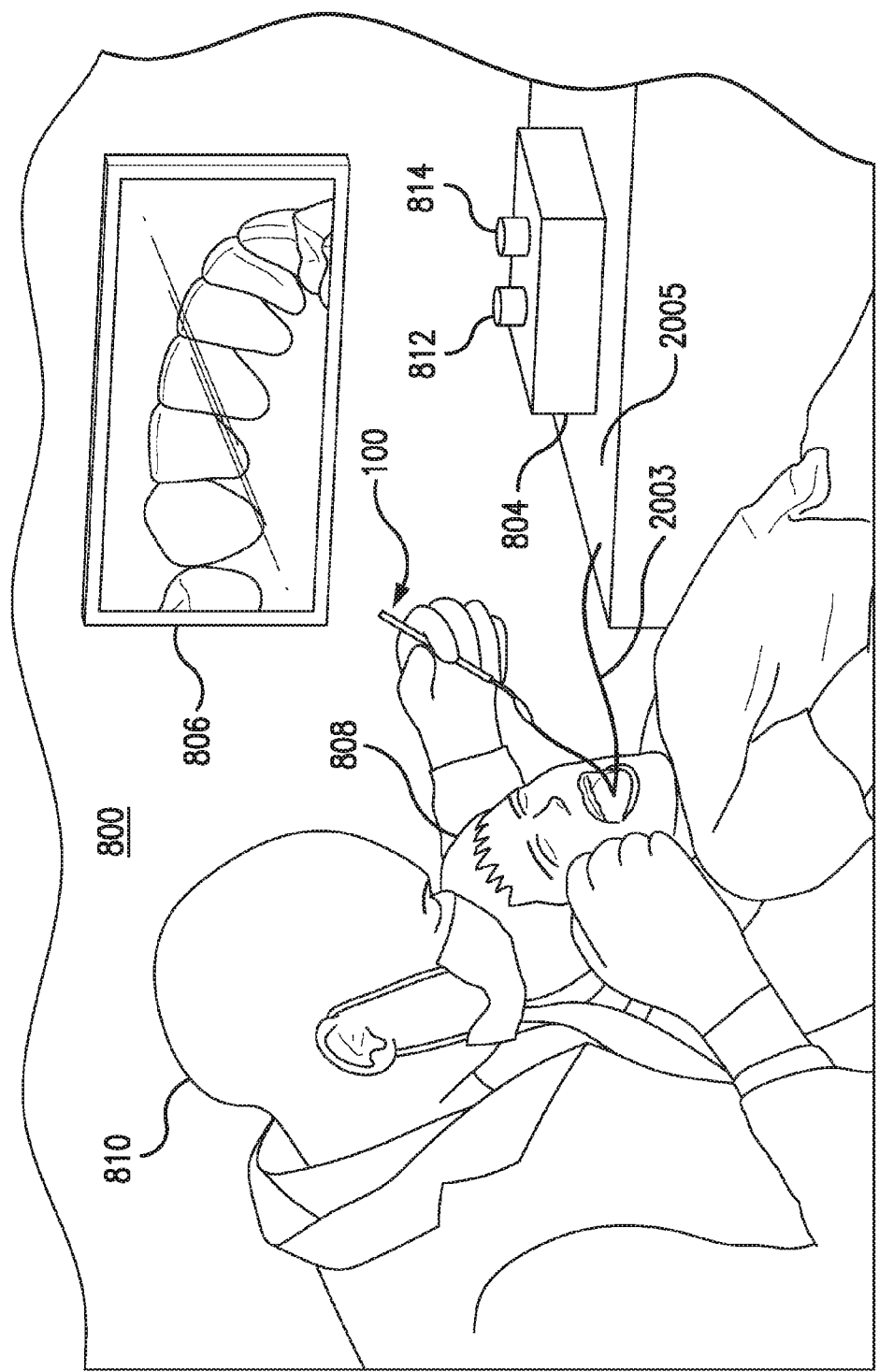
FIG. 20 is a diagram illustrating how a smart mirror device may be moved during a procedure.

FIG. 20 illustrating a method for aligning the position information acquired in one session to the position information acquired in another session. Thereafter the aligned information is used for generating a patient status or impression.

In some aspects of the invention, during a treatment, an HCP shifts the smart mirror, for example, from a tray into the leftmost area in a patient's mouth, then about the oral cavity, and back to the tray. This example is illustrated in FIG. 20 on a diagram illustrating a path 2003, an imaginary line tracking a route of a smart mirror 100 from a tray 2005, into the mouth of a patient 808, around the oral cavity and out of the mouth. The relative position of the smart mirror is calculated, for example, by integrating acceleration measurements over time. The result is a set of position measurements that include a relative position and their corresponding time. The human oral cavity is within limited dimensions. When a smart mirror is inserted to the oral cavity, it must pass through the mouth, an opening that is within certain dimensions. We shall call the elements of interest, an oral cavity, the mouth opening and the like as volume elements.

Figure 21A:
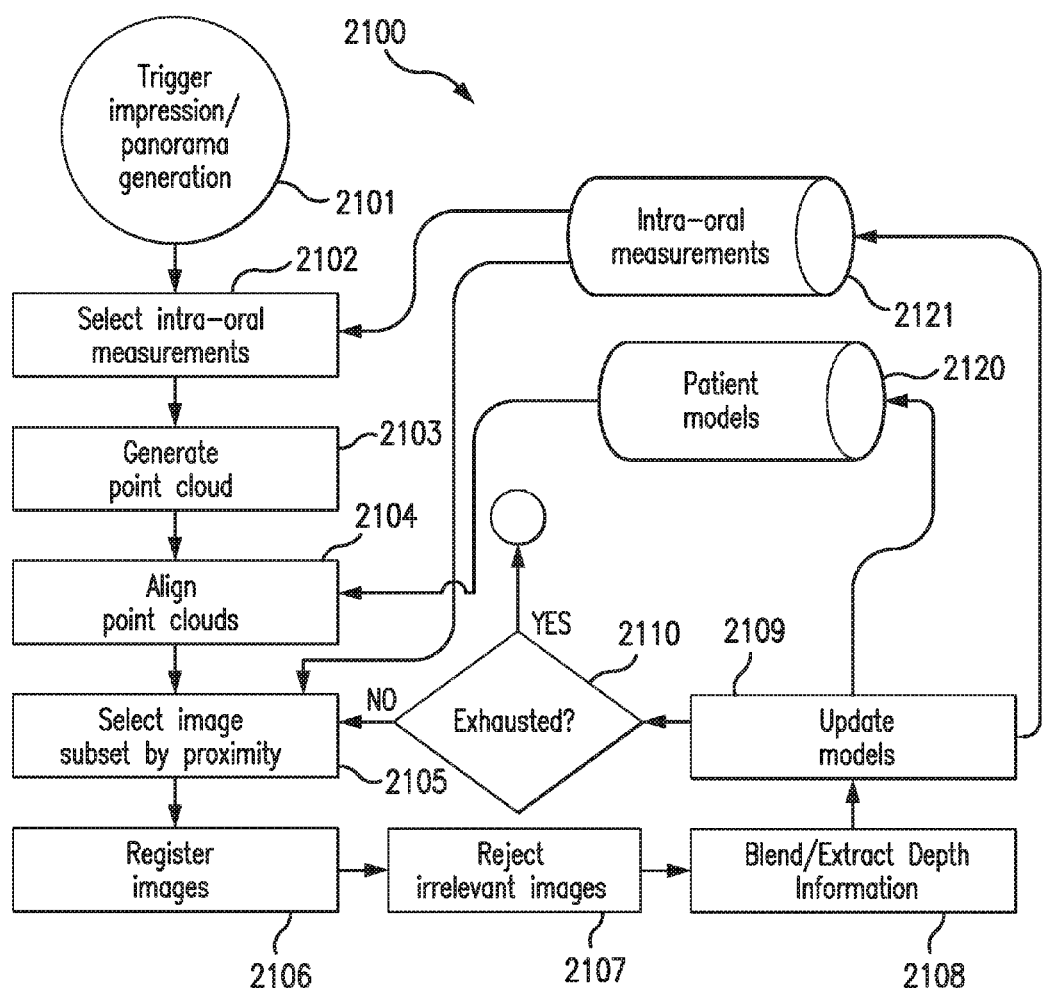
FIGS. 21A-B are flowcharts illustrating a method for incremental generation of a dental status and impressions.
Figure 21B:
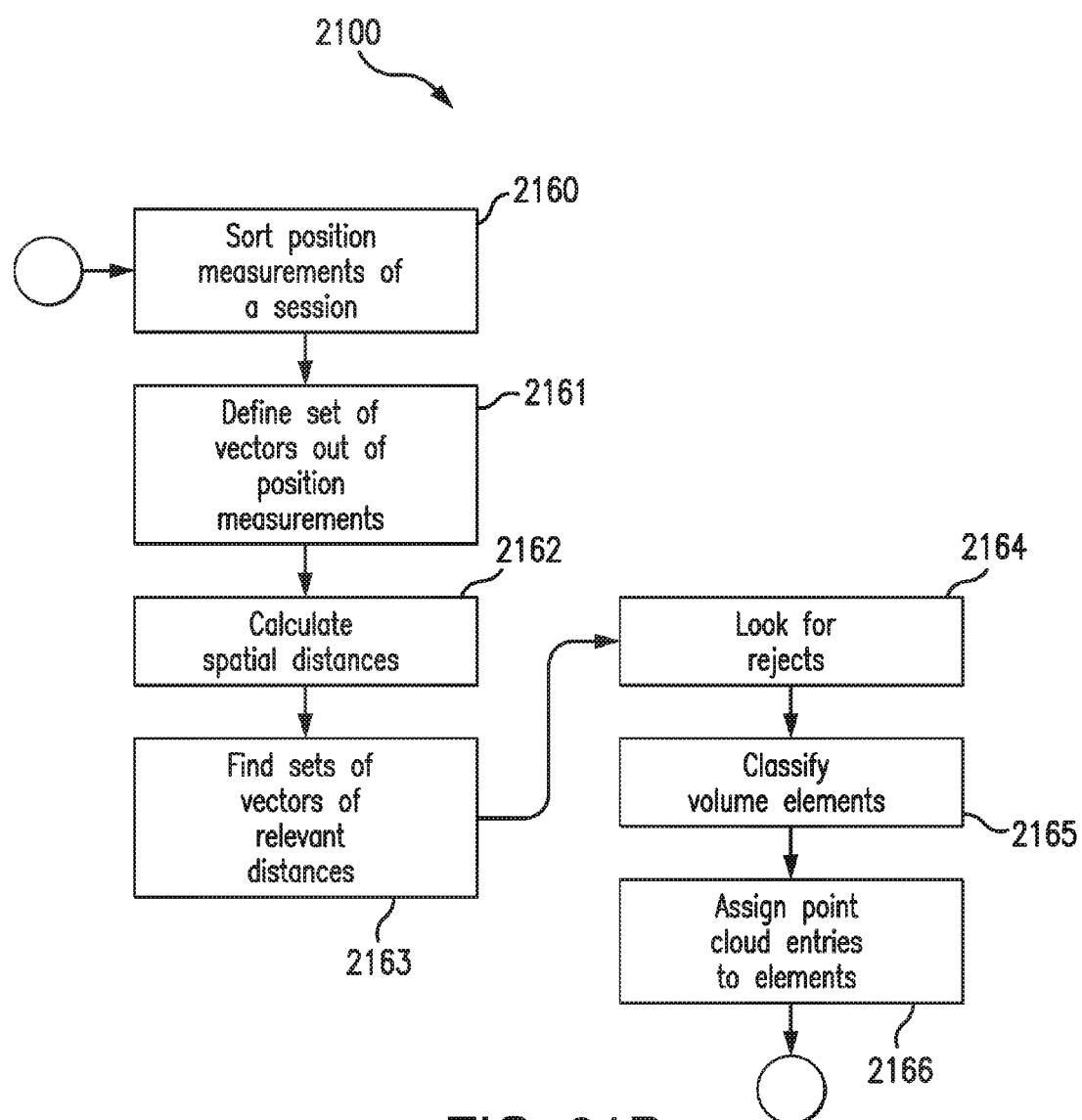

FIGS. 21A-B are flowcharts illustrating a method for aligning the position information acquired in a session to the position information acquired in a previous one or more sessions. They do so by analyzing point clouds of position measurements in order to identify and align volume elements, followed by a finer alignment using feature detection in overlapping images. The aligned position information is then merged into one, incrementally generated point cloud model. Thereafter the point cloud model is used for generating an incrementally updated patient status or impression models.

At step 2101, the process is initiated. In some embodiments, the initiation of the process 2100 is triggered when a server is idle, or when a server's resource utilization (computational power, memory, I/O, etc) becomes small enough, below a certain threshold. In some embodiments, the initiation of the process 2100 is triggered by a clock. In some embodiments, the initiation of the process 2100 is triggered by a user request. In some embodiments, the initiation of the photo generation is otherwise triggered, the invention is not so limited.

At step 2102, a set of intraoral images and a set of supplementary data stored in an intraoral measurements database 2121 is selected for the purpose of creating or updating a model. In some embodiments, the set comprises some or all of the images and supplementary data that were captured in a single treatment session performed by an HCP, for example, as indicated in step 1007 of process 1000 (FIG. 10). In some embodiments, the set is comprised of some or even possibly all of the images and/or some or even possibly all of the supplementary data pertaining to the same patient, and being captured in a plurality of intraoral procedures, performed by one or more HCPs.

At step 2103, a point cloud is generated for the images and/or supplementary data. A point cloud represents a collection of positions and possibly also corresponding rotations. In some embodiments, a subset of the set of supplementary data (that was selected at step 2102) is used to generate a point cloud. In some embodiments, each element in a point cloud corresponds to a time on which an image was captured. The point cloud may be acquired as described above for FIG. 20.

At step 2104, the point cloud generated in step 2103 (we shall call it: new point cloud), or part thereof, is aligned to a point cloud, or part thereof, generated in one or more previous sessions (we shall call it: previous point cloud) which is retrieved from a patient models database, see also the process of FIG. 21B. FIG. 21B details some of the sub-steps of step 2104 of FIG. 21A. FIG. 21B details the analysis of the point cloud in order to find volume elements and classify points (positions) into these volume elements. Once done, the volume elements can be aligned to the database model. For example, a volume element that is determined to be the opening of a mouth is found. Then, the mouth opening is aligned to one already found from previous sessions. In some embodiments, following an alignment, the new point cloud is merged to a previous point cloud. By combining point clouds, the resulting combined cloud may be less noisy and more accurate or may cover a greater portion of the patient's mouth.

At step 2105, images of objects of a spatial proximity are selected. In some embodiments, one or more of said images are selected from the set of intraoral images (of step 2102). In some embodiments, one or more of said images are selected from the set of intraoral measurements database 2121 (hence may have been captured in one or more treatment sessions). In some embodiments, spatial proximity is determined by reference to the merged point cloud of step 2104. In some embodiments, spatial proximity is determined by matching features detected in a plurality of images, using image analysis methods. Matching features in images of spatial proximity are illustrated in FIG. 17A.

At step 2106, images are registered, so that image alignment is reached. When the images are captured, they may differ in scale and perspective. During registration, the images are adjusted to align the images so that the same object appears the substantially same in overlapping portions of adjacent images. This may involve changing the image's scale or perspective, or correcting for any distortions. An example of how various images are aligned is depicted above for FIG. 17B.

At step 2107, irrelevant images are discarded. In some embodiments, irrelevant images include images that failed registration. In some embodiments, irrelevant images include images that do not show objects of interest. In some embodiments, irrelevant images includes images of lesser quality. It may be appreciated by those skilled in the art that there are other reasons to classify images as irrelevant, the invention is not so limited.

At step 2108, when updating status, an image is blended to a panoramic image and/or to an immersive photo. In some embodiments, blending includes the smoothing of illumination (brightness) or hue among adjacent images. An example of blending is illustrated above in FIG. 17C.

Also, at step 2108, when updating an impression, depth information is extracted using images in spatial proximity, and merged into the impression model. In some embodiments, images that have spatial proximity as well as a similar rotation are used to extract depth information. In some embodiments, said set of images vary in the illumination conditions present at the time of capture, so that such images show a variation in the shadows that intra-oral objects cast, effectively encoding the shape of the object, from the respective image capture pose (defined as a position and an orientation at time of image capture). Therefore a plurality of poses encode shape information from a plurality of directions, rendering a three dimensional model of an object. An example of varying illumination for capturing images is illustrated above with respect to FIGS. 19A and 19B

At step 2109, the achieved models, and/or photos, or part thereof, are stored into a patient's models database 2120. In some embodiments, model information includes the calculations and/or transformations to be applied on a captured imaged to fit into a photo.

At step 2110, if the processing of images and/or supplementary data is exhausted, the process exits. Otherwise, it iteratively continues to step 2105.

In some embodiments, additional conditions may cause process 2150 to exit or pause, for example, the server might become busy with other tasks of higher priority, or following the elapse of a time interval allocated for the process and the like.

FIG. 21B is a flow diagram illustrating a process 2100 for classifying positions by volume elements. In some embodiments, such classification is a step in aligning point clouds by aligning volume elements defined on the point clouds.

At step 2160, a set of positions and possibly direction (which may be included in a point cloud) are sorted according to time. The set is comprised of measurements from a single session or part thereof, such that, during the time period, the patient's mouth and oral cavity are at about the same position.

At step 2161, a set of vectors is defined. Each vector is based on two or more temporally consecutive position measurements. Thereafter a vector defines a line segment in space, and possibly also a direction (the direction would be, for example, an approximate direction of motion).

At step 2162, the spatial distances between vectors in a set are calculated. In some instances, the spatial distance is the smallest possible distance between any two points, each point on one of the vectors. In some embodiments, the spatial distance is the distance on a plane intersecting with the two vectors (when such intersection exists). In some embodiments, the spatial distance is the distance between the midpoints of the vectors. In some embodiments, the spatial distance is the distance between the first or last points of the vectors. It may be appreciated by those skilled in the art that other possibilities to define a distance between vectors may be used without departing from the spirit of the invention.

At step 2163, a plurality of sub-sets from the vector set are found, each sub-set includes all vectors in the set such that their distances are smaller (and maybe also equal) than a higher limit, and possibly also larger (and maybe also equal) than a lower limit. The limit, for example, may represents the largest opening of a human mouth, or, for example, represents the largest diameter of a human oral cavity or, for example, represents a small volume indicating that the instrument is at rest (i.e. on a dental tray), and the like. Thereby, each subset may represent one or more volume elements. Each representation of a volume element by a sub-set shall be called a solution.

At step 2164, one or more of the solutions are rejected. In some embodiments, a solution is rejected if there exists a vector that is not in the respective sub-set but would have been included in the sub-set if the higher limit was larger, and/or the lower limit was smaller. In some embodiments, a solution is rejected if it is in proximity to another solution and/or subset. In some embodiments, a solution is rejected if it is not in proximity to another solution and/or subset. In some embodiments, a subset is rejected based on image analysis, for example, a sub-set corresponds to a possible oral cavity, but the respective captured images do not show intraoral visual characteristics (i.e. colors in some area, color histogram, dynamic range, objects etc.). It may be appreciated by those skilled in the art that other possibilities to reject a solution and/or a sub-set may be used without departing from the spirit of the invention.

At step 2165, the appropriate solutions are selected as a representation of volume elements, thereby defining volume elements on the point cloud.

Thereafter, at step 2166, points of the point cloud can be assigned to volume elements, thus it can be determined for a point of the point cloud if it is inside the volume element, for example the oral cavity, or it is not.

G. System to Generate a Patient Status and Dental Impression

Generating the dental impression or generating the patient status may require significant computing power. For example, depth measurement extraction and image registration may require significant memory or processing power. To deal with this, embodiments separate the impression and status generation from the data acquisition. In particular, the data may be acquired using a smart mirror device and base station in a dental office, and the base station may transmit the data to a remote server for processing as illustrated in FIG. 22.

Figure 22:
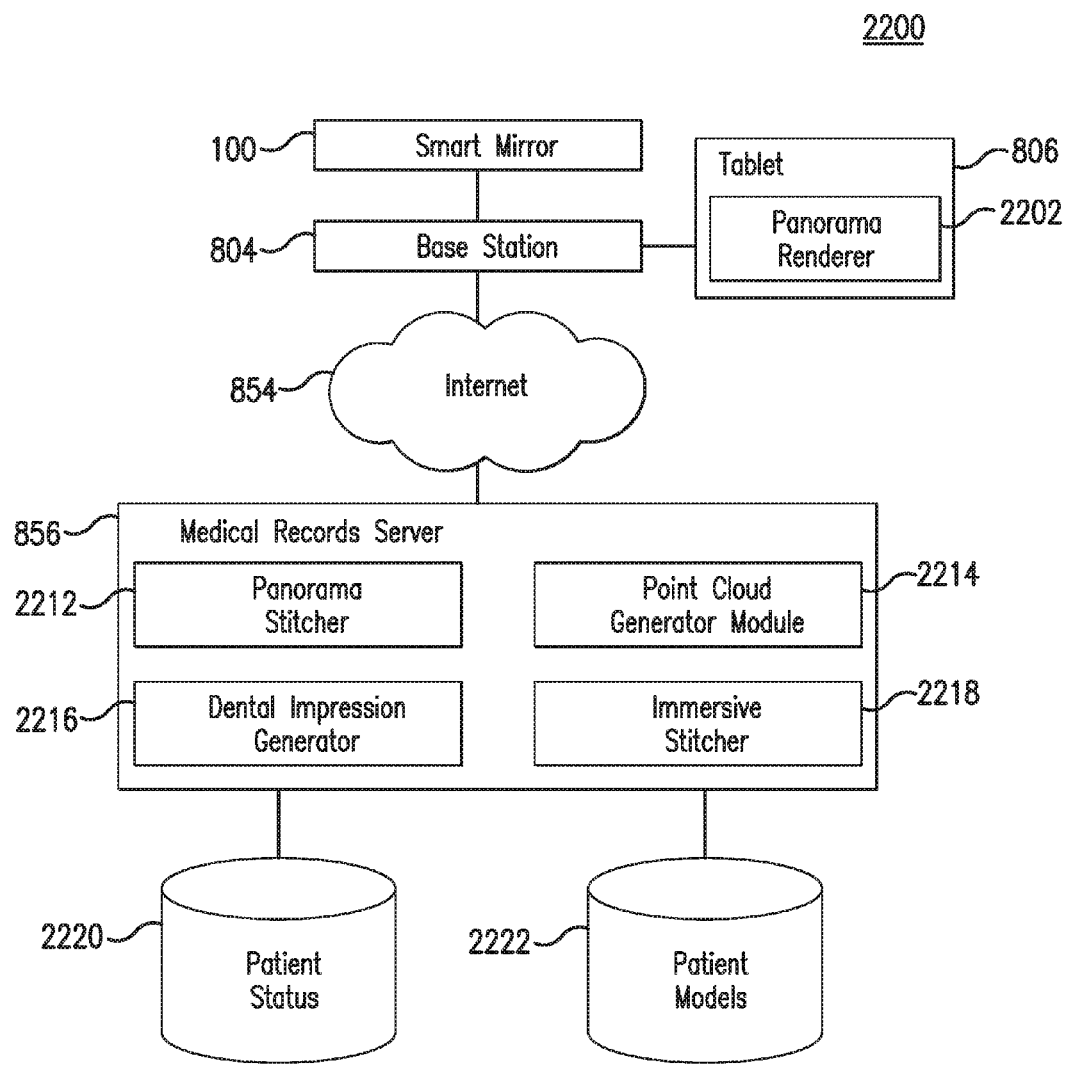
FIG. 22 illustrates a system with a server to stitch panoramas indicating a patient's dental status and to generate dental impressions.

FIG. 22 illustrates a system 2200 with a server to stitch panoramas and immersive photographs indicating a patient's dental status and to generate dental impressions.

Like the system in FIG. 8, system 2200 includes smart mirror device 100, tablet 806, and base station 804, which is connected by one or more networks 854 to medical records server 856. The records server 856 includes a panorama stitcher module 2212, a point cloud generator module 2214, a dental impression generator module 2216, and an immersive photograph stitcher module 2218. Medical records server 856 is also coupled to a patient status database 2220 and patient model database 2222.

Medical records server 856 receives (i) a plurality of photographs of the interior of the patient's mouth, (ii) associated position information for the respective photographs, and (iii) information describing how the respective photographs were illuminated. The plurality of photographs are collected from an image sensor affixed to a dental mirror and overlap at least in part with another one of the plurality of photographs. Once collected, they are stored in measurements database 2220.

Point cloud generator module 2214 generates a point cloud from position information and aligns it to previously generated point clouds, to allow the alignment of images captured at different dental sessions. Point cloud generator module 2214 may operate as described above with respect to FIG. 20, 21.

Panorama stitcher module 2212 determines features in the overlapping portions that match between multiple photographs. Based on associated position information for the respective photographs and the matching features, panorama stitcher module 2212 aligns the plurality of photographs to represent a series of adjacent teeth. Finally, panorama stitcher module 2212 stitches the plurality of photographs of the interior of the patient's mouth into a panoramic image representing a state of at least a portion of the patient's mouth. Panorama stitcher module 2212 may operate as described above with respect to FIGS. 17A-C.

Once generated, panorama stitcher module 2212 stores the panoramic image into patient model database 2222. Patient model database 2222 stores historical patient status information including historical panoramic images of a patient's mouth. Patient model database 2222 may correlate portions of the panoramic images with the each other and with other images of a similar area of the patient's mouth. The other images may, for example, be x-ray images.

Once generated and stored, the panoramic images may be retrieved for display. For example, the panoramic images may be displayed on tablet 806, perhaps using a user interface application (not shown).

Immersive photograph stitcher module 2218 determines features in the overlapping portions that match between multiple photographs captured at various angles out of the same center point position. Based on associated position information for the respective photographs and the matching features, immersive photograph stitcher module 2218 maps the plurality of photographs onto the shape of a sphere. Then, Immersive photograph stitcher module 2218 stitches the plurality of photographs of the interior of the patient's mouth into an immersive image representing the captured images around the center point. Finally, Immersive photograph stitcher module 2218 organizes multiple such spheres according to their center point, mapping positions in the patient's mouth to spheres. Immersive photograph stitcher module 2218 may operate as described above with respect to FIGS. 18A-C.

Once generated, Immersive photograph stitcher module 2218 stores the immersive photograph into patient model database 2222. Patient model database 2222 stores historical patient model information including historical immersive images of a patient's mouth. Patient model database 2222 may correlate portions of the immersive images with the each other and with other images of a similar area of the patient's mouth. The other images may, for example, be x-ray images.

Once generated and stored, the immersive images may be retrieved for display. For example, the immersive images may be displayed on tablet 806, perhaps using a user interface application (not shown).

Not only can medical records server 856 generate a panorama indicating patient status, and immersive photographs, medical records server 856 can also generate a dental impression. To generate a dental impression, medical records server 856 uses dental impression generator 2216 that determines points on the surface of objects in the mouth, for example as shown in FIG. 17A and it may also use image analysis techniques, including the shape from shadow techniques, discussed above.

From the surface points, dental impression generator 2216 generates a dental impression of the patient's mouth. The dental impression may be a three-dimensional mesh fit to the surface points.

In this way, using an intraoral mirror with an integrated camera, a three dimensional dental impression may be generated following a routine dental examination. The dental impression may be used, for example, for prosthodontics (such as making dentures, inlays and plastic casts), orthodontics, restorative dentistry (e.g. to make impressions of teeth which have been prepared to receive indirect extracoronal restorations such as crowns or bridges), maxillofacial prosthetics (prosthetic rehabilitation of intraoral and extra-oral defects due to trauma, congenital defects, and surgical resection of tumors) restorative, diagnosis and oral and maxillofacial surgery for both intra oral and or extra-oral aims (e.g. dental implants).

H. Illuminating The Patient'S Mouth

As described above, the intraoral mirror may have a plurality of light sources. How the light sources are controlled is described below with respect to FIGS. 23 and 24.

Figure 23:
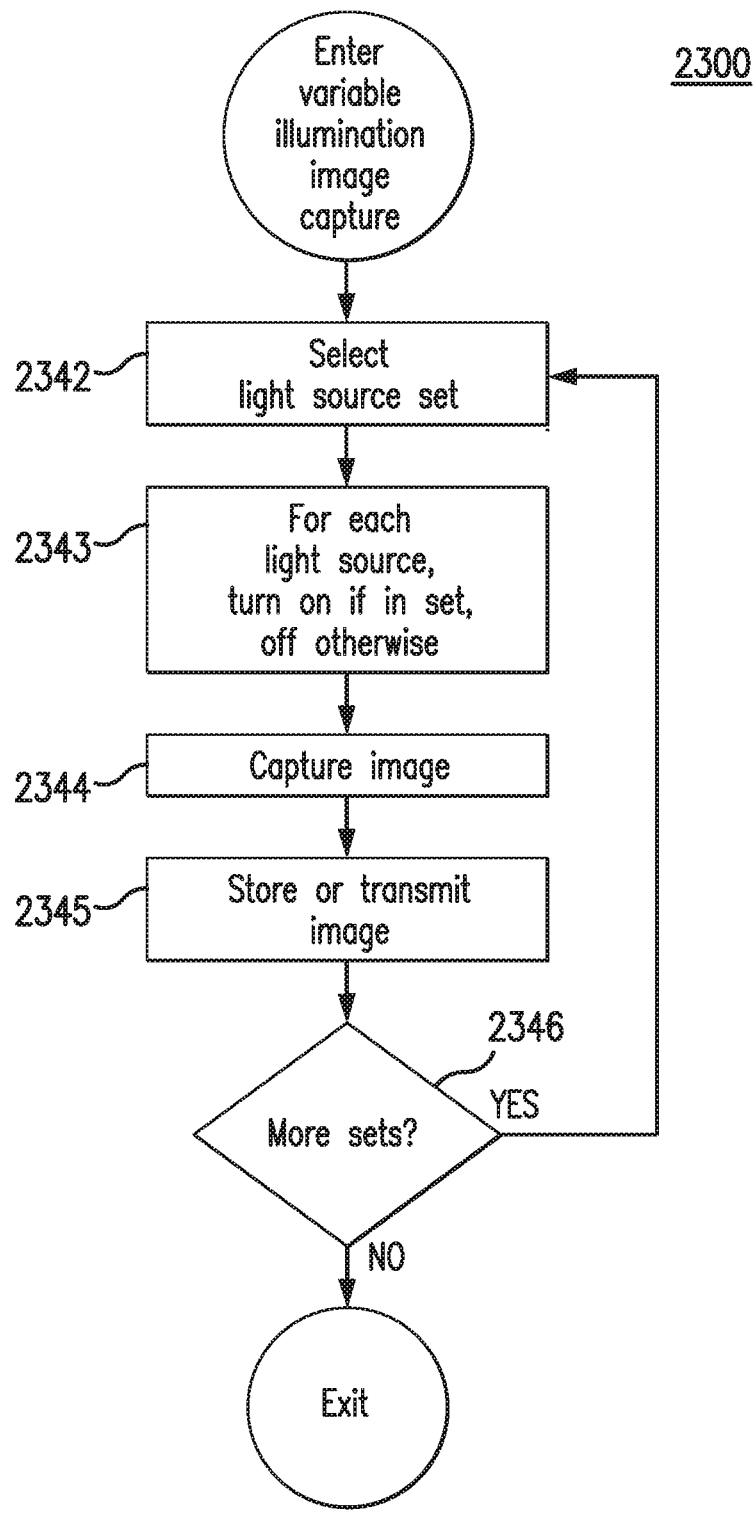
FIG. 23 illustrates a method for varying illumination of the intraoral mirror.

FIG. 23 illustrates a method 2300 for setting illumination of an intraoral mirror with an integrated camera.

At step 2342, a set of light sources out of a plurality of light source components are selected. At step 2343, each light source in the set is activated (set to illuminate), and all other light sources are deactivated (set to not illuminate). At step 2344, one or more images are captured. At step 2345, the one or more images are stored in memory or transmitted to a remote computational device. At step 2346, there is a check whether more sets of source light are required, and if so the capture process repeats with the new set.

The above process produces a set of images including (more or less) the same objects but with various settings of illumination. As a result, the (more or less) same objects include different shadows and/or shading, which may allow production of an image with an improved visual quality, and/or reconstruct a 3-dimensional model of the object using so-called shape from shadow (or shape from shading) techniques. Particularly, in a person's intraoral environment, such sets of images captured with a smart mirror are characterized by the object of interest being in a relatively close proximity to the image capturing device and in an embodiment where a plurality of light source are located on the perimeter of a round mirror, due to such geometry, the shadows of such objects can be expected to be of enough difference to be conducive to such processes. In some embodiments, the intensity of illumination may also vary among the light source sets.

Figure 24:
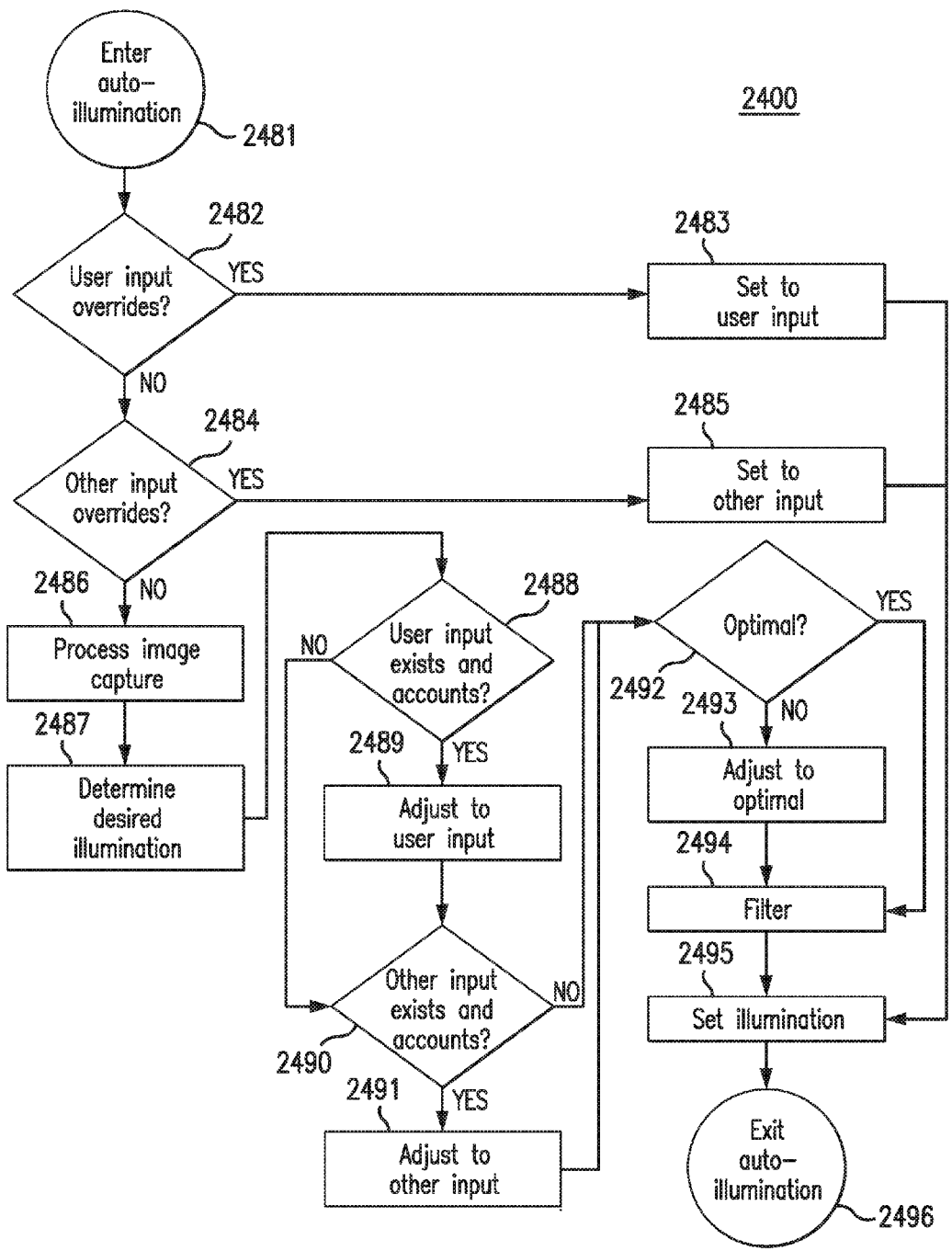
FIG. 24 illustrates a method for automatically adjusting illumination originating from the intraoral mirror.

FIG. 24 illustrates a process 2400 for adjusting illumination originating from the intraoral mirror.

At step 2482, whether the user can override the illumination intensity is determined. This may be set for example, in a user profile or configuration file. If a user overrides the illumination, process 2400 proceeds to steps 2483 and 2495. At step 2483, the intensity value is set according to the user's request. At step 2495, one or more light sources are set to illuminate and/or not illuminate respectively. In some embodiments, a user sets a required intensity using a user interface input/output control of smart mirror, for example a button or knob. In some embodiments, a user sets a required intensity using a voice request. In some embodiments, a user sets a required intensity using a predefined configuration. In some embodiments, a user sets a required intensity using a remote computational device.

If a user cannot override, process 2400 proceeds to step 2484, where process 2400 checks whether another input overrides the illumination, for example an override can be generated by another software process (for example a process that requires control of illumination, such as illustrated in process 2300, FIG. 23). If so, process 2400 proceeds to steps 2485 and 2495. At step 2485, the intensity value is set according to said request.

If neither a user nor other input overrides the illumination, process 2400 proceeds to step 2486. At step 2486, the capturing and image processing of one or more images is performed to establish a desired illumination intensity for a one or more light sources. Such processing may include, but is not limited to, identifying areas of an image that have an intensity above or below a threshold, estimating from images or receiving saturation and/or blooming data from an imaging sensor, comparing a plurality of images possibly with variable illumination and the like.

At step 2487, the desired illumination is calculated. This may involve increasing intensity when an image captured and processed at step 2486 is determined to be too dark and decreasing intensity when an image captured and processed at step 2486 is determined to be too light. The desired illumination may vary by light source. For example, if at step 2486, a particular area of the image is determined to be darker than the rest, a light source in proximity to the area may increase in intensity. Conversely, at step 2486, a particular area of the image is determined to be lighter than the rest, a light source in proximity to the area may decrease in intensity.

At step 2489, the calculated value is adjusted according to a user input, if such input exists and is selected to affect the illumination, a condition checked at step 2488. At step 2491, the calculated value is adjusted according to another input, if such input exists and is selected to affect the illumination, a condition checked at step 2490. At step 2492, it is checked if the existing illumination is different than the optimal and if so it is adjusted (at step 2493). At step 2494, the result is filtered, so that changes in illumination are gradually introduced. At step 2495, the illumination intensity of one or more light sources are set.

In this way, light sources on an intraoral mirror with an integrated camera can be variably and automatically controlled to adjust for variations in lighting.

I. Monitoring Usage of the Intraoral Mirror to Conserve Power

Figure 25:
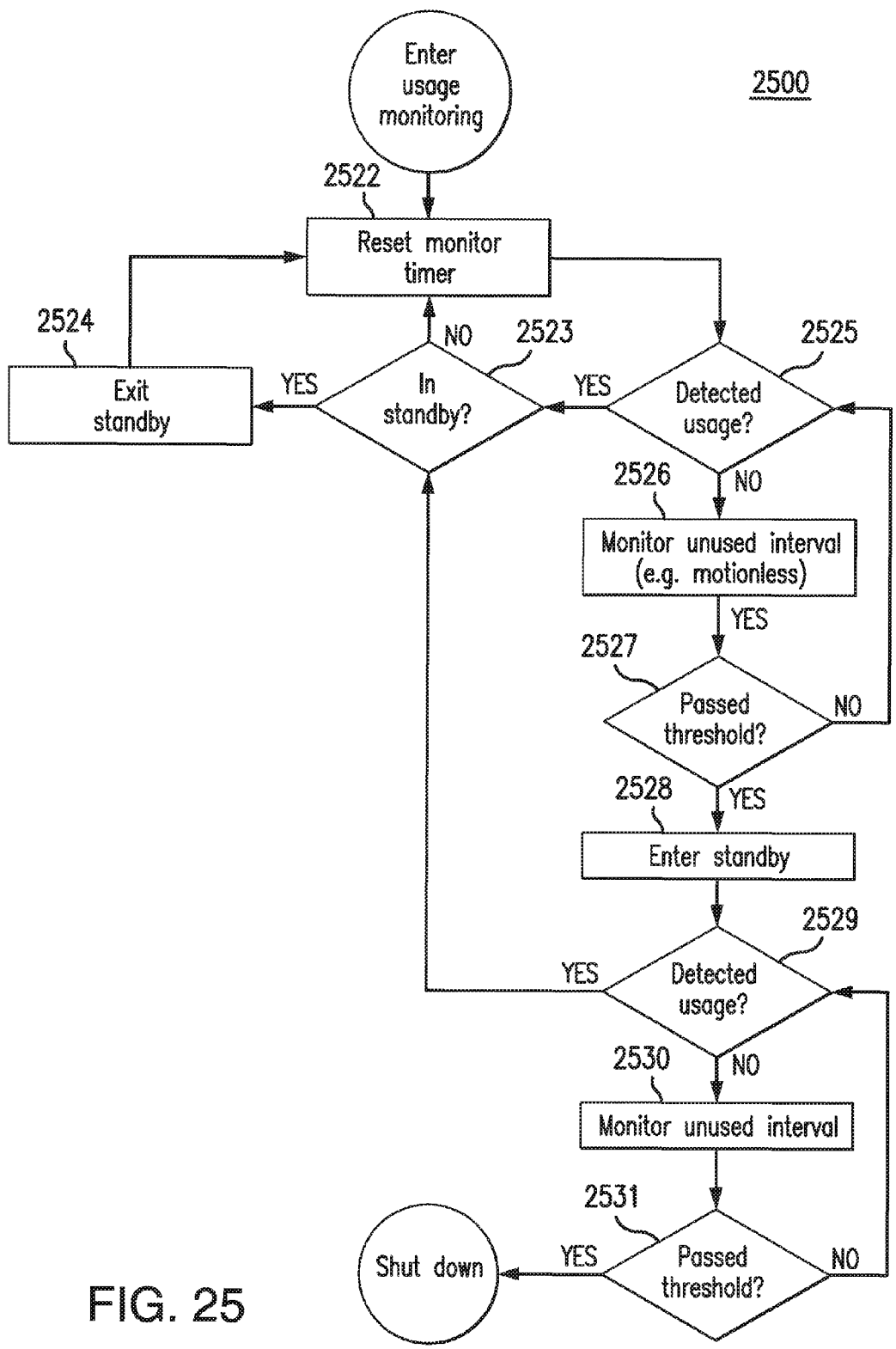
FIG. 25 illustrates a method for monitoring usage of the intraoral mirror.

FIG. 25 illustrates a process 2500 for monitoring usage of the intraoral mirror to conserve power.

At step 2522, an "unused interval" timer, indicating a length of a time interval in which the smart mirror device is not being used, is reset. At step 2525, usage detection is validated. In some embodiments, usage detection includes motion detection. In some embodiments, motion detection is performed by processing measurements of acceleration of smart mirror in one or more axes. In some embodiments, motion detection is performed by processing measurement of changes in angles of smart mirror relative to one or more axes. In some embodiments, motion detection is performed by processing a set of temporally successive images captured by smart mirror, for example, identifying changes among the images. In may be appreciated that various ways to detect motion of smart mirror exist, the invention is not so limited. In some embodiments, usage detection includes analyzing the orientation of smart mirror, for example checking if it lays horizontally (if so it might be left on table or a tray). In some embodiments, usage detection includes processing images captured by smart mirror, for example to assert that viewfinder mirror is in an intraoral environment. In some embodiments, a plurality of such condition validations are used to determine whether smart mirror is in use.

At step 2526, usage has not been detected, and an unused interval is determined. At step 2527, said interval is compared to a threshold. At step 2528, said interval surpasses a threshold, and smart mirror is set to a standby state in which its energy consumption is reduced, for example, by reducing or cutting off the energy supply to one or more of its components and/or suppressing or altering one or more of its software processes.

At step 2529, usage detection is further validated. At step 2530, usage has not been detected, and an unused interval is calculated, for a period in which smart mirror is in standby mode. At step 2531, said interval is compared to a threshold. If the interval surpasses a threshold, the smart mirror is shut down to further reduce its energy consumption, for example, by reducing or cutting off the energy supply to one or more or all of its components and/or suppressing or altering one or more or all of its software processes. At step 2523, usage has been detected and power mode is standby is checked.

At step 2524, smart mirror exits standby mode including, but not limited to, resuming power to one or more of its components and/or resuming one or more of its software processes.

J. Alternative Embodiments of the Intraoral Mirror

Figure 26:
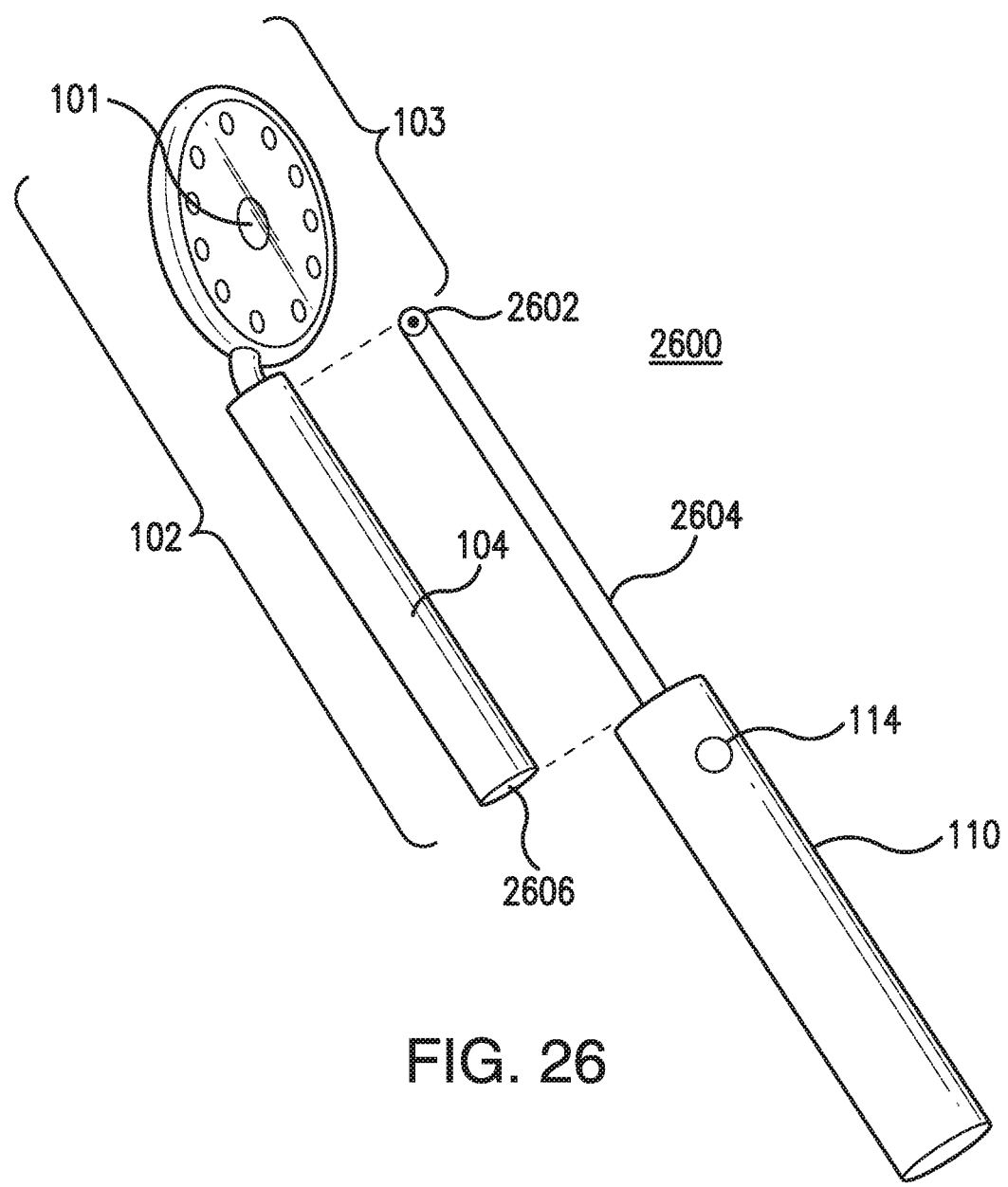
FIG. 26 is a diagram illustrating an alternative configuration of the intraoral mirror where an image sensor is placed on a non-autoclavable portion of the mirror.

FIG. 26 is a diagram 2600 illustrating an alternative configuration of the intraoral mirror where an image sensor is placed on a non-autoclavable portion of the mirror.

In diagram 2600, hand piece 110 includes an insert 2604 adapted to slide into a hollow part of appendage 104 of oral piece 102 through opening 2606. In some embodiments, this configuration allows improved resilience of oral piece 102 to a sterilization process, for example, by enabling to include electronic components in hand piece 110 instead of in oral piece 102, hence sparing them the sterilization process. As an illustrative example, in some embodiments, hand piece 110 (or particularly insert 2604) may include an image sensor 2602, instead of the sensor being included in oral piece 102. In this example, a prism, or light pipe or a small mirror internal to oral piece 102 (not shown) may transport light from semi-reflective surface 101 to image sensor 2602.

In an intraoral mirror, it is common that a round mirror is attached at an angle to a handle. The presence of the angle allows a more comfortable operation of an intraoral during treatment. However, viewfinder mirror 103 may be at a straight angle relative to appendage 104 and tube 2604 may extend image sensor 2602 to semi-reflective surface 101, obviating the need for a light pipe. A joint may also be used to extend image sensor 2602 to semi-reflective surface 101, allowing mirror 103 to be angled relative to appendage 104, without the need for a light pipe. This is illustrated in FIG. 27.

Figure 27:
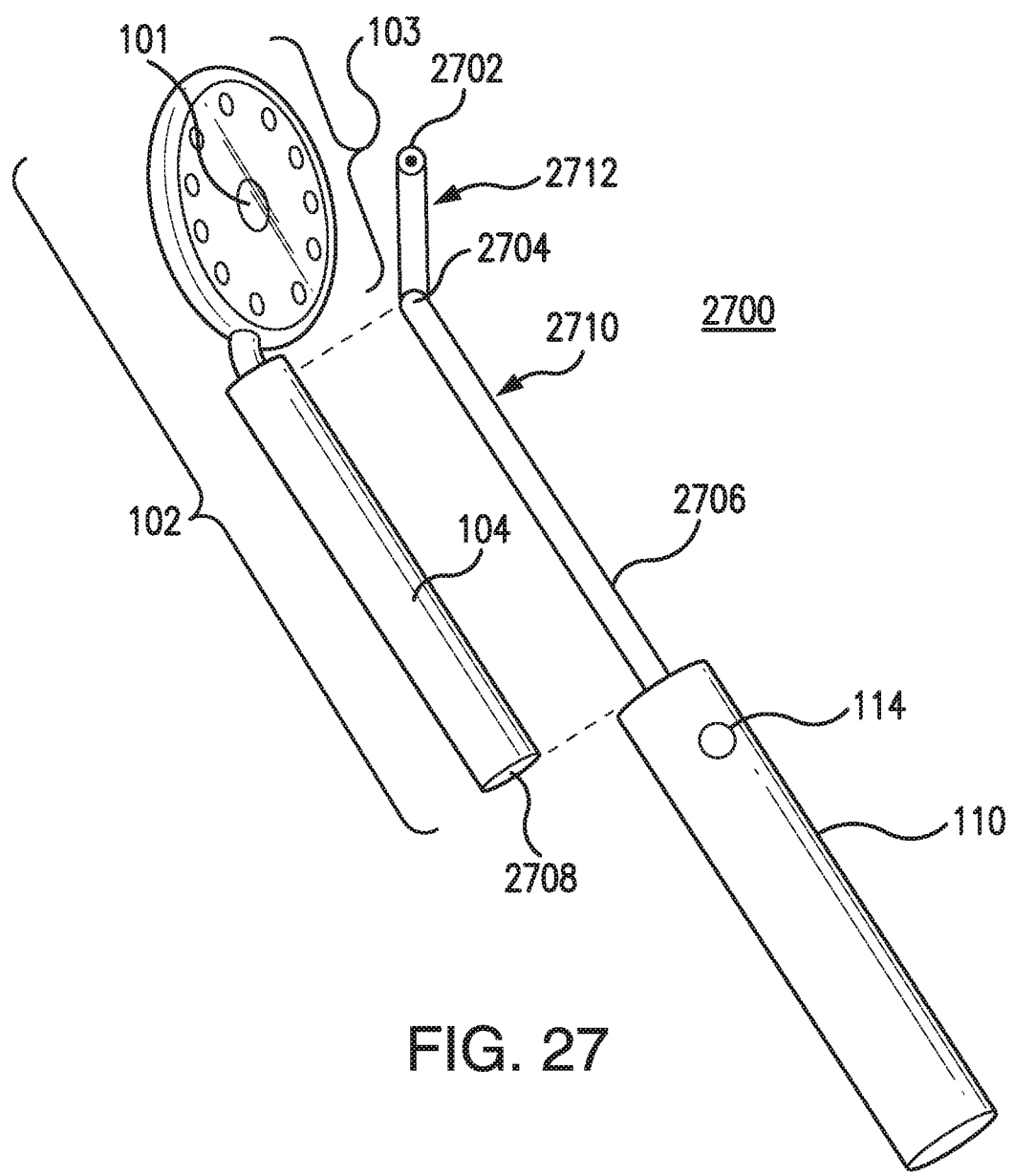
FIG. 27 is a diagram illustrating an alternative configuration of the intraoral mirror where an image sensor is placed on a jointed appendage of a non-autoclavable portion of the mirror.

FIG. 27 is a diagram 2700 illustrating an alternative configuration of the intraoral mirror where an image sensor is placed on a jointed appendage of a non-autoclavable portion of the mirror.

In particular, in diagram 2700, oral piece 102 is configured such that viewfinder mirror 103 is at an angle with (at least part of) tube 104. Insert 2706 of hand piece 110 has a joint 2704 connecting a fixed section 2710 with a rotating section 2712. In some embodiments, a rotating section 2712 can be at a varying angle relative to fixed section 2710. In this way, as illustrated in FIGS. 26 and 27 an image sensor may be placed on a non-autoclavable portion of a smart mirror device.

Figure 28:
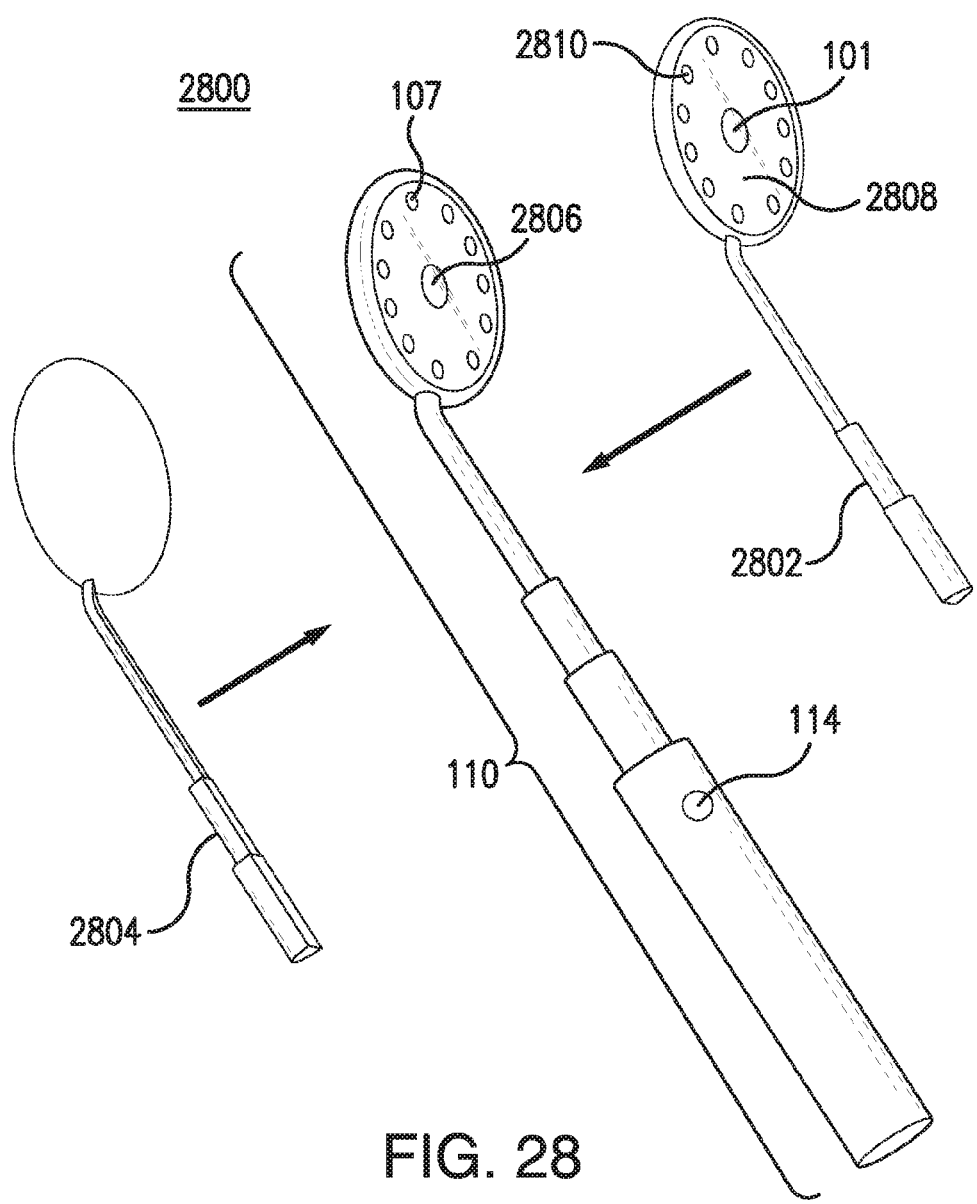
FIG. 28 is a diagram illustrating an alternative configuration of the intraoral mirror where the autoclavable portion detaches into two pieces.

FIG. 28 is a diagram 2800 illustrating an alternative configuration of the intraoral mirror where the oral piece includes no electronics. In diagram 2800, hand piece 110 extends the entire length of the smart mirror device. The portion of hand piece 110 that enters a patent's mouth is enclosed by two oral pieces: a front 2802 and a back 2804. The front 2802 and back 2804 attach to form an impermeable seal to cover hand piece 110 to ensure that hand piece 110 does not come in contact with a patient's mouth. Hand piece 110 includes lights 107 and an image sensor 2806, perhaps covered by a transparent window. Front 2802 includes the mirror surface 2808, semi-reflective or transparent surface 101 to allow light to pass through to image sensor 2806, and windows or light pipes 2810 that allow light to be emitted from lights 107.

In another embodiment, the reflective mirror may be replaced by a display, and the image, perhaps processed as described above, from the sensor is displayed. Similarly, a semi-reflective mirror could conceal a display, so that, for example, a health care provider watches a tooth in the reflective mirror and an x-ray is displayed to show, for example, a root of a tooth.

Figure 29:
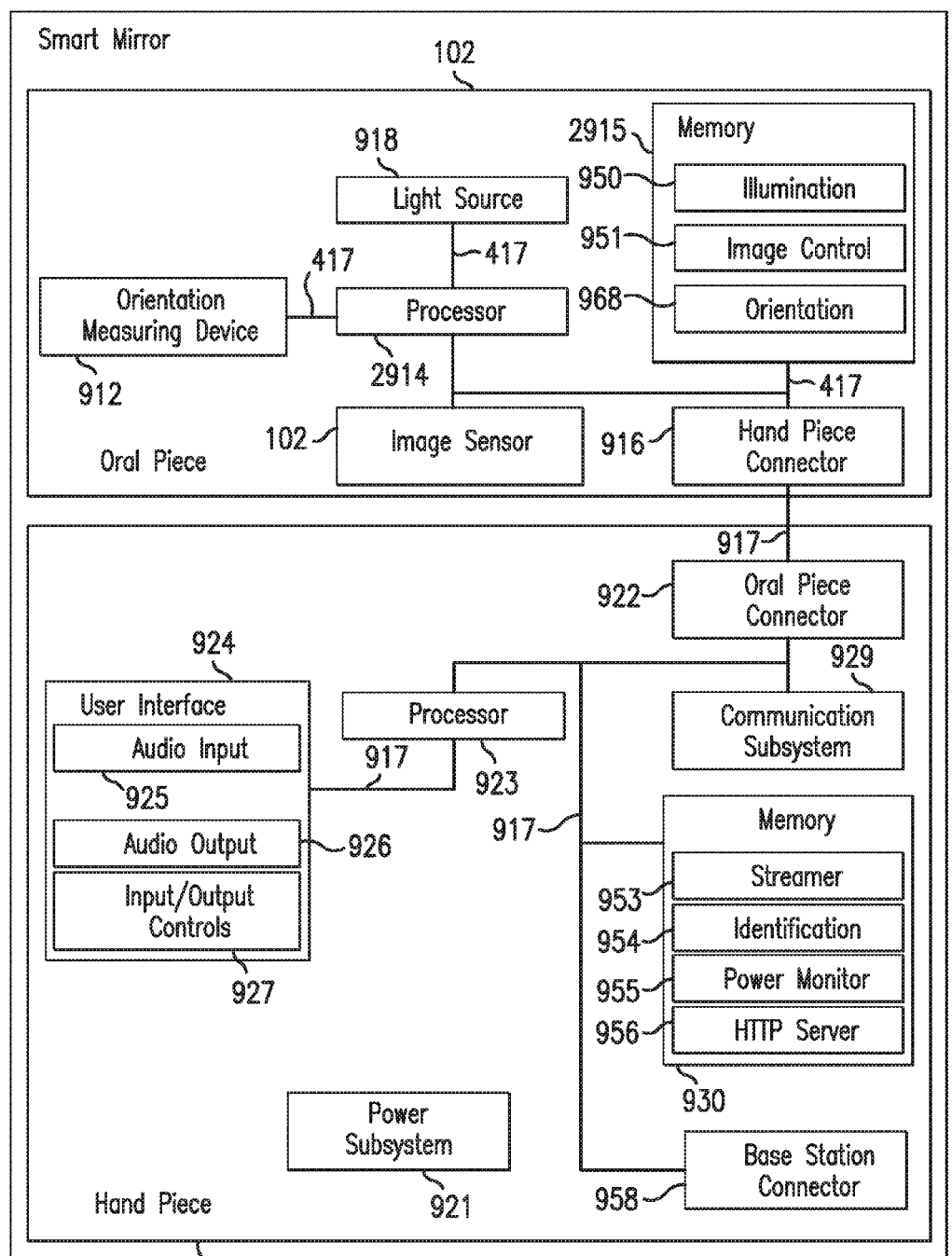
FIG. 29 is a block diagram illustrating an alternative embodiment of the smart mirror.

In another embodiment, it may be desirable to have more hardware and processing in the oral, autoclavable portion of the smart mirror device, as illustrated in FIG. 29.

FIG. 29 is a block diagram illustrating an alternative embodiment of a smart mirror 2900. Smart mirror 2900 differs from smart mirror device 100 described above principally in two respects. First, orientation measuring device 912 is located on oral piece 102, instead of hand piece 110. Second, oral piece 102 includes additional processing capabilities. Oral piece 102 includes a processor 923 and a memory 930.

Processor 923 executes software stored on a memory 930. The software includes an illumination controller module 950, image control module 951, and orientation calculator module 968, as described above for FIG. 1.

K. Conclusion

The databases disclosed herein may be any stored type of structured memory, including a persistent memory. In examples, this database may be implemented as a relational database or file system.

Each of the processors and modules in FIGS. 9, 11, 22 and 29 may be implemented in hardware, software, firmware, or any combination thereof implemented on a computing device. A computing device can include, but is not limited to, a device having a processor and memory, including a non-transitory memory, for executing and storing instructions. The memory may tangibly embody the data and program instructions. Software may include one or more applications and an operating system. Hardware can include, but is not limited to, a processor, a memory, and a graphical user interface display. The computing device may also have multiple processors and multiple shared or separate memory components. For example, the computing device may be a part of or the entirety of a clustered or distributed computing environment or server farm.

Identifiers, such as "(a)," "(b)," "(i)," "(ii)," etc., are sometimes used for different elements or steps. These identifiers are used for clarity and do not necessarily designate an order for the elements or steps.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for capturing photographs in a patient's mouth, comprising:
   (a) receiving an image captured from an image sensor affixed to a dental mirror, the dental mirror having a plurality of light sources;
   (b) determining a portion of the image to be darker than another portion of the image;
   (c) selecting, based on which portion was determined in (b) to be darker, a light source from the plurality of light sources such that the light source is selected to illuminate the determined portion more brightly than the other portion; and
   (d) increasing a brightness of the light source selected in (c).

2. The method of claim 1, further comprising:
   (e) determining whether a user has overridden automated illumination;
   (f) when the user is determined not to have overridden automated illumination, performing steps (a)-(d); and
   (g) when the user is determined to have overridden automated illumination, setting a brightness of the plurality of light sources according to a user setting.

3. The method of claim 1, further comprising:
   (e) determining whether a software module has overridden automated illumination;
   (f) when the software module is determined not to have overridden automated illumination, performing steps (a)-(d); and
   (g) when the software module is determined to have overridden automated illumination, setting a brightness of the plurality of light sources according to output of the software module.

4. The method of claim 1, further comprising:
   (e) monitoring the dental mirror to determining when it is not in use; and
   (f) when the dental mirror is determined not to be in use, entering into a standby mode that consumes a reduced amount of power.

5. The method of claim 4, wherein the monitoring (e) comprises monitoring an orientation measuring device on the dental mirror to determine when a time period has elapsed without substantial movement.

6. The method of claim 4, wherein the monitoring (e) comprises monitoring the image sensor on the dental mirror to determine when a time period has elapsed without substantial movement.

7. A program storage device tangibly embodying a program of instructions executable by at least one machine to perform a method for capturing photographs in a patient's mouth, comprising:
   (a) receiving an image captured from an image sensor affixed to a dental mirror, the dental mirror having a plurality of light sources;
   (b) determining a portion of the image to be darker than another portion of the image;
   (c) selecting, based on which portion was determined in (b) to be darker, a light source from the plurality of light sources such that the light source is selected to illuminate the determined portion more brightly than the other portion; and
   (d) increasing a brightness of the light source selected in (c).

8. The program storage device of claim 7, the method further comprising:
   (e) determining whether a user has overridden automated illumination;
   (f) when the user is determined not to have overridden automated illumination, performing steps (a)-(d); and
   (g) when the user is determined to have overridden automated illumination, setting a brightness of the plurality of light sources according to a user setting.

9. The program storage device of claim 7, the method further comprising:
   (e) determining whether a software module has overridden automated illumination;
   (f) when the software module is determined not to have overridden automated illumination, performing steps (a)-(d); and
   (g) when the software module is determined to have overridden automated illumination, setting a brightness of the plurality of light sources according to output of the software module.

10. The program storage device of claim 7, further comprising:
    (e) monitoring the dental mirror to determine when the dental mirror is not in use; and
    (f) when the dental mirror is determined not to be in use, entering into a standby mode that consumes a reduced amount of power.

11. The program storage device of claim 10, wherein the monitoring (e) comprises monitoring an orientation measuring device on the dental mirror to determine when a time period has elapsed without substantial movement.

12. The program storage device of claim 10, wherein the monitoring (e) comprises monitoring the image sensor on the dental mirror to determine when a time period has elapsed without substantial movement.

13. A device for capturing photographs in a patient's mouth, comprising:
- a dental mirror having a plurality of light sources;
- an image sensor, affixed to the dental mirror, that captures an image; and
- an illumination control module that (i) determines a portion of the image to be brighter than another portion of the image, (ii) selects, based on which portion was determined in (i) to be brighter, a light source from the plurality of light sources such that the light source is selected to illuminate the determined portion less brightly than the other portion, and (iii) decreases a brightness of the light source selected in (ii).

14. The device of claim 13, wherein the illumination control module (iv) determines whether a user has overridden automated illumination, (v) when the user is determined not to have overridden automated illumination, performs steps (i)-(iii), and (vi) when the user is determined to have overridden automated illumination, sets a brightness of the plurality of light sources according to a user setting.

15. The device of claim 13, wherein the illumination control module (iv) determines whether a software module has overridden automated illumination, (v) when the software module is determined not to have overridden automated illumination, performs steps (i)-(iii), and (vi) when the software module is determined to have overridden automated illumination, sets a brightness of the plurality of light sources according to output of the software module.

16. The device of claim 13, further comprising a power monitor module that monitors the dental mirror to determining when it is not in use, and when the dental mirror is determined not to be in use, enters into a standby mode that consumes a reduced amount of power.

17. The device of claim 16, wherein the power monitor module monitors an orientation measuring device on the dental mirror to determine when a time period has elapsed without substantial movement.

18. The device of claim 16, wherein the power monitor module monitors the image sensor on the dental mirror to determine when a time period has elapsed without substantial movement.

* * * * *